(12) United States Patent
Inoue et al.

(10) Patent No.: US 9,688,706 B2
(45) Date of Patent: Jun. 27, 2017

(54) ELECTROCHROMIC COMPOUND, ELECTROCHROMIC COMPOSITION, DISPLAY ELEMENT, AND DIMMING ELEMENT

(71) Applicants: Mamiko Inoue, Tokyo (JP); Masaomi Sasaki, Tokyo (JP); Tohru Yashiro, Kanagawa (JP); Keiichiroh Yutani, Kanagawa (JP); Yoshinori Okada, Kanagawa (JP); Sukchan Kim, Kanagawa (JP); Hiroyuki Takahashi, Kanagawa (JP); Koh Fujimura, Tokyo (JP); Yoshihisa Naijo, Kanagawa (JP); Kazuaki Tsuji, Kanagawa (JP); Shigenobu Hirano, Kanagawa (JP); Toshiya Sagisaka, Kanagawa (JP); Satoshi Yamamoto, Kanagawa (JP); Daisuke Goto, Kanagawa (JP); Keigo Takauji, Kanagawa (JP)

(72) Inventors: Mamiko Inoue, Tokyo (JP); Masaomi Sasaki, Tokyo (JP); Tohru Yashiro, Kanagawa (JP); Keiichiroh Yutani, Kanagawa (JP); Yoshinori Okada, Kanagawa (JP); Sukchan Kim, Kanagawa (JP); Hiroyuki Takahashi, Kanagawa (JP); Koh Fujimura, Tokyo (JP); Yoshihisa Naijo, Kanagawa (JP); Kazuaki Tsuji, Kanagawa (JP); Shigenobu Hirano, Kanagawa (JP); Toshiya Sagisaka, Kanagawa (JP); Satoshi Yamamoto, Kanagawa (JP); Daisuke Goto, Kanagawa (JP); Keigo Takauji, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/891,134

(22) PCT Filed: Jun. 26, 2014

(86) PCT No.: PCT/JP2014/067725
§ 371 (c)(1),
(2) Date: Nov. 13, 2015

(87) PCT Pub. No.: WO2014/208775
PCT Pub. Date: Dec. 31, 2014

(65) Prior Publication Data
US 2016/0108072 A1    Apr. 21, 2016

(30) Foreign Application Priority Data

Jun. 27, 2013 (JP) ................................. 2013-134671
May 12, 2014 (JP) ................................. 2014-098512
May 16, 2014 (JP) ................................. 2014-102085

(51) Int. Cl.
*G02F 1/155* (2006.01)
*C07F 9/6558* (2006.01)
(Continued)

(52) U.S. Cl.
CPC ........ *C07F 9/65583* (2013.01); *C07D 401/14* (2013.01); *C07F 7/1836* (2013.01);
(Continued)

(58) Field of Classification Search
USPC ................................................. 359/265, 266
See application file for complete search history.

(56) References Cited

U.S. PATENT DOCUMENTS 3,855,220 A    12/1974   Fischer
6,342,500 B1   1/2002    Khalifah et al.
(Continued)

FOREIGN PATENT DOCUMENTS

CN    101121695    2/2008
DE    2262188      5/1973
(Continued)

OTHER PUBLICATIONS

Fischer, Hanspeter et al, "One electron transfer properties and herbicidal activity of diquaternary salts of 2,4-di-(4-pyridyl)-1,3,5-triazines", Tetrahedron, 32(5), pp. 615-618 (1976).
(Continued)

*Primary Examiner* — Jack Dinh
(74) *Attorney, Agent, or Firm* — Cooper & Dunham LLP

(57) ABSTRACT

An electrochromic compound, represented by the following general formula (I);

(Continued)

General Formula (I)

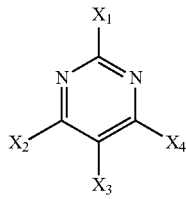

where $X_1$ to $X_4$ are each a substituent represented by the following general formula (II), an alkyl group that may contain a functional group, an aromatic hydrocarbon group that may contain a functional group, or a hydrogen atom, and at least two selected from $X_1$ to $X_4$ are the substituents represented by the general formula (II);

General Formula (II)

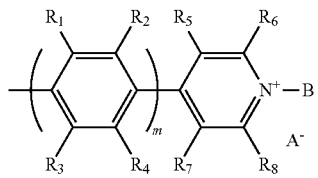

where $R_1$ to $R_8$ are each independently a hydrogen atom, or a monovalent group that may contain a substituent; B is a substituted or unsubstituted monovalent group that may contain a functional group; $A^-$ is a monovalent anion; and m is any of 0 to 3, and $R_1$ to $R_8$, B, and m may each independently be different when a plurality of the substituents represented by the general formula (II) are present.

16 Claims, 14 Drawing Sheets

(51) Int. Cl.
  C07D 401/14      (2006.01)
  C07F 7/18        (2006.01)
  C09K 9/02        (2006.01)
  G02F 1/15        (2006.01)
(52) U.S. Cl.
  CPC .............. *C09K 9/02* (2013.01); *G02F 1/15*
       (2013.01); *G02F 1/155* (2013.01); *C09K*
       *2211/1007* (2013.01); *C09K 2211/1029*
       (2013.01); *C09K 2211/1044* (2013.01); *C09K*
       *2211/1059* (2013.01)

(56) References Cited

U.S. PATENT DOCUMENTS

| 7,333,259 | B2 | 2/2008 | Hirano et al. |
| 8,384,983 | B2 | 2/2013 | Yashiro et al. |
| 8,531,754 | B2 | 9/2013 | Fujimura et al. |
| 8,593,715 | B2 | 11/2013 | Yashiro et al. |
| 8,687,262 | B2 | 4/2014 | Yashiro et al. |
| 2006/0204866 | A1 | 9/2006 | Hirano et al. |
| 2006/0215250 | A1 | 9/2006 | Shibuya et al. |
| 2008/0013152 | A1 | 1/2008 | Hirano et al. |
| 2009/0231663 | A1 | 9/2009 | Hirano et al. |
| 2009/0231664 | A1 | 9/2009 | Shibuya et al. |
| 2011/0222139 | A1 | 9/2011 | Naijo et al. |
| 2012/0050838 | A1 | 3/2012 | Hirano et al. |
| 2012/0069418 | A1 | 3/2012 | Kanitz et al. |
| 2012/0139824 | A1 | 6/2012 | Takahashi et al. |
| 2012/0194894 | A1 | 8/2012 | Yashiro et al. |

FOREIGN PATENT DOCUMENTS

| DE | 2262188 | 7/1973 |
| JP | 48-068740 | 9/1973 |
| JP | 2006-267829 | 10/2006 |
| JP | 2010-180307 | 8/2010 |
| JP | 2011-102287 | 5/2011 |
| WO | WO00/51987 | 9/2000 |
| WO | WO2008/077864 | 7/2008 |
| WO | WO2013/086803 | 6/2013 |

OTHER PUBLICATIONS

Launikonis, Anton et al, "Solar reduction of water. III. Improved electron-transfer agents for the system water-tris(2,2'-bipyridine)ruthenium dication-ethylenediaminetetraacetic acid-platinum", Aust. T. Chem., 35(7), pp. 1341-1355 (1982).

Bauer, R. et al, "New sensitizing relay compounds for hydrogen production", Int. J. Hydrogen Energy, 18(3), pp. 205-210 (1993).

International Search Report Issued Sep. 16, 2014 for counterpart International Patent Application No. PCT/JP2014/067725 filed Jun. 26, 2014.

Jun. 13, 2016 European search report in connection with corresponding European patent application No. 14818555.6.

Fischer, Hanspeter et al, "One electron transfer properties and herbicidal activity of diquaternary salts of 2,4-di-(4-pyridyl)-1,3,5-triazines", Tetrahedron, 32(5}, pp. 615-18 (1976).

Launikonis, Anton et al, "Solar reduction of water. III. Improved electron-transfer agents for the system water-tris(2,2'-bipyridine)ruthenium dication-ethylenediaminetetraacetic acid-platinum", Aust. T. Chem., 35(7), pp. 1341-55 (1982).

Bauer, R. et al, "New sensitizing relay compounds for hydrogen production", Int. J. Hydrogen Energy, 18(3}, pp. 205-10 (1993).

ELECTROCHROMIC COMPOUND, ELECTROCHROMIC COMPOSITION, DISPLAY ELEMENT, AND DIMMING ELEMENT

TECHNICAL FIELD

The present invention relates to an electrochromic compound, which exhibits black as colored, an electrochromic composition, and a display element and a dimming element each using the electrochromic compound or the electrochromic composition.

BACKGROUND ART

As for an electronic medium replacing paper, developments of electronic paper have been recently actively carried out.

The electronic paper has characteristics that the display device thereof is used like paper, and therefore requires properties different from conventional display devices, such as CRT and LCD. For example, required properties thereof are being a reflective display device as well as having high white reflectance and high contrast ratio, being able to display with high definition, giving the display a memory function, being driven at low voltage, being thin and light, and being inexpensive. Among them, as properties associated with a quality of a display, particularly white reflectivity and contrast ratio close to that of paper are highly demanded.

Previously, as for a display device for use as electronic paper, for example, proposed are a system using reflecting liquid crystals, a system using electrophoresis, a system using toner migration, and the like. Among them, a mainstream is an electrophoresis system, and the electrophoresis system has been system, however, it is currently widely used in electronic paper on a market. In this particularly difficult to provide high white reflectance. It has been known that the white reflectance provided by this system is low, i.e., about 40%, whereas the value thereof of paper is 80%, and the value thereof of news paper is 60%. Therefore, to provide high white reflectance is a large task for this system.

As for a promising technology for solving the aforementioned problem and realizing a reflecting display device, there is a system using electrochromic phenomenon. The phenomenon where, as voltage is applied, an oxidation-reduction reaction is reversibly caused depending on the polarity to thereby reversibly change color is called electrochromism. A display device utilizing coloring/discoloring (may also referred to as coloring and discoloring hereinafter) of the electrochromism is an electrochromic display device. Since this electrochromic display device is a reflecting display device, has a memory effect, and can be driven at low voltage, researches and developments of electrochromic devices have been widely conducted from a development of materials and designing of devices, as a promising option for a display device technology for electronic paper. It has been confirmed that white reflectance achieved by this method, i.e. 60%, is substantially the same value to that of paper (PTL 1).

An electrochromic display device is a system that can solve the majority of the aforementioned problems. The electrochromic compound used in a monochrome display element disclosed in PTL 2, which is produced using the electrochromic system, presents a color, which is slightly tinted with yellow, in a discolored state, and high white reflectance, which is one of characteristics of the electrochromic system, has not been achieved.

CITATION LIST

Patent Literature

PTL 1: Japanese Application Laid-Open (JP-A) No. 2006-267829
PTL 2: JP-A No. 2011-102287

SUMMARY OF INVENTION

Technical Problem

The present invention aims to provide an electrochromic compound, which exhibits a black color when colored, and is colorless without having an absorption band when discolored, an electrochromic composition (an electrochromic composition where the electrochromic compound is bonded or adsorbed to an electroconductive or semiconductive nanostructure), a display element, which uses the electrochromic compound or electrochromic composition, and has high white reflectance, and high contrast, and a dimming element having high transmittance, and high contrast.

Solution to Problem

The present inventors have diligently conducted researches, and come to an insight that the aforementioned problems can be solved by using an electrochromic compound having a certain structure. Based upon the insight, the present invention has been accomplished.

The electrochromic compound of the present invention is represented by the following general formula (I):

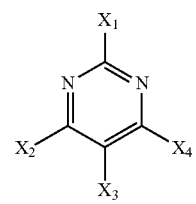

General Formula (I)

where $X_1$ to $X_4$ are each a substituent represented by the following general formula (II), an alkyl group that may contain a functional group, an aromatic hydrocarbon group that may contain a functional group, or a hydrogen atom, and at least two selected from $X_1$ to $X_4$ are the substituents represented by the general formula (II);

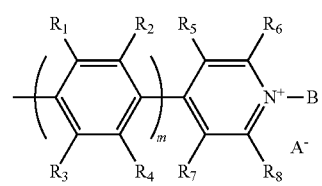

General Formula (II)

where $R_1$ to $R_8$ are each independently a hydrogen atom, or a monovalent group that may contain a substituent; B is a substituted or unsubstituted monovalent group that may contain a functional group; $A^-$ is a monovalent anion; and m is any of 0 to 3, and $R_1$ to $R_8$, B, and m may each independently be different when a plurality of the substituents represented by the general formula (II) are present.

Advantageous Effects of Invention

The present invention can provide an electrochromic compound or an electrochromic composition, which exhibits a black color when colored, and is colorless without having an absorption band when discolored.

DESCRIPTION OF EMBODIMENTS (Electrochromic Compound)

Figure 1:
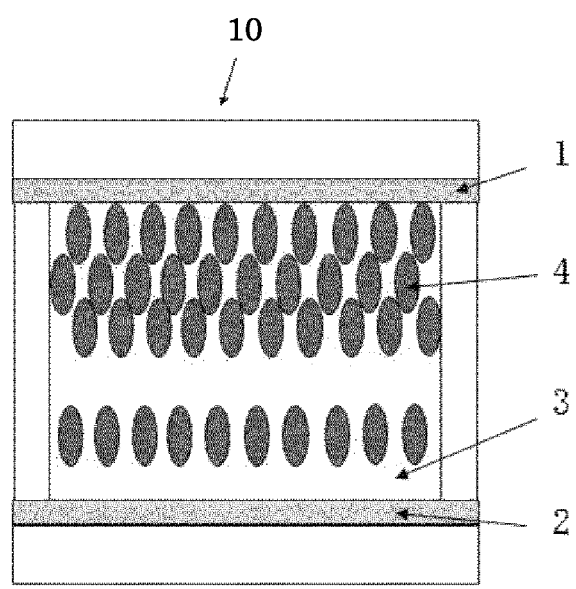
FIG. 1 is a schematic diagram illustrating an example of a structure of a typical display element using the electrochromic compound of the present invention.

In the first embodiment, the electrochromic compound of the present invention is represented by the following general formula (I);

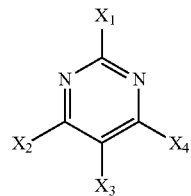

General Formula (I)

where $X_1$ to $X_4$ are each a substituent represented by the following general formula (II), an alkyl group that may contain a functional group, an aromatic hydrocarbon group that may contain a functional group, or a hydrogen atom, and at least two selected from $X_1$ to $X_4$ are the substituents represented by the general formula (II);

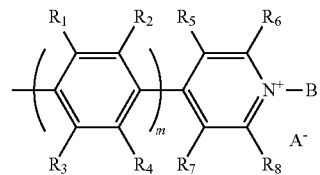

General Formula (II)

where $R_1$ to $R_8$ are each independently a hydrogen atom, or a monovalent group that may contain a substituent; B is a substituted or unsubstituted monovalent group that may contain a functional group; $A^-$ is a monovalent anion; and m is any of 0 to 3, and $R_1$ to $R_8$, B, and m may each independently be different when a plurality of the substituents represented by the general formula (II) are present.

These electrochromic compounds include those having structures represented by the following general formulae (VI) to (XII):

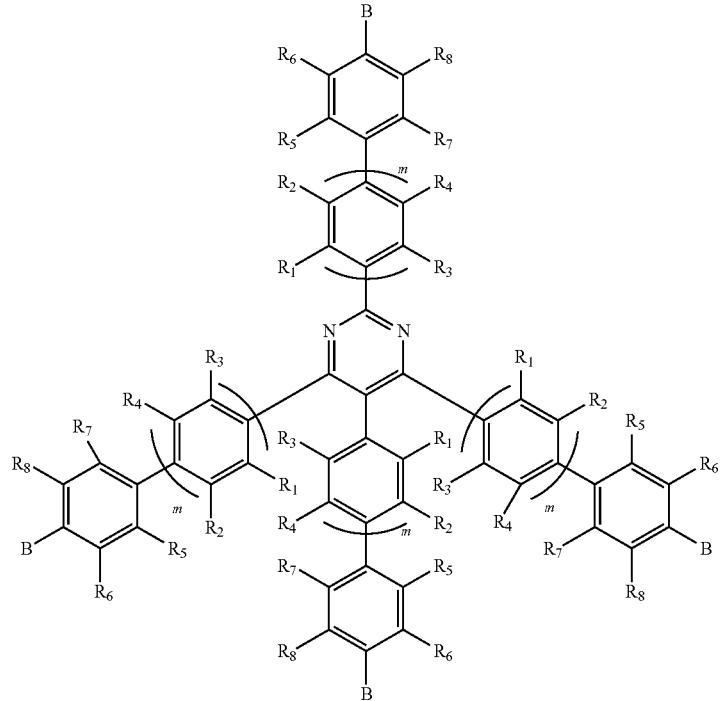

General Formula (VI)

In the general formula (VI), $R_1$ to $R_7$, B, and m each denote the same as in the general formula (II).

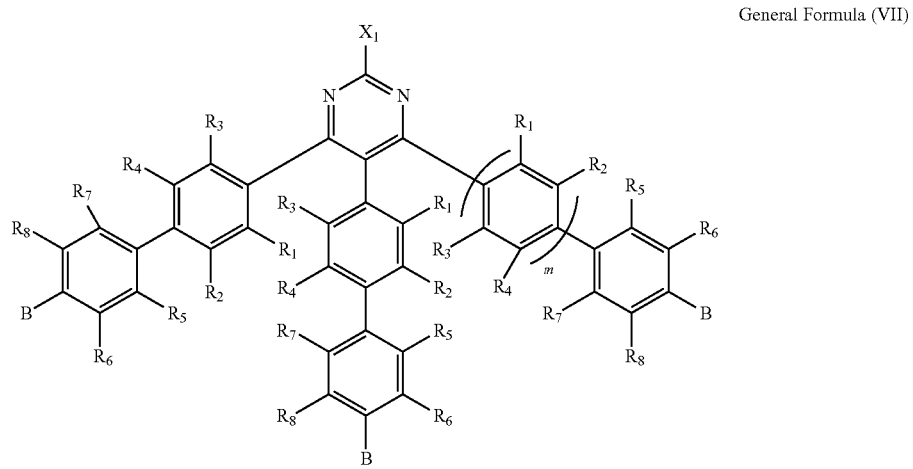

General Formula (VII)

In the general formula (VII), $R_1$ to $R_7$, B, and m each denote the same as in the general formula (II), and $X_1$ denotes the same as in the general formula (I).

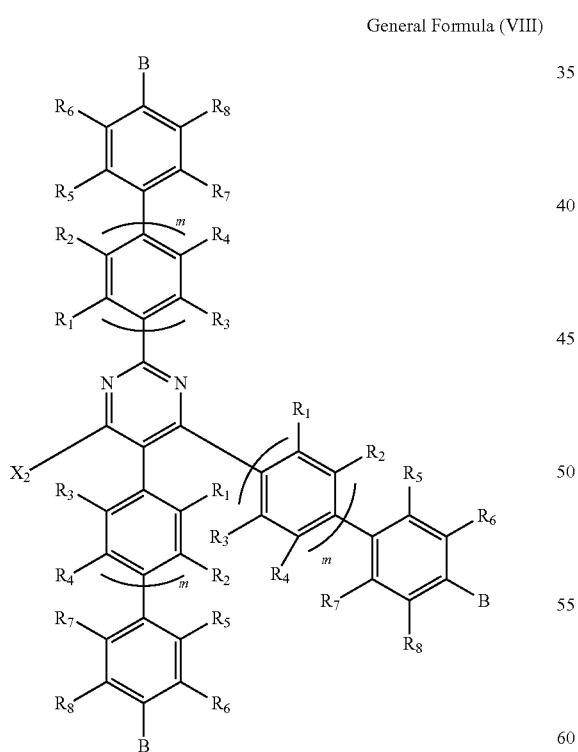

General Formula (VIII)

In the general formula (VIII) above, $R_1$ to $R_7$, B, and m each denote the same as in the general formula (II), and $X_1$ and $X_2$ each denote the same as in the general formula (I).

General Formula (IX)

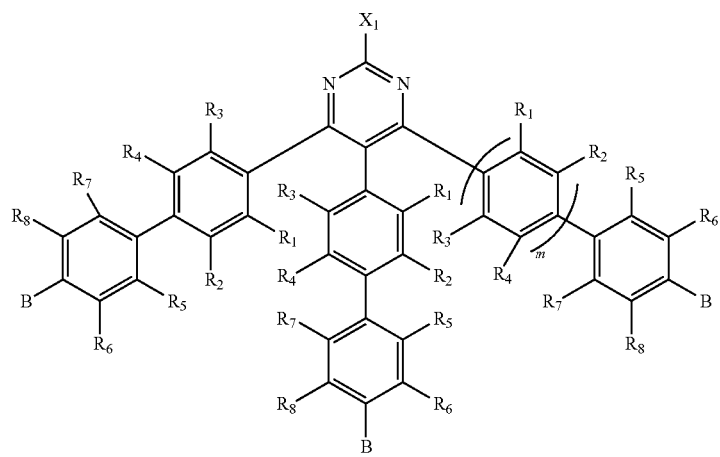

In the general formula (IX) above, $R_1$ to $R_7$, B, and m each denote the same as in the general formula (II), and $X_1$ and $X_2$ each denote the same as in the general formula (I).

General Formula (X)

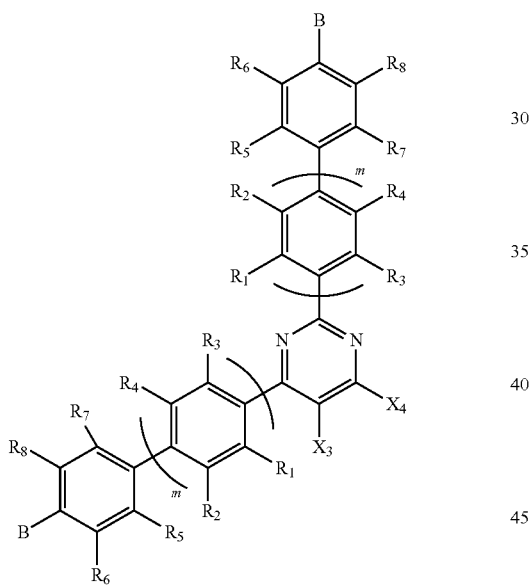

In the general formula (X), $R_1$ to $R_7$, B, and m each denote the same as in the general formula (II), and $X_4$ denotes the same as in the general formula (I).

General Formula (XI)

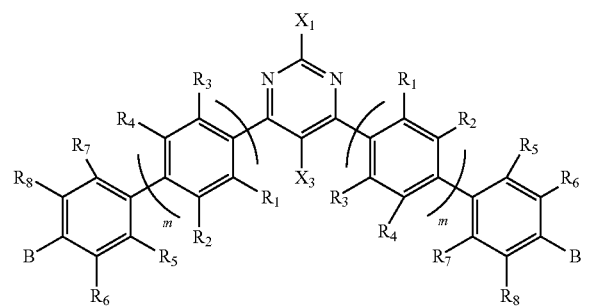

-continued

General Formula (XII)

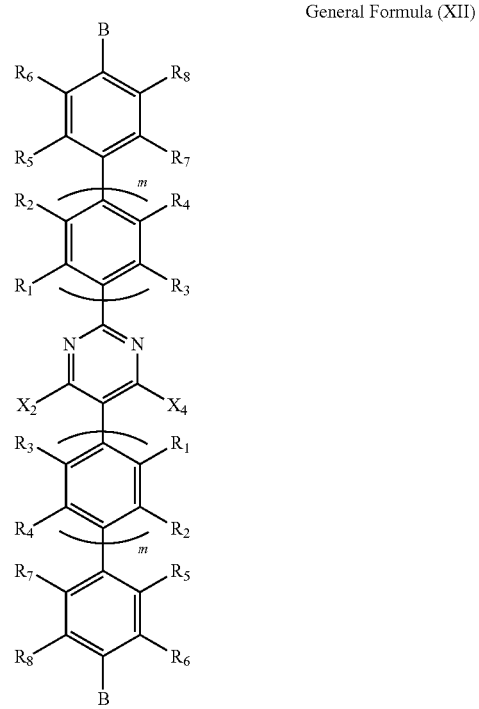

In the formulae above, $R_1$ to $R_7$, B, and m each denote the same as in the general formula (II), and $X_2$ and $X_4$ each denote the same as in the general formula (I).

Examples of the monovalent group represented by each of $R_1$ to $R_8$ in the general formula (II) include a monovalent group selected from the group consisting of a hydrogen atom, a halogen atom, a hydroxyl group, a nitro group, a cyano group, a carboxyl group, a carbonyl group, an amide group, an aminocarbonyl group, a sulfonic acid group, a sulfonyl group, a sulfonamide group, an aminosulfonyl group, an amino group, an alkyl group, an alkenyl group, an alkynyl group, an aryl group, an alkoxy group, an aryloxy group, an alkylthio group, an arylthio group, and a heterocyclic group. These monovalent groups may have a substituent. Moreover, examples of the monovalent group represented with B include a monovalent group selected from the group consisting of an alkyl group, an alkenyl group, an alkynyl group, and an aryl group, which may have a functional group. These monovalent groups may have a substituent. $A^-$ represents a monovalent anion.

Examples of the carbonyl group, which may have a substituent, include an alkoxy carbonyl group, an aryloxy carbonyl group, an alkyl carbonyl group, and an aryl carbonyl group. Examples of the aminocarbonyl group, which may have a substituent, include a monoalkyl aminocarbonyl group, a dialkyl aminocarbonyl group, a monoaryl aminocarbonyl group, and a diaryl aminocarbonyl group. Examples of the sulfonyl group, which may have a substituent, include an alkoxy sulfonyl group, an aryloxy sulfonyl group, an alkyl sulfonyl group, and an aryl sulfonyl group. Examples of the aminosulfonyl group, which may have a substituent, include a monoalkyl aminosulfonyl group, a dialkyl aminosulfonyl group, a monoaryl aminosulfonyl group, and a diaryl aminosulfonyl group. Examples of the amino group, which may have a substituent, include a monoalkyl amino group, and a dialkyl amino group. These monovalent groups may further have a substituent.

Specifically, examples of the monovalent groups represented with $R_1$ to $R_8$ in the general formula (II) include a hydrogen atom, a halogen atom, a hydroxyl group, a nitro group, a cyano group, a carboxyl group, a substituted or unsubstituted alkoxy carbonyl group, a substituted or unsubstituted aryloxy carbonyl group, a substituted or unsubstituted alkyl carbonyl group, a substituted or unsubstituted aryl carbonyl group, an amide group, a substituted or unsubstituted monoalkyl aminocarbonyl group, a substituted or unsubstituted dialkyl aminocarbonyl group, a substituted or unsubstituted monoaryl aminocarbonyl group, a substituted or unsubstituted diaryl aminocarbonyl group, a sulfonic acid group, a substituted or unsubstituted alkoxy sulfonyl group, a substituted or unsubstituted aryloxy sulfonyl group, a substituted or unsubstituted alkyl sulfonyl group, a substituted or unsubstituted aryl sulfonyl group, a sulfonamide group, a substituted or unsubstituted monoalkyl aminosulfonyl group, a substituted or unsubstituted dialkyl aminosulfonyl group, a substituted or unsubstituted monoaryl aminosulfonyl group, a substituted or unsubstituted diaryl aminosulfonyl group, an amino group, a substituted or unsubstituted monoalkyl amino group, a substituted or unsubstituted dialkyl amino group, a substituted or unsubstituted alkyl group, a substituted or unsubstituted alkenyl group, a substituted or unsubstituted alkynyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, and a substituted or unsubstituted heterocyclic group.

Examples of the monovalent group represented with B include an alkyl group that may have a functional group, an alkenyl group that may have a functional group, an alkynyl group that may have a functional group, and an aryl group that may have a functional group.

These monovalent groups may have a substituent. Moreover, $A^-$ is a monovalent anion, and is not particularly limited as long as it stably forms a pair with a cation site, but preferred is Br ion ($Br^-$), Cl ion ($Cl^-$), $ClO_4$ ion ($ClO_4^-$), $PF_6$ ion ($PF_6^-$), or $BF_4$ ion ($BF_4^-$).

Owing to the monovalent groups of $R_1$ to $R_8$, solubility to a solvent is provided to an electrochromic compound, and therefore a production process of an element becomes easy.

Note that, in the electrochromic compound of the present invention, $R_1$ to $R_8$ and B are preferably selected so that the general formula (I) forms a symmetric structure, in view of easiness of synthesis and improvement in stability.

In the first embodiment, moreover, the electrochromic compound of the present invention may be represented by the following general formula (III), (IV), or (V).

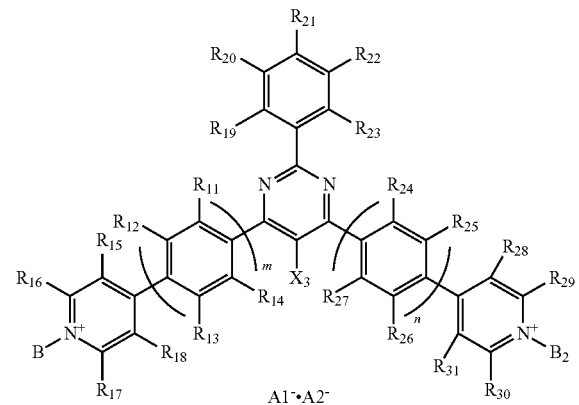

General Formula (III)

In the general formula (III), $X_3$ is a hydrogen atom or a monovalent group that may have a substituent; $R_{11}$ to $R_{31}$ are each independently a hydrogen atom or a monovalent group that may have a substituent; $B_1$ and $B_2$ are each independently a substituted or unsubstituted monovalent group that may have a functional group; and $A1^-$ and $A2^-$ are each independently a monovalent anion.

(5) Electrochromic Compound Represented by the General Formula (IV) or the General Formula (V)

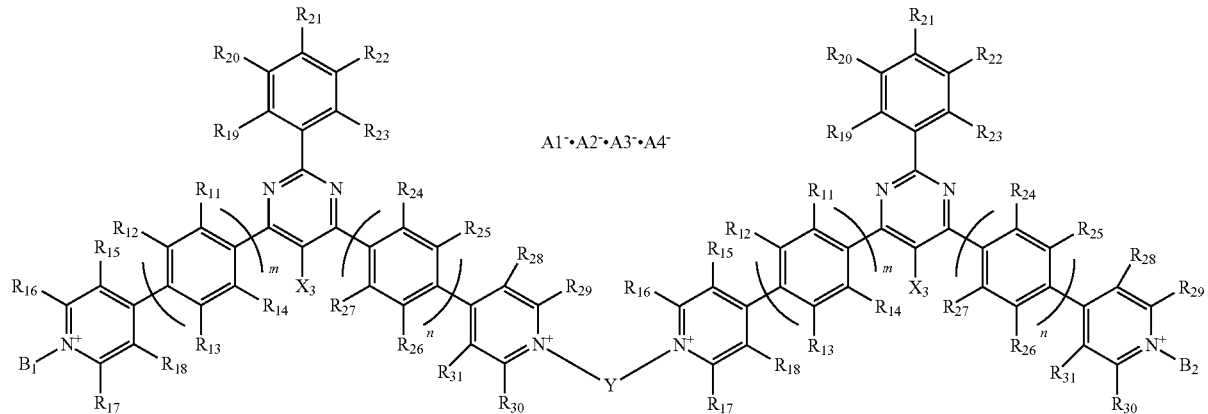

General Formula (IV)

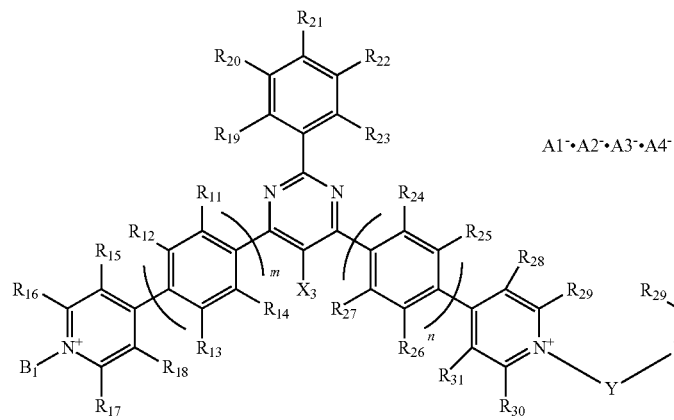
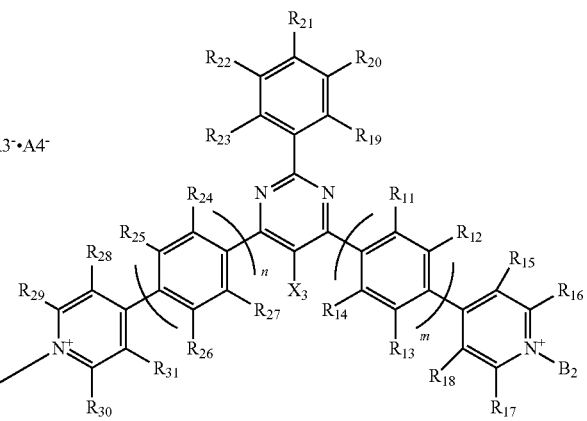

General Formula (V)

In the general formulae (IV) and (V), $X_3$ is a hydrogen atom or a substituted or unsubstituted monovalent group; $R_{11}$ to $R_{31}$ are each independently a hydrogen atom or a substituted or unsubstituted monovalent group; $B_1$ and $B_2$ are each independently a substituted or unsubstituted aliphatic hydrocarbon group or aromatic hydrocarbon group, which may have a functional group; $A1^-$ and $A2^-$ are each a monovalent anion; m and n are each independently 1, 2, or 3; and Y is a bivalent organic group, which contains at least one methylene group, and may further contain a substituted or unsubstituted aliphatic hydrocarbon group or aromatic hydrocarbon group.

The monovalent group represented with $X_3$ and the monovalent groups represented with $R_{11}$ to $R_{31}$ in the general formula (III) are each independently a monovalent group selected from the group consisting of a hydrogen atom, a halogen atom, a hydroxyl group, a nitro group, a cyano group, a carboxyl group, a carbonyl group, an amide group, an aminocarbonyl group, a sulfonic acid group, a sulfonyl group, a sulfonamide group, an aminosulfonyl group, an amino group, an alkyl group, an alkenyl group, an alkynyl group, an aryl group, an alkoxy group, an aryloxy group, an alkylthio group, an arylthio group, and a heterocyclic group. These monovalent groups may each have a substituent. The monovalent groups represented with $R_1$ and $R_2$ are each independently a monovalent group selected from the group consisting of an alkyl group, an alkenyl group, an alkynyl group, and an aryl group, which may have a functional group. These monovalent groups may have a substituent. $A1^-$ and $A2^-$ are each independently a monovalent anion.

Examples of the carbonyl group, which may have a substituent, include an alkoxy carbonyl group, an aryloxy carbonyl group, an alkyl carbonyl group, and an aryl carbonyl group. Examples of the aminocarbonyl group, which may have a substituent, include a monoalkyl aminocarbonyl group, a dialkyl aminocarbonyl group, a monoaryl aminocarbonyl group, and diaryl aminocarbonyl group. Examples of the sulfonyl group, which may have a substituent, include an alkoxy sulfonyl group, an aryloxy sulfonyl group, an alkyl sulfonyl group, and an aryl sulfonyl group. Examples of the aminosulfonyl group, which may have a substituent, include a monoalkyl aminosulfonyl group, a dialkyl aminosulfonyl group, a monoaryl aminosulfonyl group, and diaryl aminosulfonyl group. Examples of the amino group include a monoalkyl amino group, and dialkyl amino group. These monovalent groups may further have a substituent.

Specifically, examples of the monovalent group represented with $X_3$ and the monovalent groups represented with $R_{11}$ to $R_{31}$ in the general formula (III) include a hydrogen atom, a halogen atom, a hydroxyl group, a nitro group, a cyano group, a carboxyl group, a substituted or unsubstituted alkoxy carbonyl group, a substituted or unsubstituted aryloxy carbonyl group, a substituted or unsubstituted alkyl carbonyl group, a substituted or unsubstituted aryl carbonyl group, an amide group, a substituted or unsubstituted monoalkyl aminocarbonyl group, a substituted or unsubstituted dialkyl aminocarbonyl group, a substituted or unsubstituted monoaryl aminocarbonyl group, a substituted or unsubstituted diaryl aminocarbonyl group, a sulfonic acid group, a substituted or unsubstituted alkoxy sulfonyl group, a substituted or unsubstituted aryloxy sulfonyl group, a substituted or unsubstituted alkyl sulfonyl group, a substituted or unsubstituted aryl sulfonyl group, a sulfonamide group, a substituted or unsubstituted monoalkyl aminosulfonyl group, a substituted or unsubstituted dialkyl aminosulfonyl group, a substituted or unsubstituted monoaryl aminosulfonyl group, a substituted or unsubstituted diaryl aminosulfonyl group, an amino group, a substituted or unsubstituted monoalkyl amino group, a substituted or unsubstituted dialkyl, a substituted or unsubstituted alkyl group, a substituted or unsubstituted alkenyl group, a substituted or unsubstituted alkynyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, and a substituted or unsubstituted heterocyclic group.

The monovalent groups represented with $R_1$ and $R_2$ are each independently an alkyl group that may have a functional group, an alkenyl group that may have a functional group, an alkynyl group that may have a functional group, or an aryl group that may have a functional group. These monovalent groups may have a substituent. Moreover, $A1^-$ and $A2^-$ are each independently a monovalent anion. The monovalent anion is not particularly limited, provided that it stably forms a pair with a cation site, but preferred is Br ion ($Br^-$), Cl ion ($Cl^-$), $ClO_4$ ion ($ClO_4^-$), $PF_6$ ion ($PF_6^-$), or $BF_4$ ion ($BF_4^-$).

Owing to the monovalent groups of $X_3$, and $R_{11}$ to $R_{31}$, solubility to a solvent is provided to an electrochromic compound, and therefore a production process of an element becomes easy.

Note that, in the electrochromic compound of the present invention, the monovalent group $X_3$, $R_{11}$ to $R_{31}$, and B ($B_1$, $B_2$) are preferably selected so that the general formula (III) forms a symmetric structure, in view of easiness of synthesis and improvement in stability.

Specific examples of the monovalent groups represented with $X_3$ and $R_{11}$ to $R_{31}$ in the general formulae (IV) and (V) are the same as the examples of the monovalent groups represented with $X_3$ and $R_{11}$ to $R_{31}$ in the general formula (III). Moreover, specific examples of B ($B_1$, $B_2$) in the general formulae (IV) and (V) are the same as the examples of B ($B_1$, $B_2$) in the general formula (III). Furthermore, the anions represented with $A1^-$, $A2^-$, $A3^-$, and $A4^-$ are the same as the anions $A1^-$ and $A2^-$ in the general formula (III).

Specific examples of the electrochromic compound of the present invention are listed as the following structural formulae (1) to (72), but the electrochromic compound of the present invention is not limited to these structural formulae.

Electrochromic Compound (1)

Structural Formula (1)

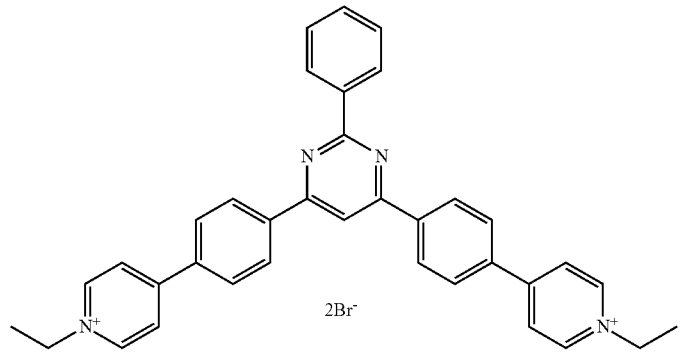

Electrochromic Compound (2)

Structural Formula (2)

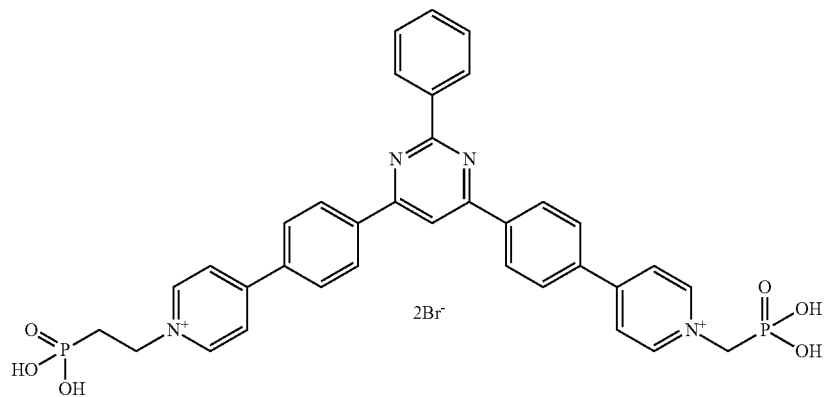

Electrochromic Compound (3)

Structural Formula (3)

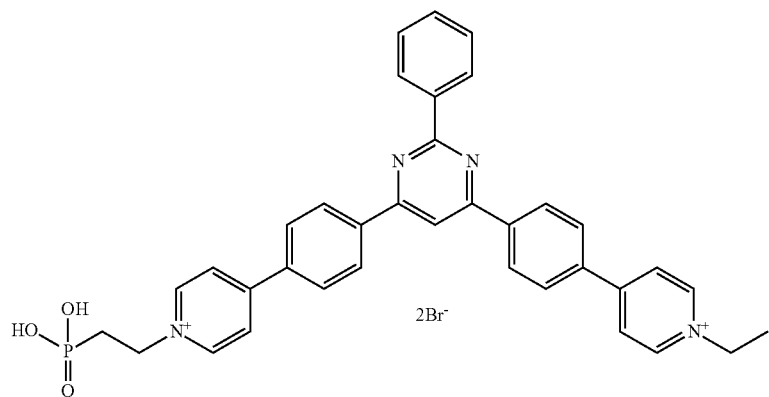

-continued
Electrochromic Compound (4)
Structural Formula (4)
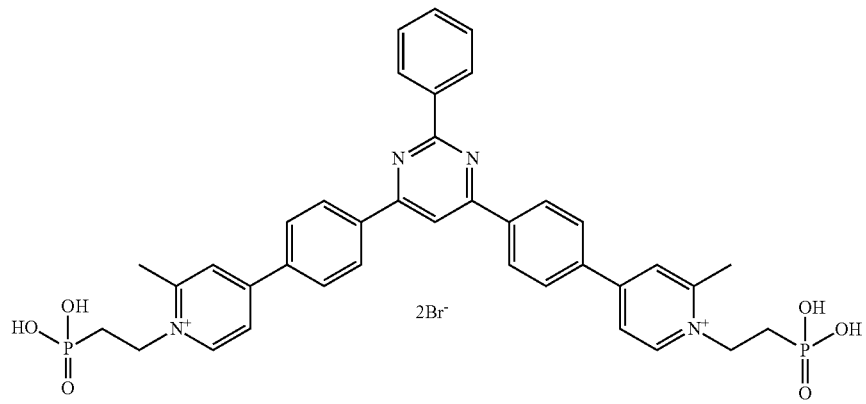
Electrochromic Compound (5)
Structural Formula (5)
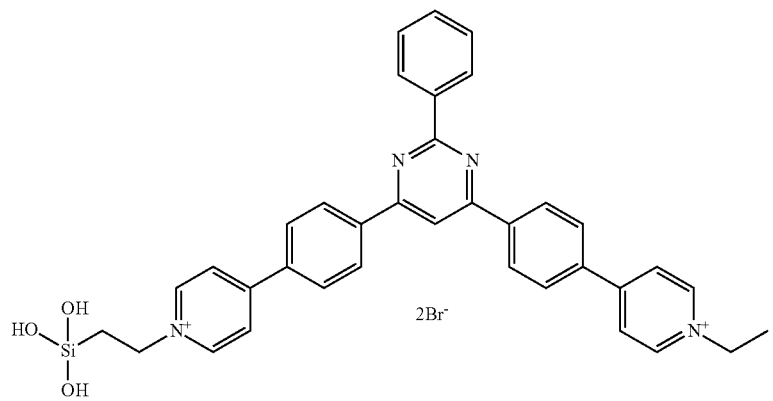
Electrochromic Compound (6)
Structural Formula (6)
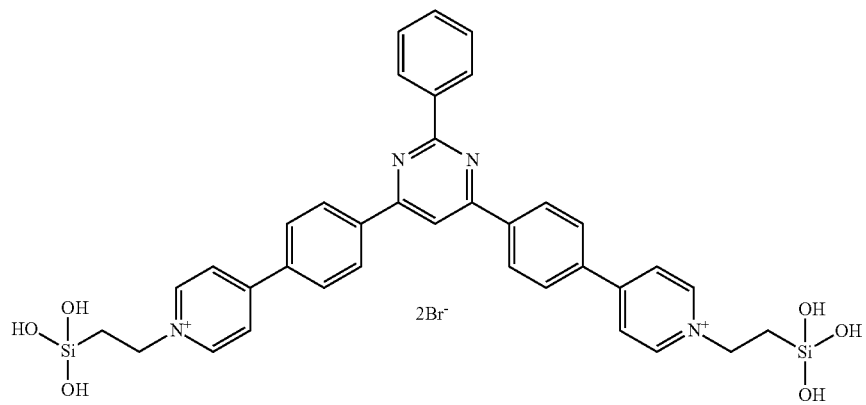

Electrochromic Compound (7)
Structural Formula (7)
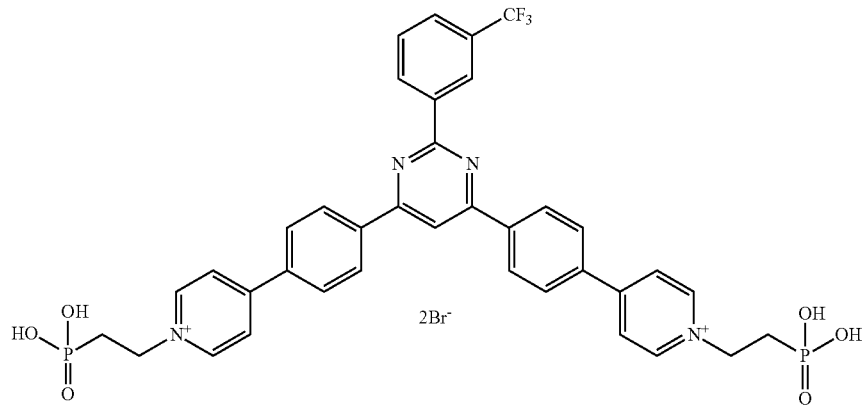
Electrochromic Compound (8)
Structural Formula (8)
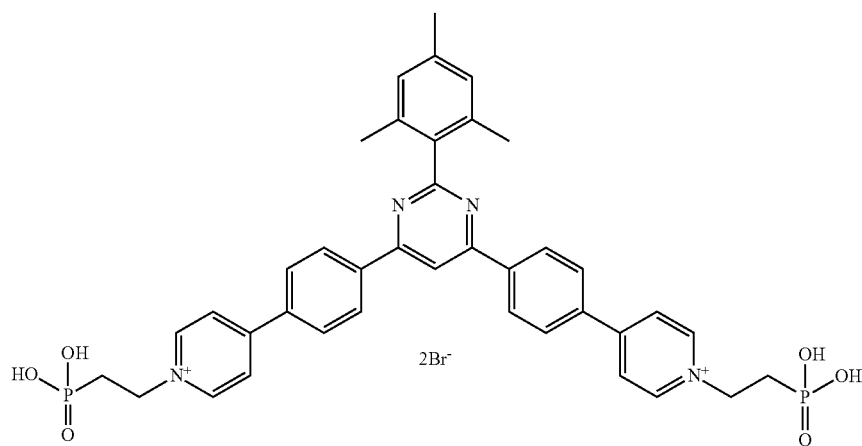
Electrochromic Compound (9)
Structural Formula (8)
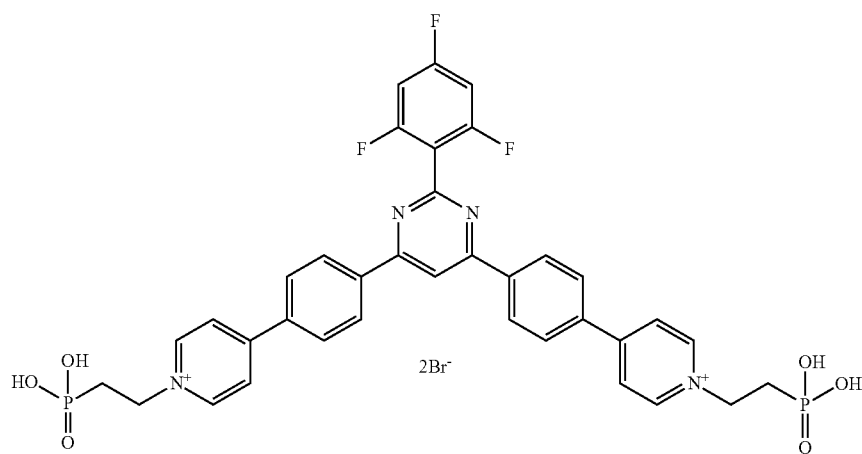

-continued
Electrochromic Compound (10)
Structural Formula (10)
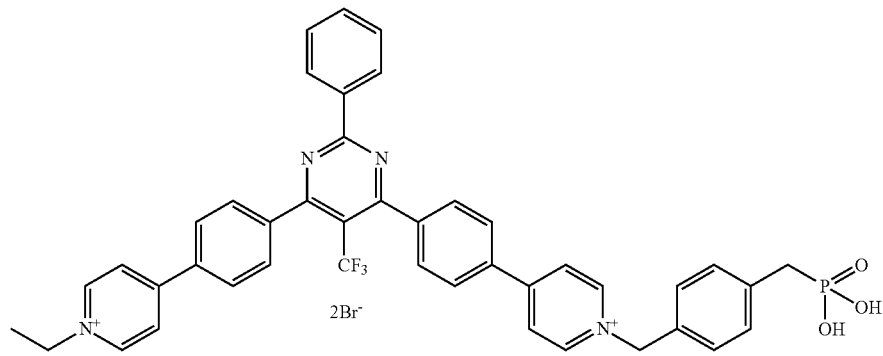
Electrochromic Compound (11)
Structural Formula (11)
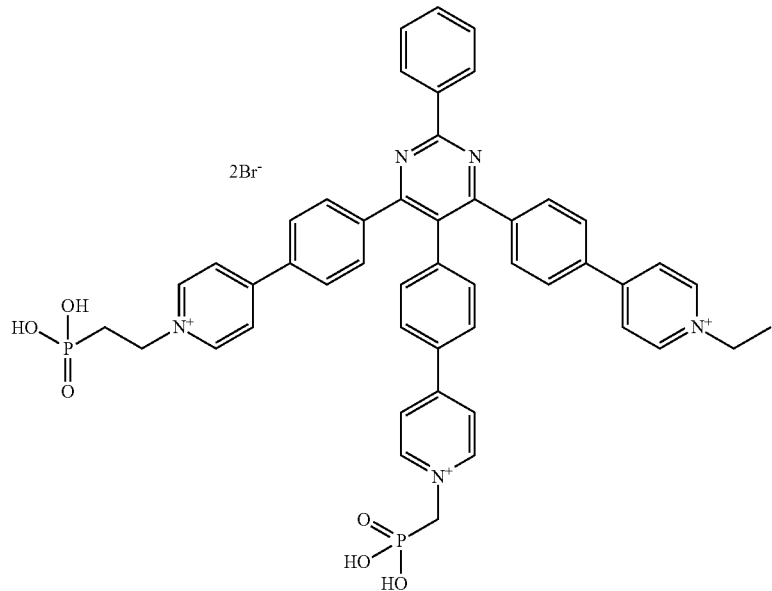
Electrochromic Compound (12)
Structural Formula (12)
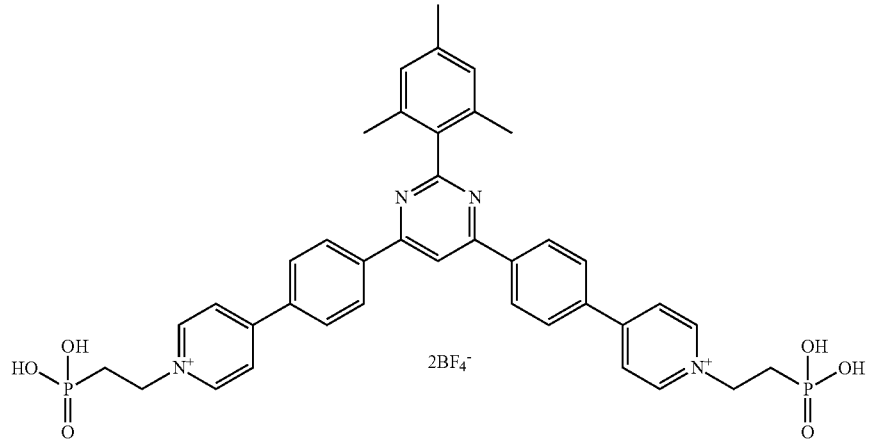

-continued
Electrochromic Compound (13)
Structural Formula (13)
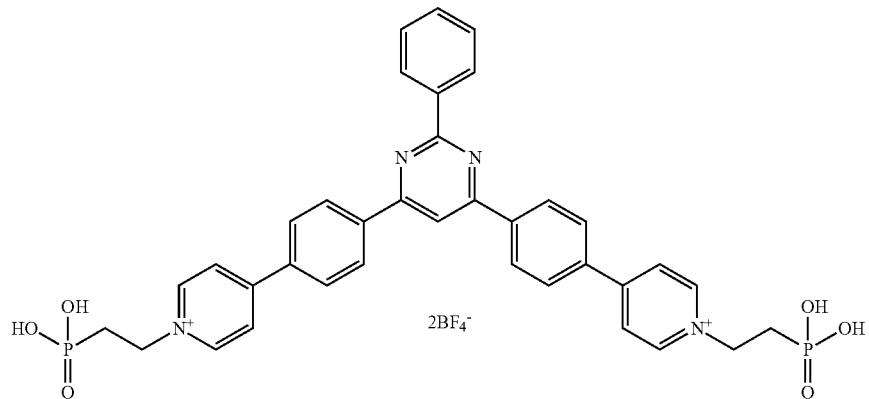
Electrochromic Compound (14)
Structural Formula (14)
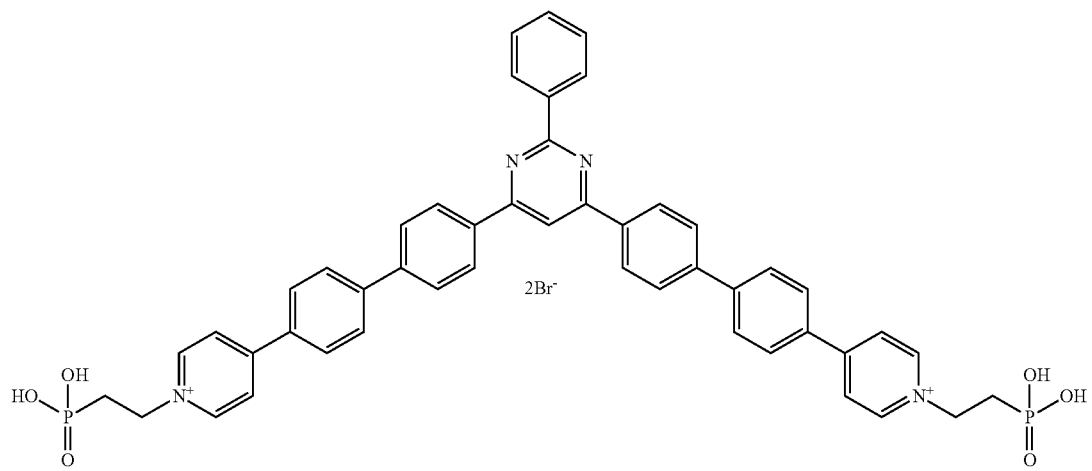
Electrochromic Compound (15)
Structural Formula (15)
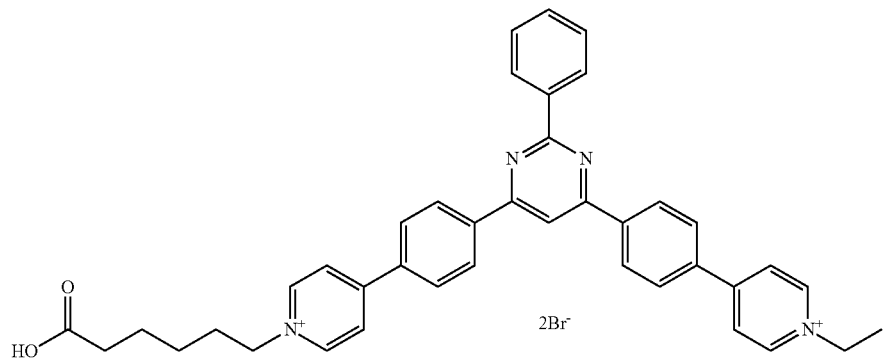

-continued
Electrochromic Compound (16)
Structural Formula (16)
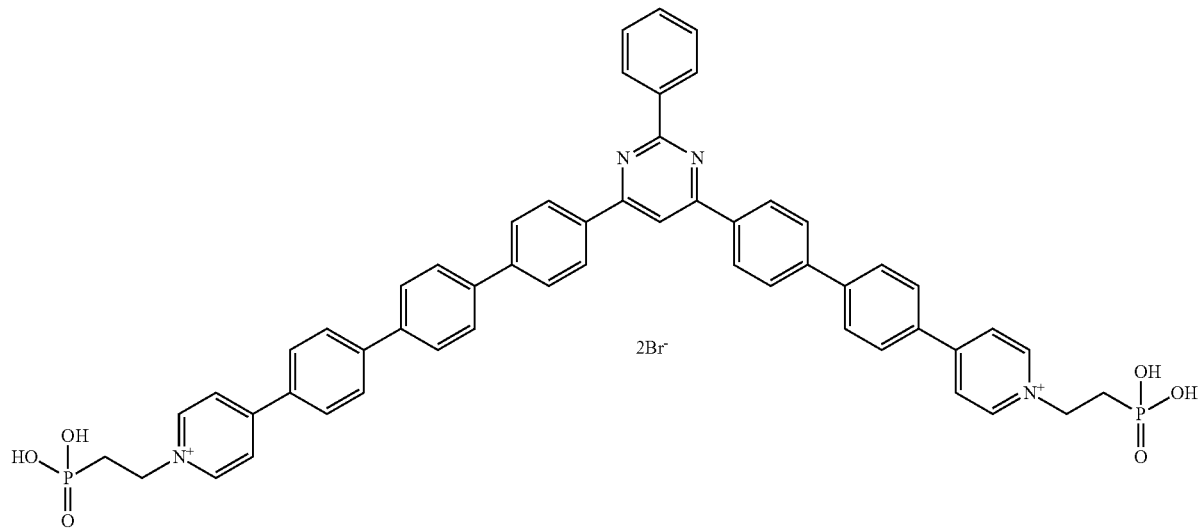
Electrochromic Compound (17)
Structural Formula (17)
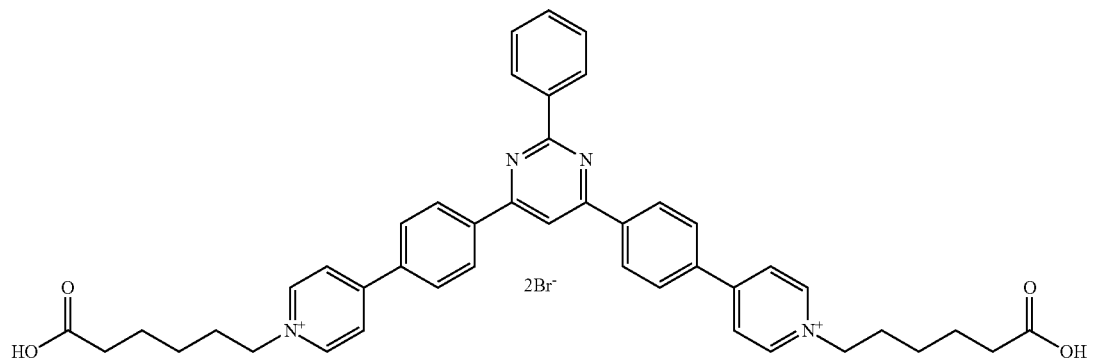
Electrochromic Compound (18)
Structural Formula (18)
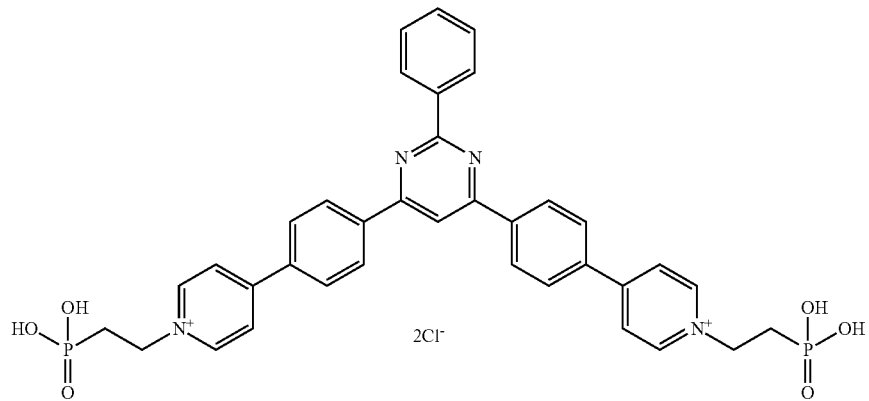

-continued
Electrochromic Compound (19)
Structural Formula (19)
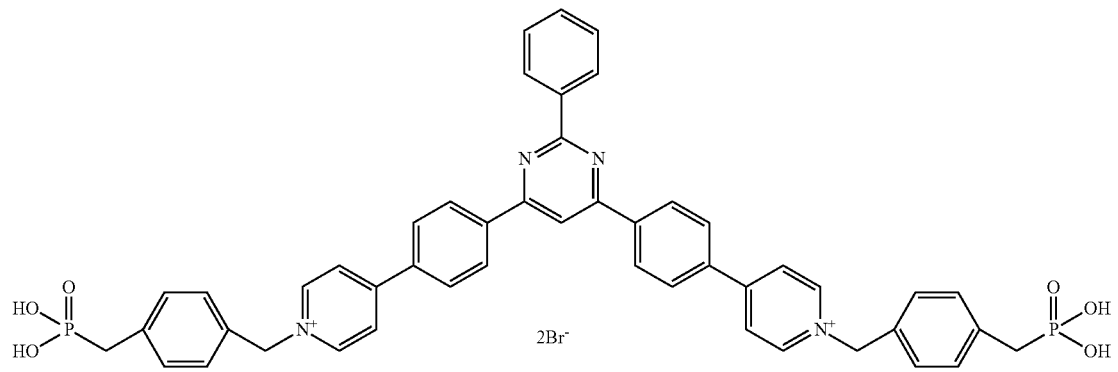
Electrochromic Compound (20)
Structural Formula (20)
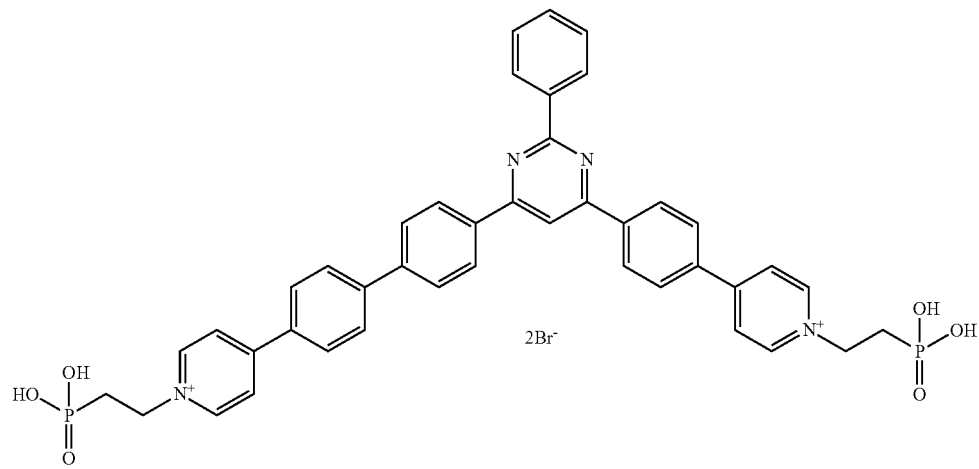
Electrochromic Compound (21)
Structural Formula (21)
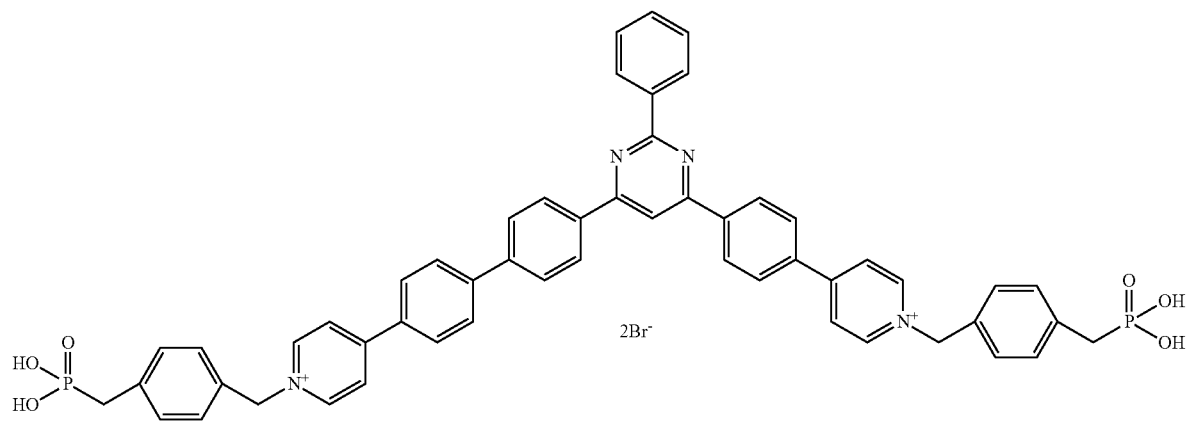

-continued
Electrochromic Compound (22)
Structural Formula (22)
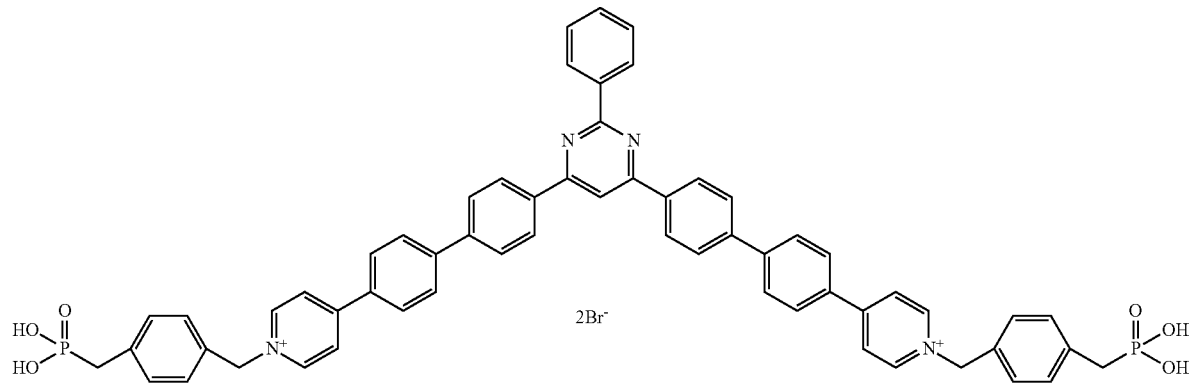
Electrochromic Compound (23)
Structural Formula (23)
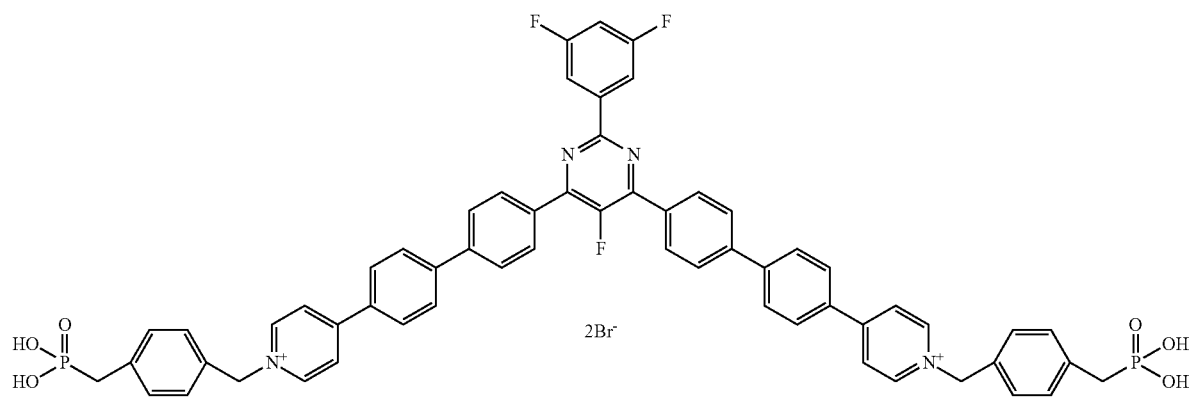
Electrochromic Compound (24)
Structural Formula (24)
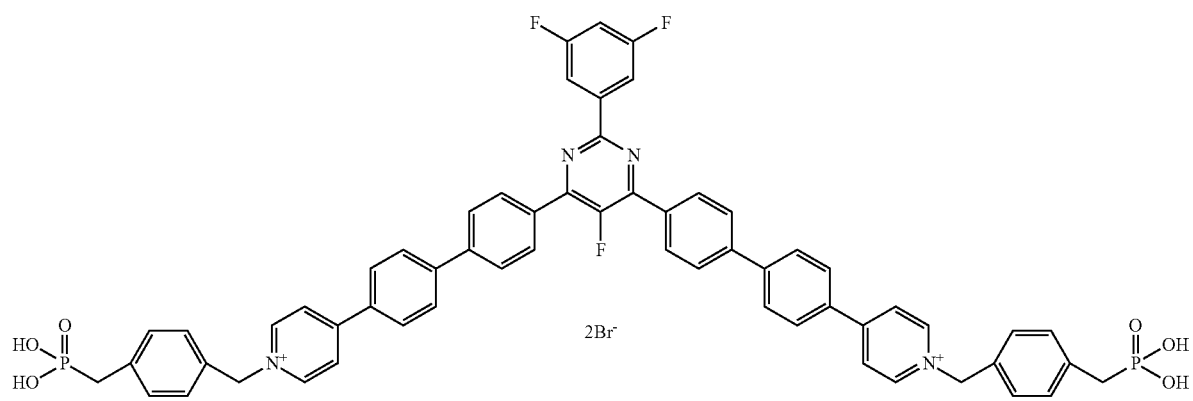

-continued
Electrochromic Compound (25)
Structural Formula (25)
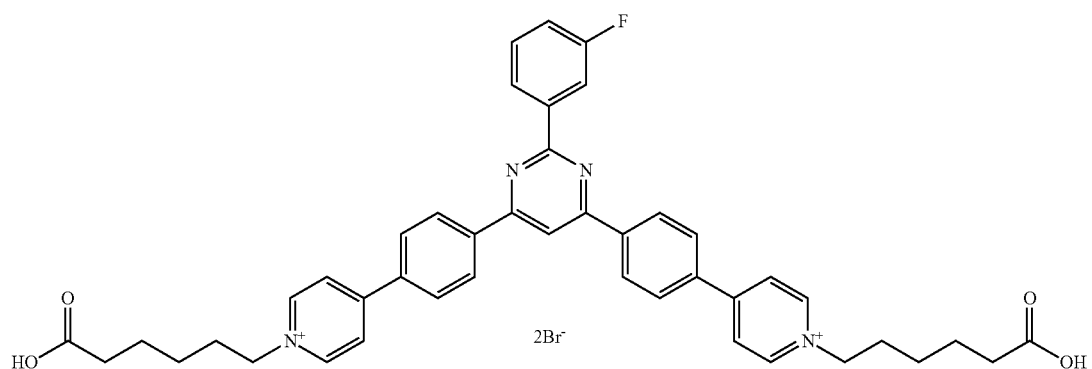
Electrochromic Compound (26)
Structural Formula (26)
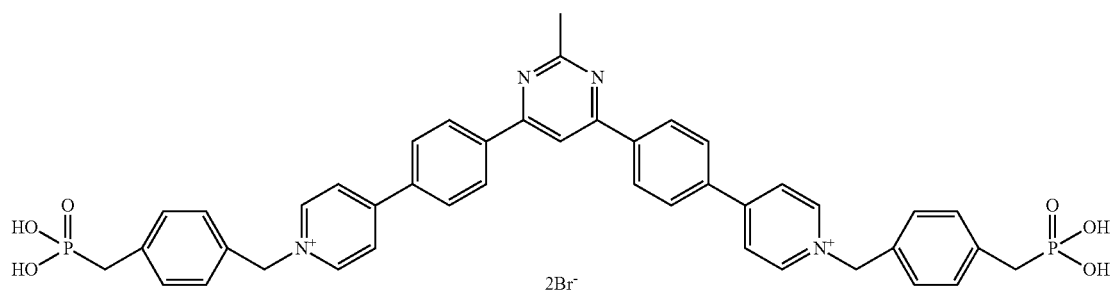
Electrochromic Compound (27)
Structural Formula (27)
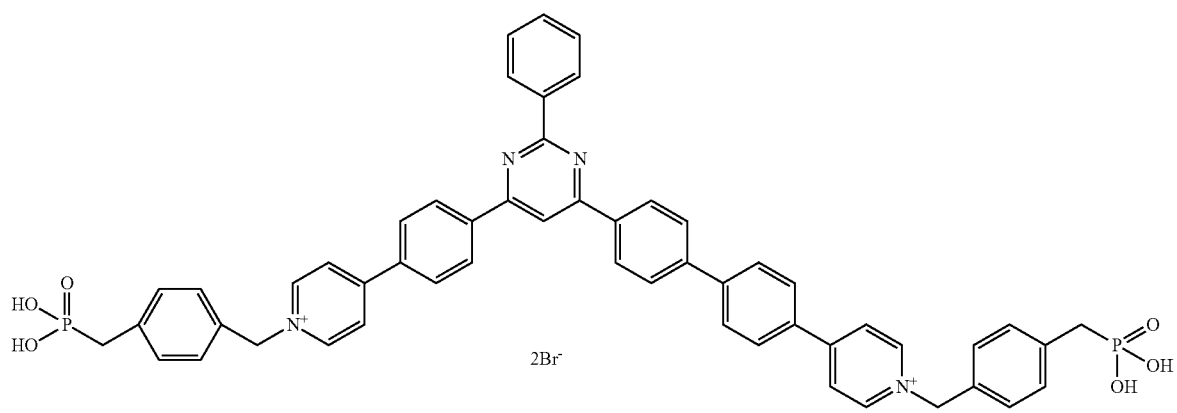

-continued
Electrochromic Compound (28)
Structural Formula (28)
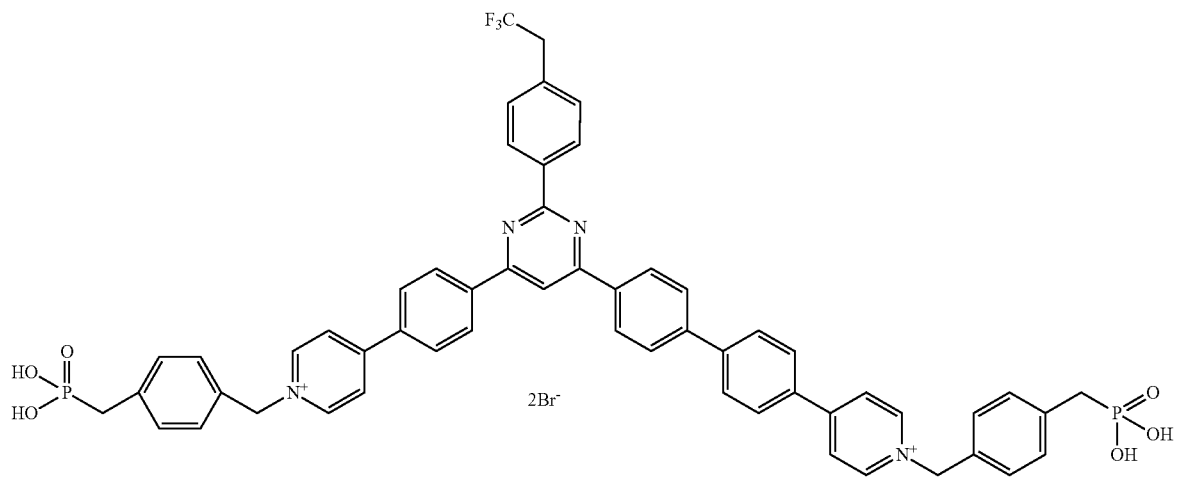
Electrochromic Compound (29)
Structural Formula (29)
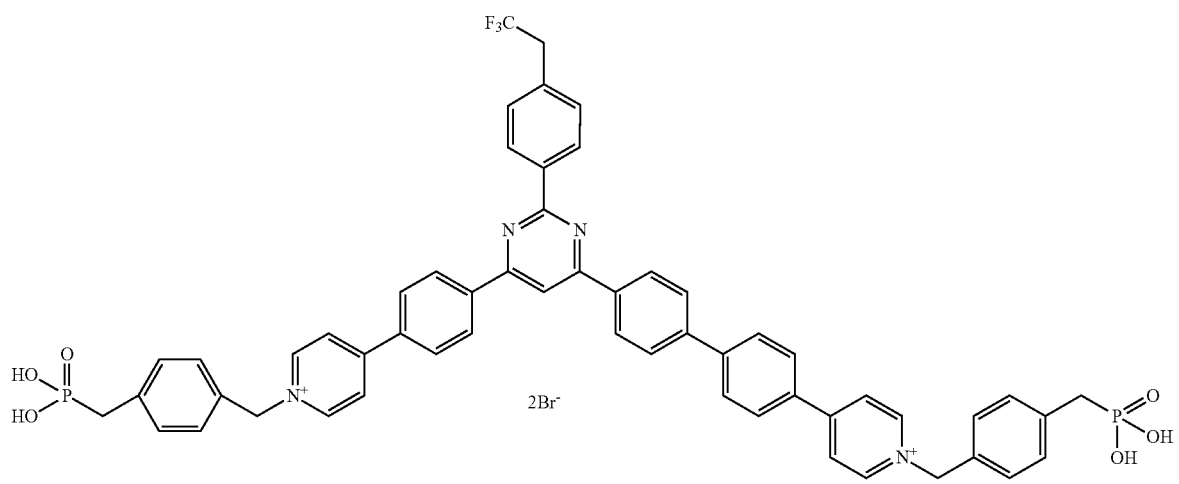
Electrochromic Compound (30)
Structural Formula (30)
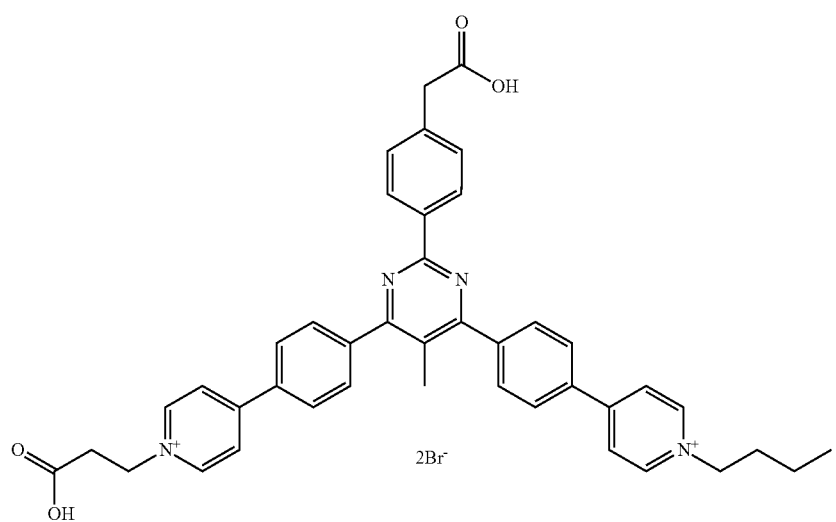

-continued
Electrochromic Compound (31)
Structural Formula (31)
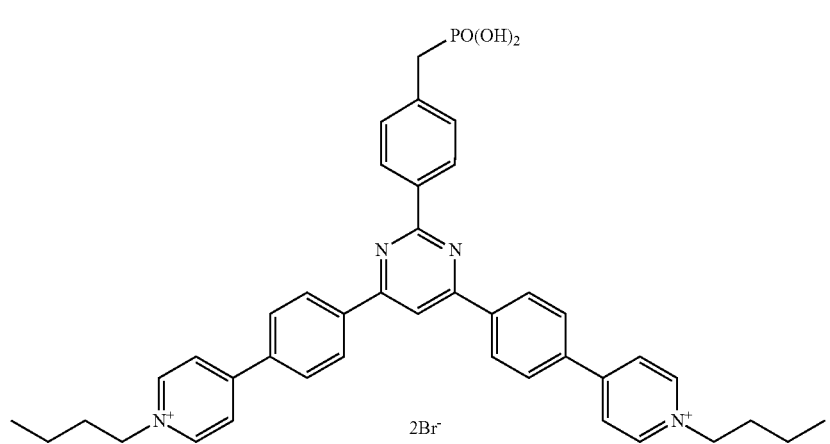
Electrochromic Compound (32)
Structural Formula (32)
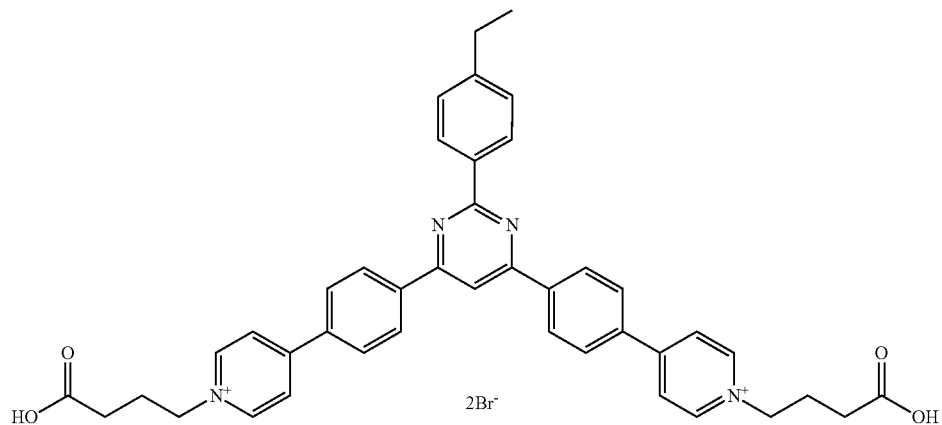
Electrochromic Compound (33)
Structural Formula (33)
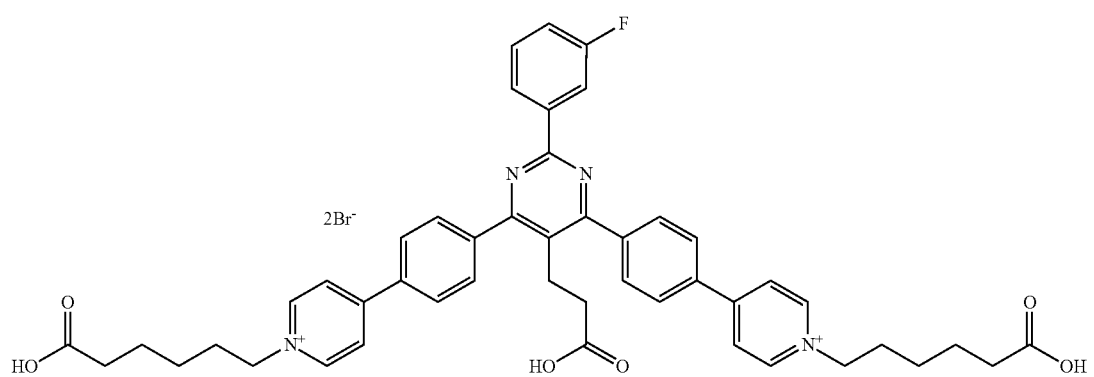

Electrochromic Compound (34)
Structural Formula (34)
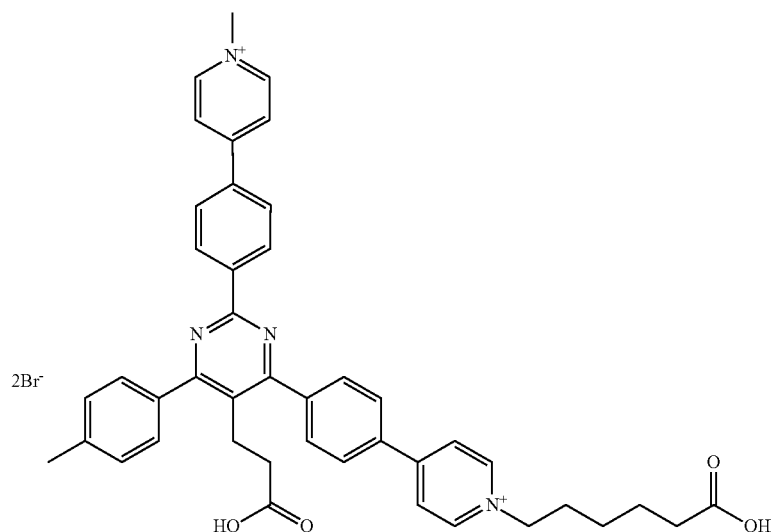
Electrochromic Compound (35)
Structural Formula (35)
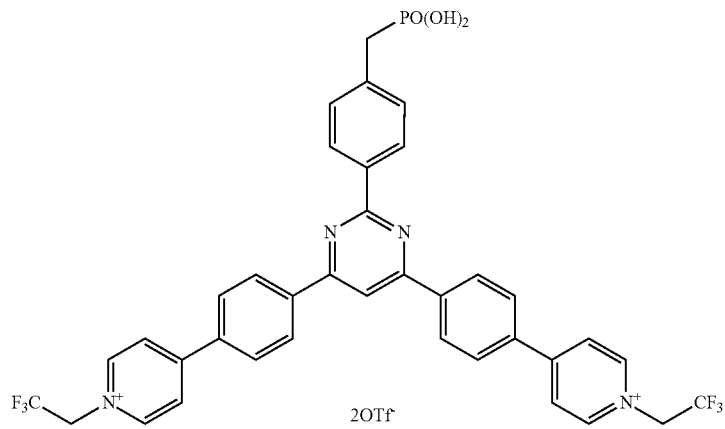
Electrochromic Compound (36)
Structural Formula (36)
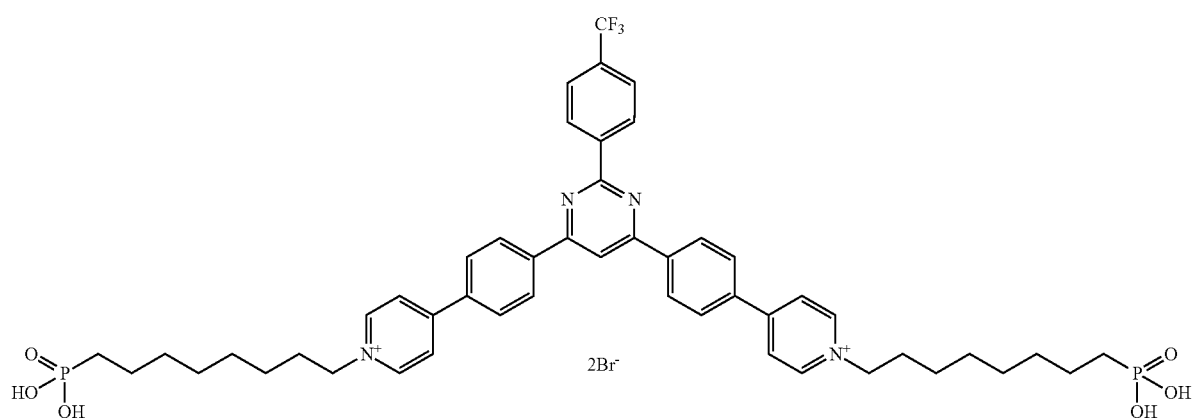

-continued
Electrochromic Compound (37)
Structural Formula (37)
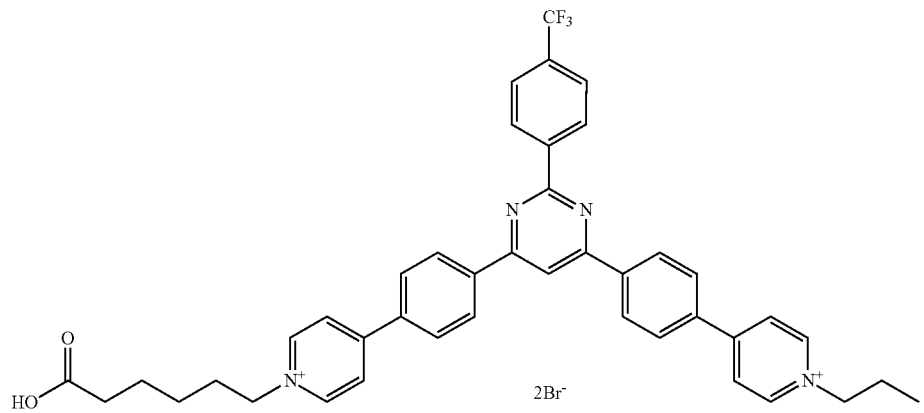
Electrochromic Compound (38)
Structural Formula (38)
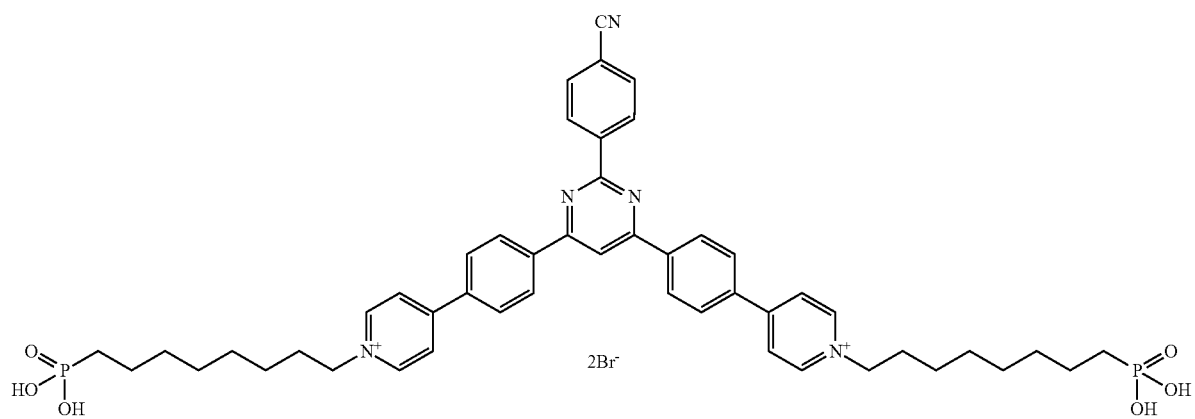
Electrochromic Compound (39)
Structural Formula (39)
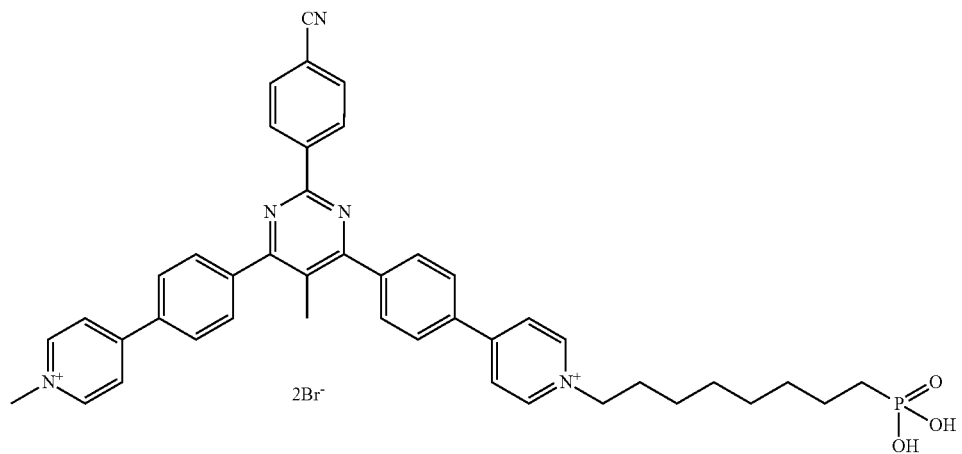

-continued
Electrochromic Compound (40)
Structural Formula (40)
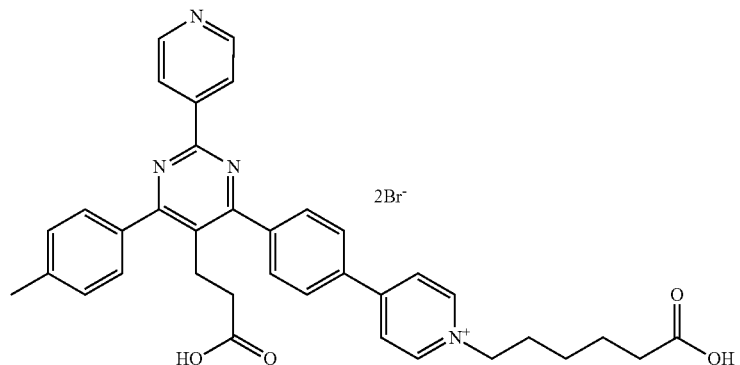
Electrochromic Compound (41)
Structural Formula (41)
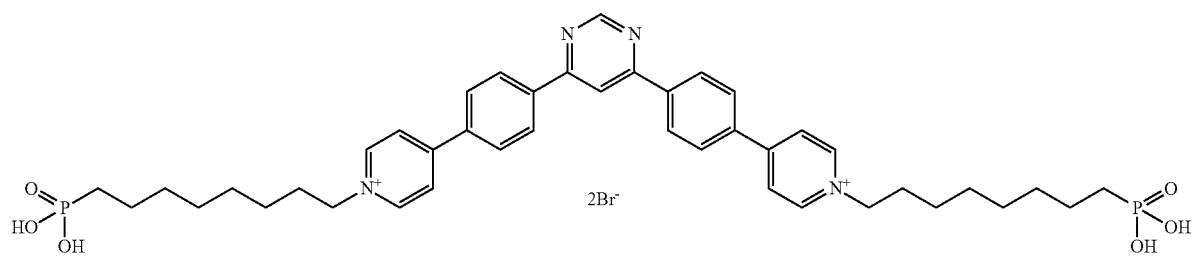
Electrochromic Compound (42)
Structural Formula (42)
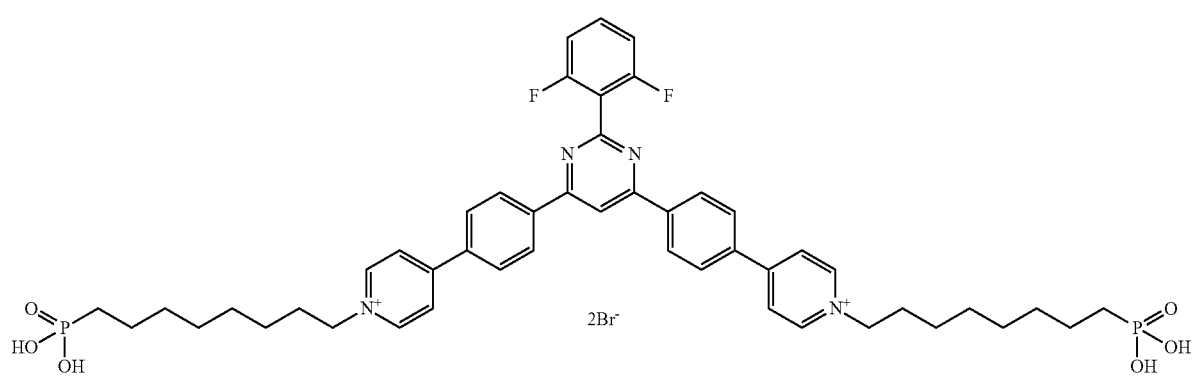

Electrochromic Compound (43)
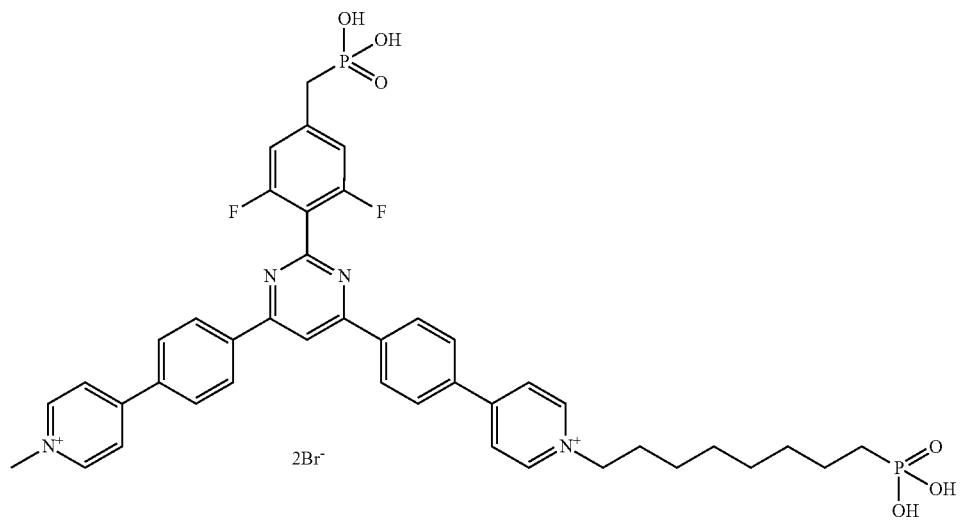
Structural Formula (43)
Electrochromic Compound (44)
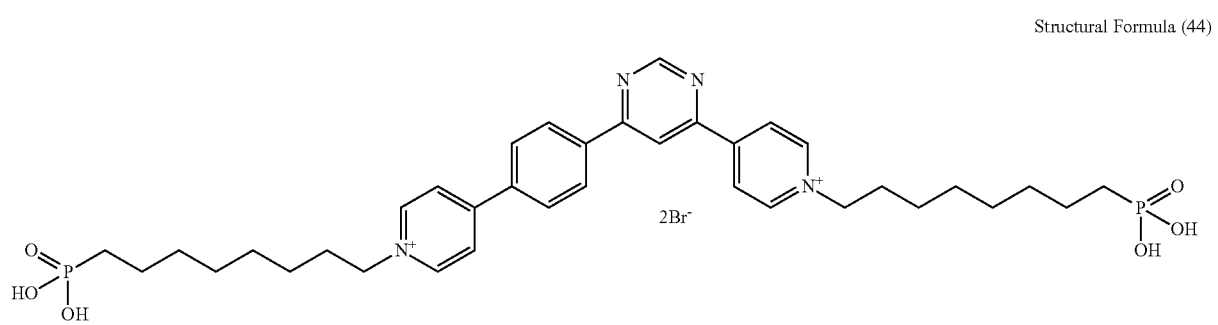
Structural Formula (44)
Electrochromic Compound (45)
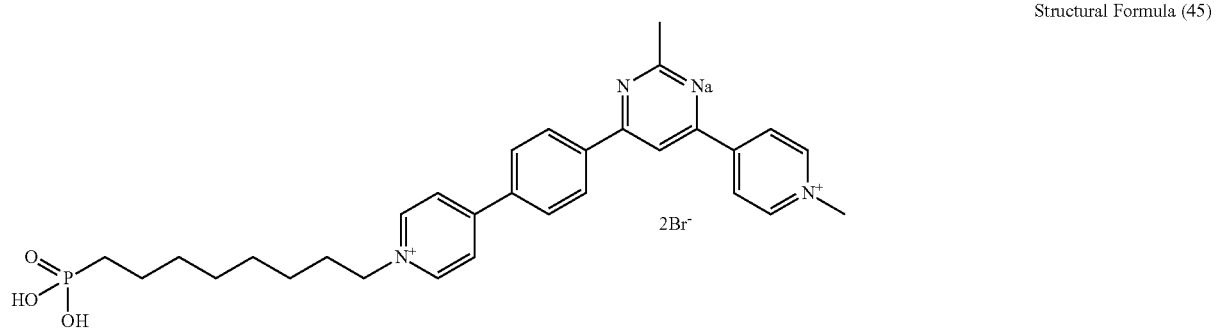
Structural Formula (45)
Electrochromic Compound (46)
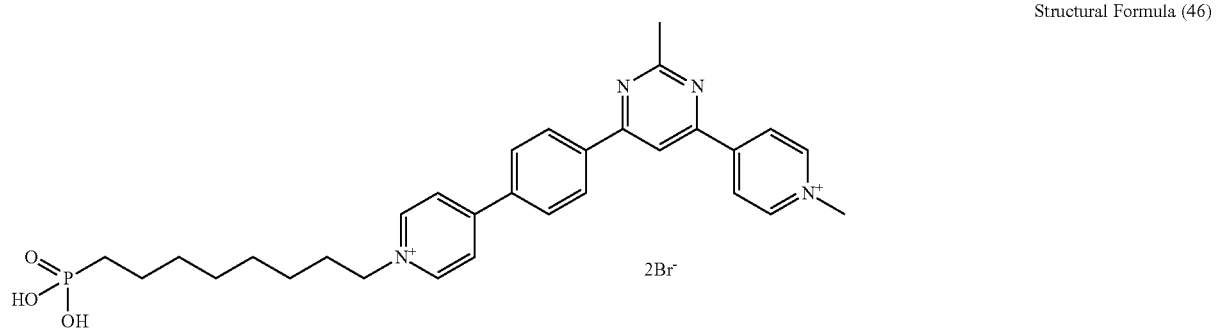
Structural Formula (46)

-continued
Electrochromic Compound (47)
Structural Formula (47)
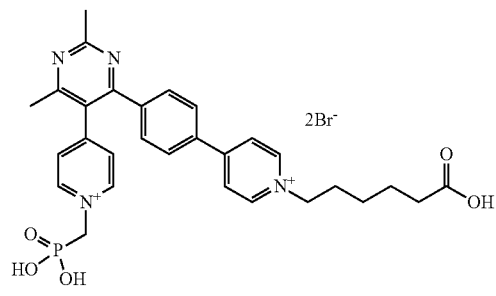
Electrochromic Compound (48)
Structural Formula (48)
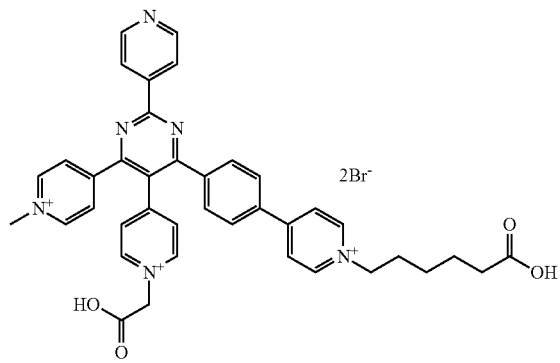
Electrochromic Compound (49)
Structural Formula (49)
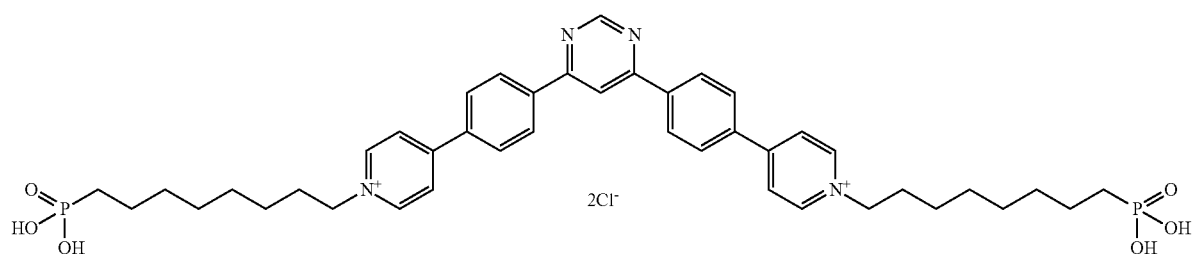
Electrochromic Compound (50)
Structural Formula (50)
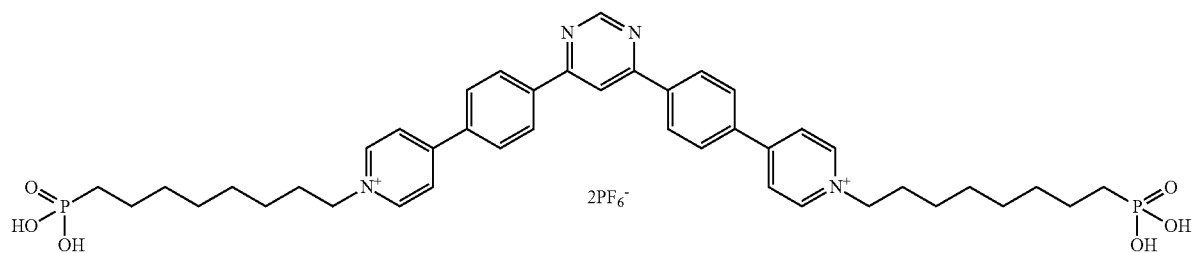
Electrochromic Compound (51)
Structural Formula (51)
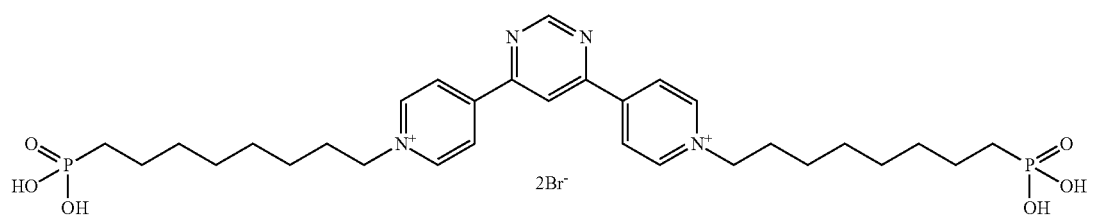

-continued
Electrochromic Compound (52)
Structural Formula (52)
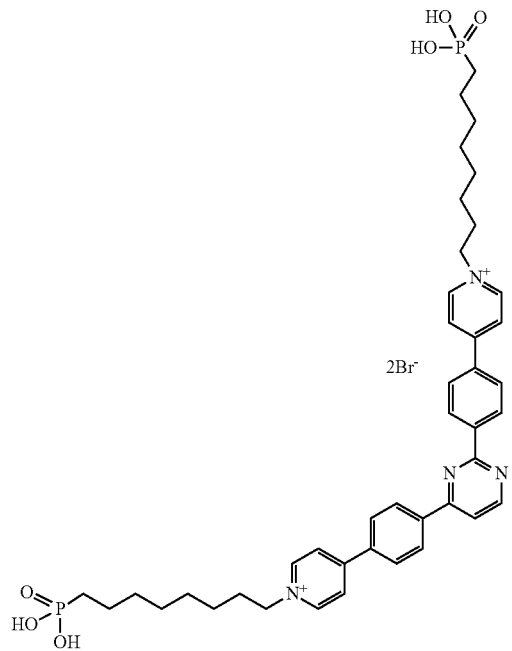
Electrochromic Compound (53)
Structural Formula (53)
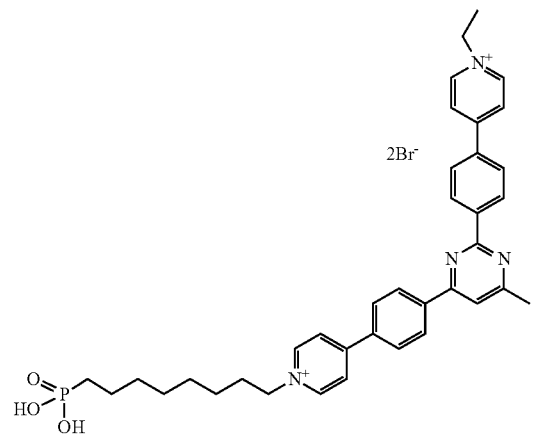
Electrochromic Compound (54)
Structural Formula (54)
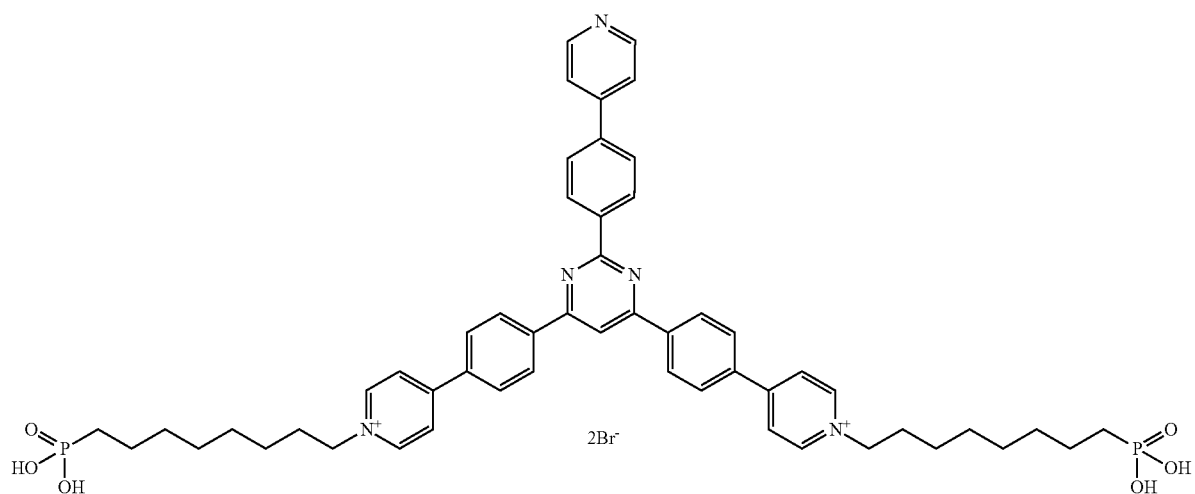

Electrochromic Compound (55)
Structural Formula (55)
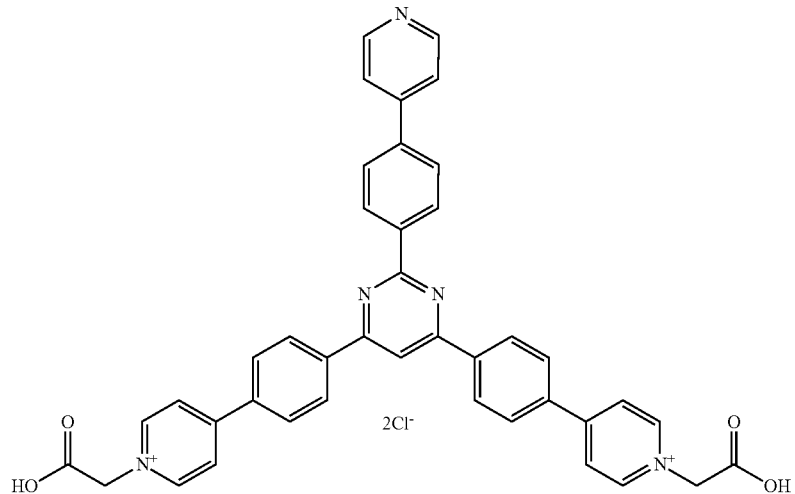
Electrochromic Compound (56)
Structural Formula (56)
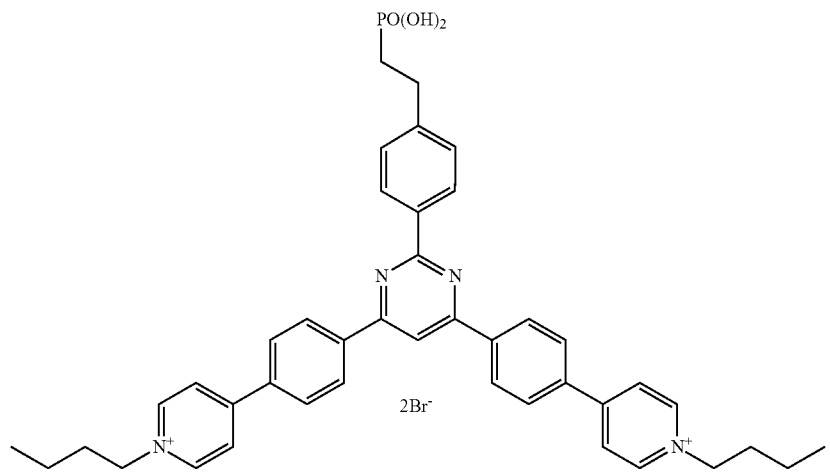
Electrochromic Compound (57)
Structural Formula (57)
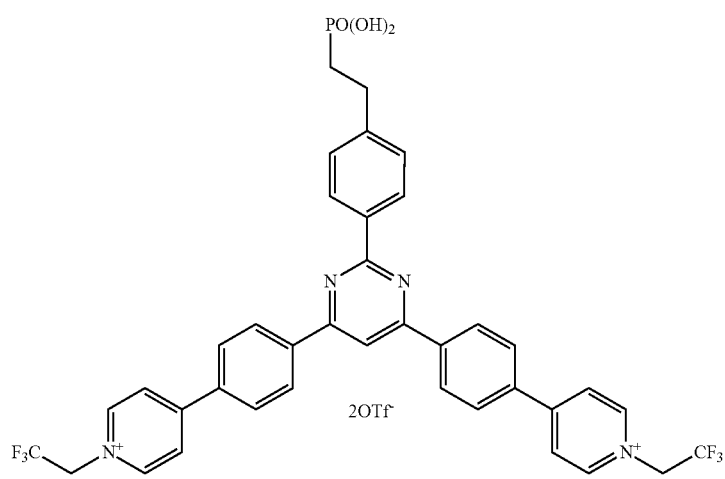

-continued
Electrochromic Compound (58)
Structural Formula (58)
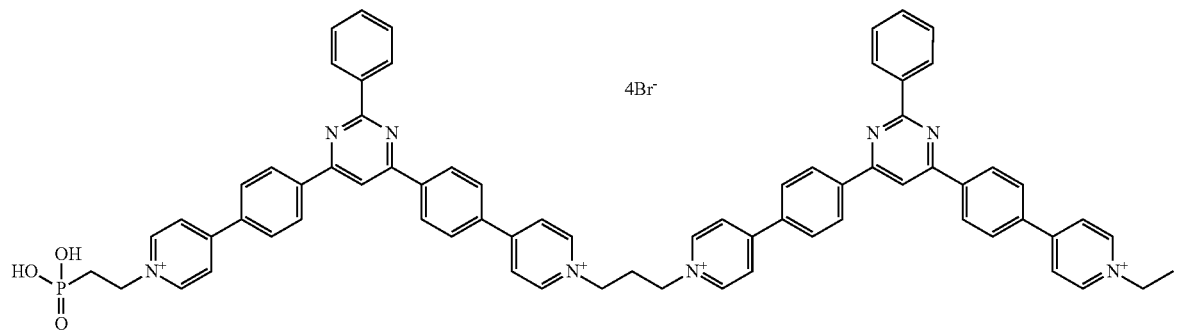
Electrochromic Compound (59)
Structural Formula (59)
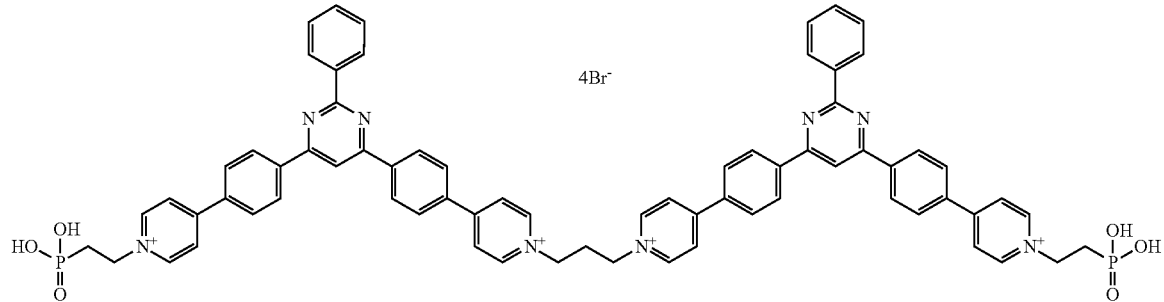
Electrochromic Compound (60)
Structural Formula (60)
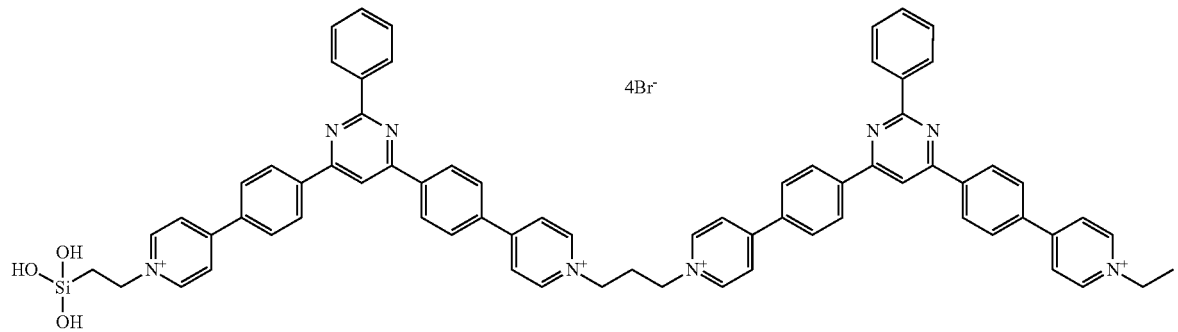
Electrochromic Compound (61)
Structural Formula (61)
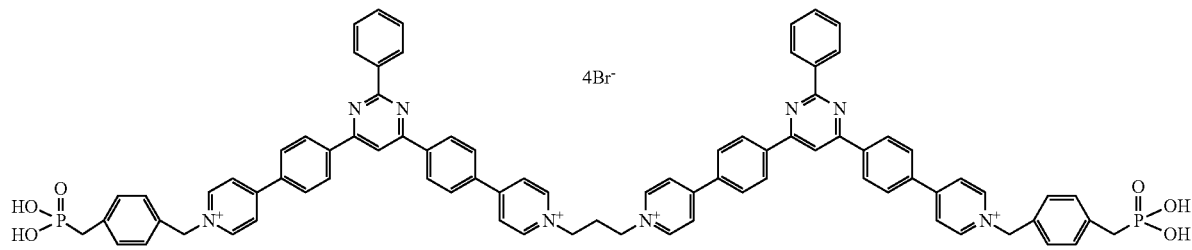

-continued
Electrochromic Compound (62)
Structural Formula (62)
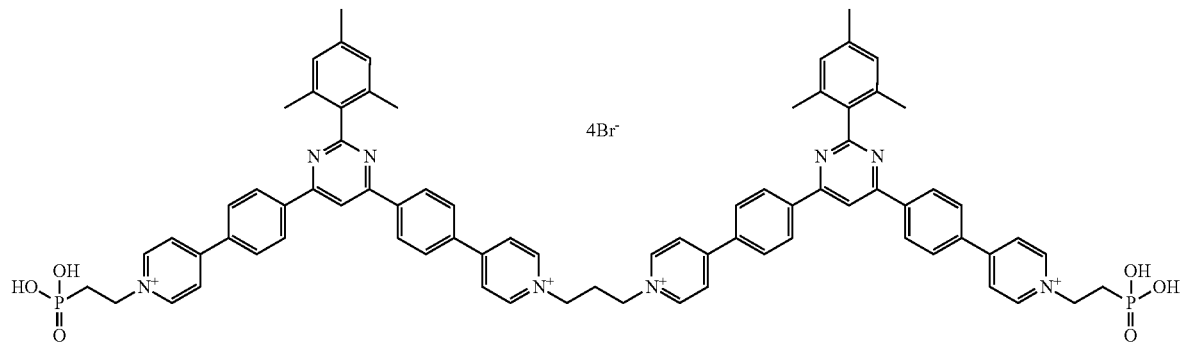
Electrochromic Compound (63)
Structural Formula (63)
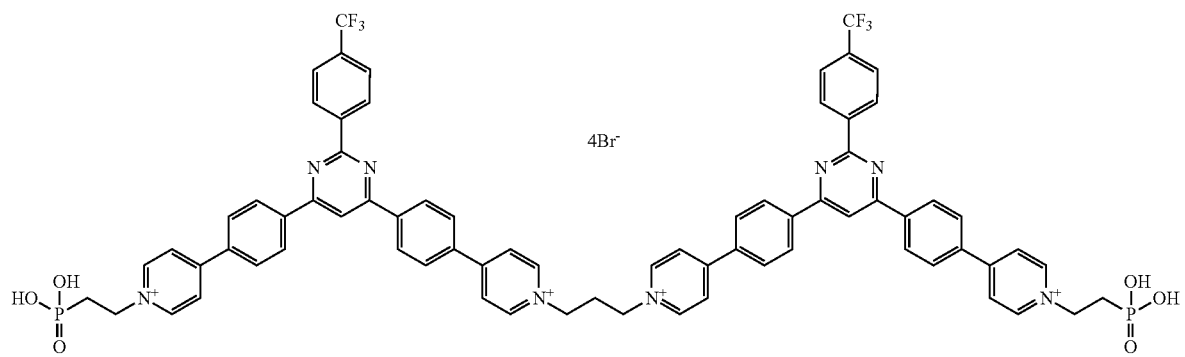
Electrochromic Compound (64)
Structural Formula (64)
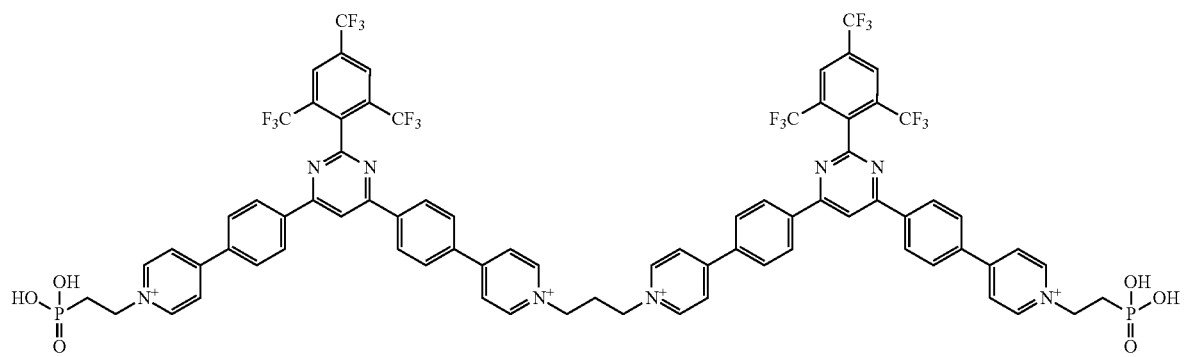
Electrochromic Compound (65)
Structural Formula (65)
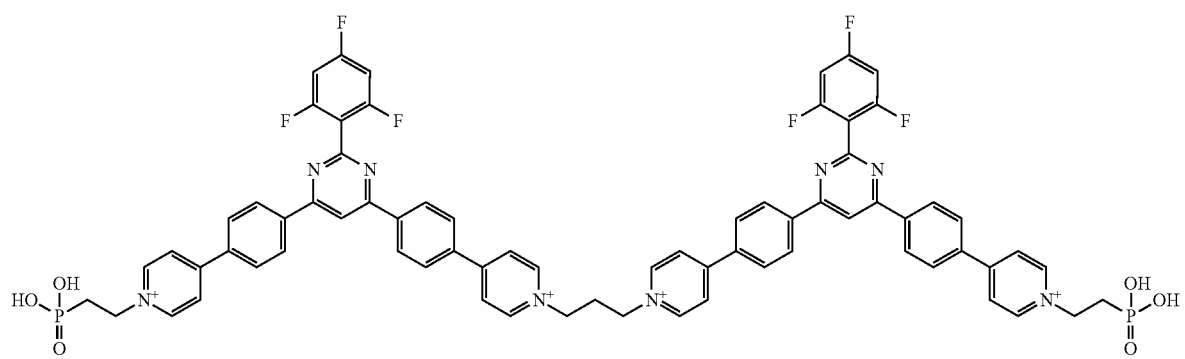

Electrochromic Compound (66)
Structural Formula (66)
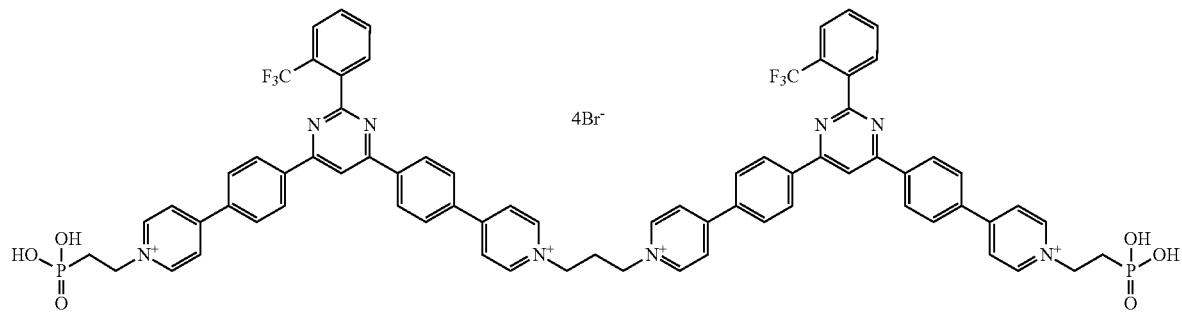
Electrochromic Compound (67)
Structural Formula (67)
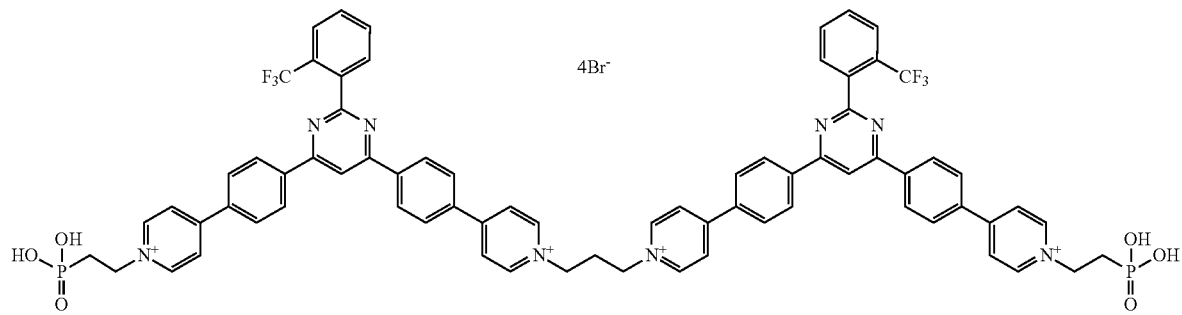
Electrochromic Compound (68)
Structural Formula (68)
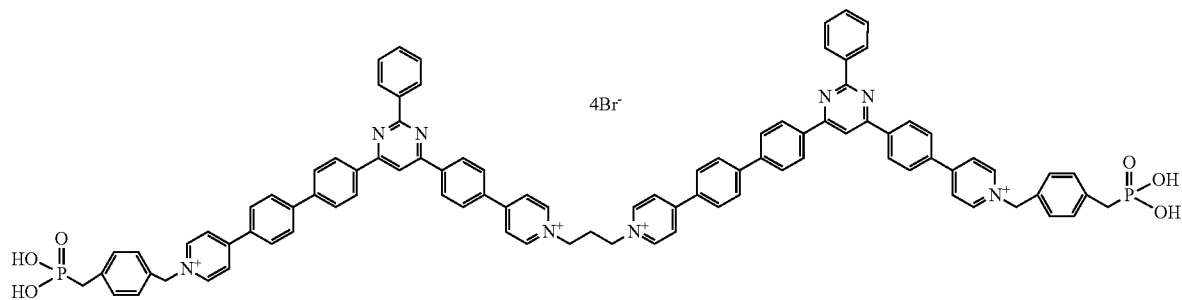
Electrochromic Compound (69)
Structural Formula (69)
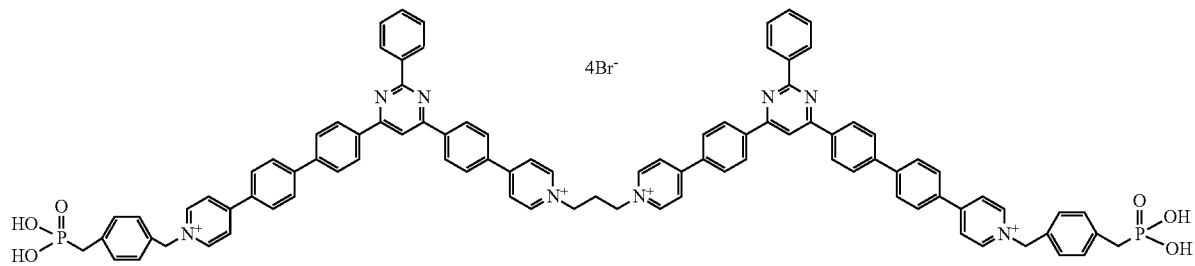

Electrochromic Compound (70)
Structural Formula (70)
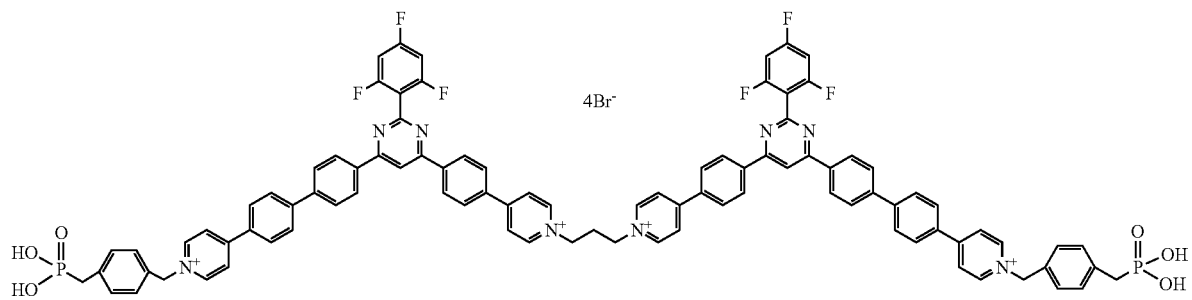
Electrochromic Compound (71)
Structural Formula (71)
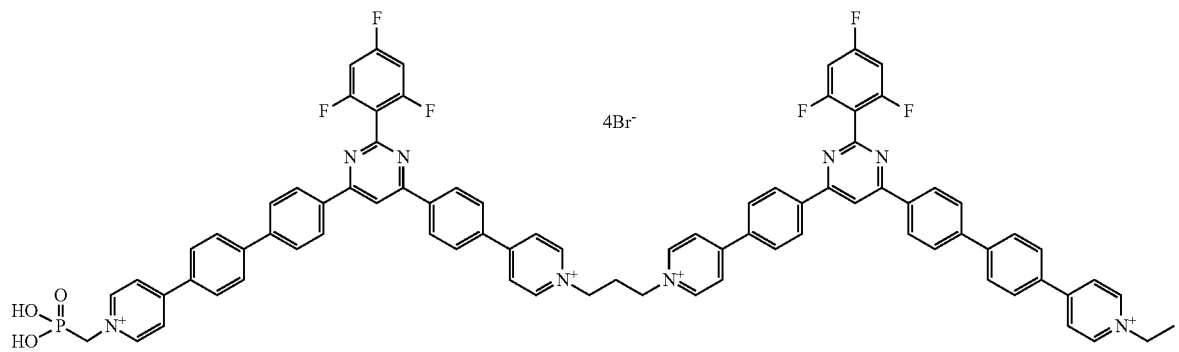
Electrochromic Compound (72)
Structural Formula (72)
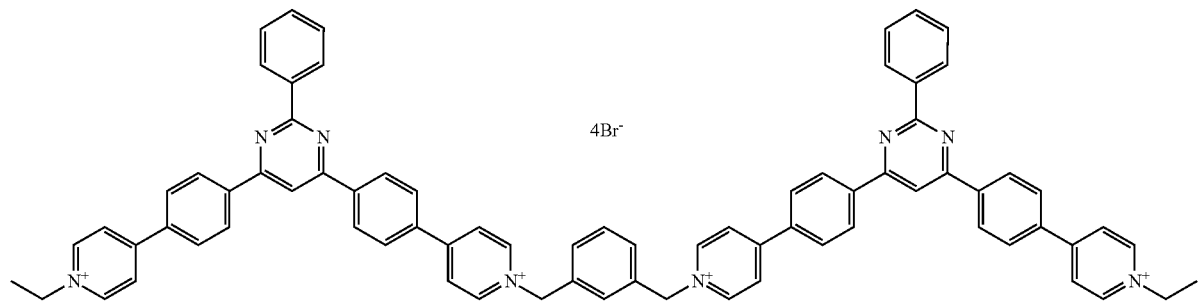
Electrochromic Compound (73)
Structural Formula (73)
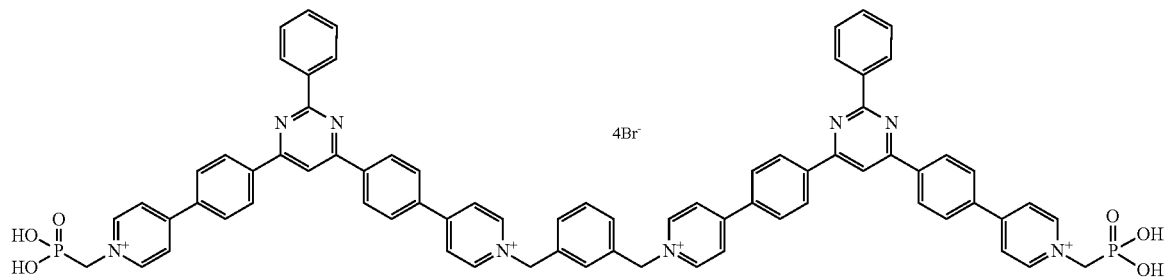

Electrochromic Compound (74)
Structural Formula (74)
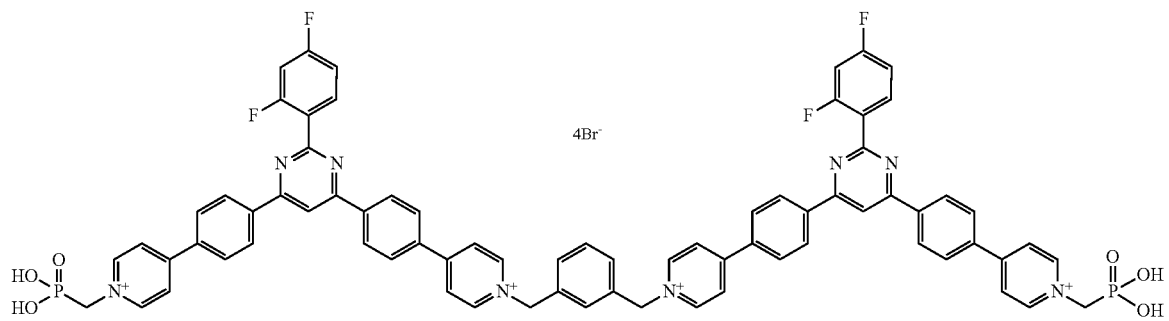
Electrochromic Compound (75)
Structural Formula (75)
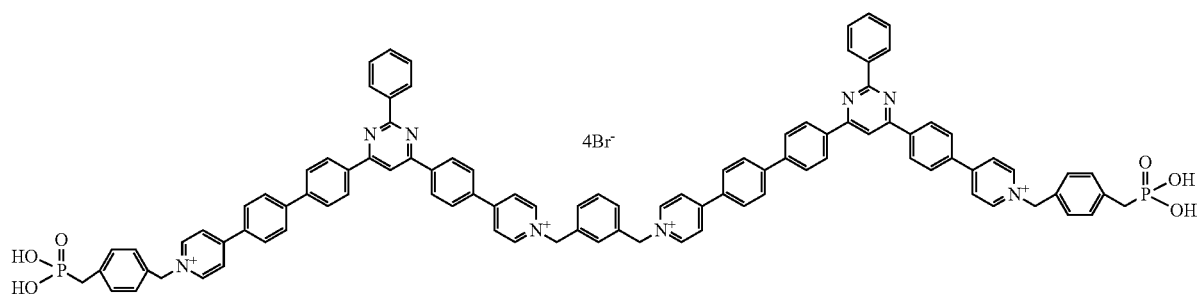
Electrochromic Compound (76)
Structural Formula (76)
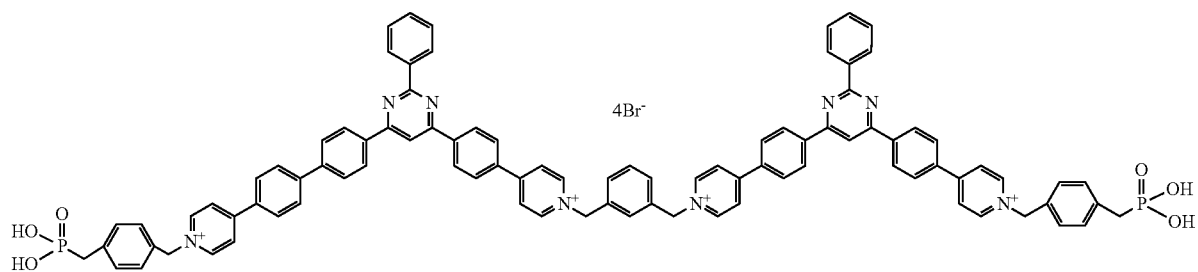
Electrochromic Compound (77)
Structural Formula (77)
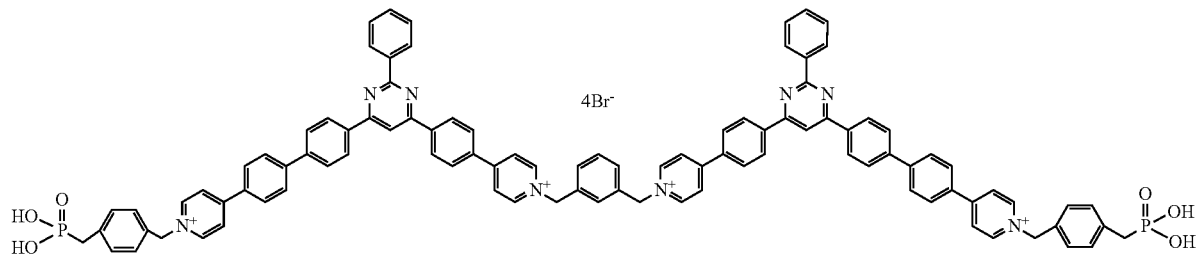

Electrochromic Compound (78)
Structural Formula (78)
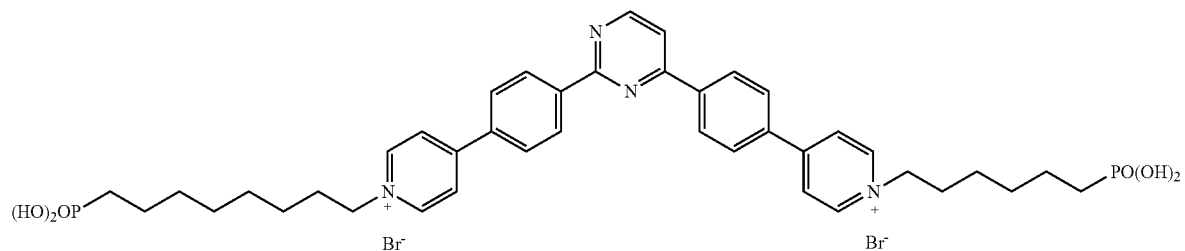
Electrochromic Compound (79)
Structural Formula (79)
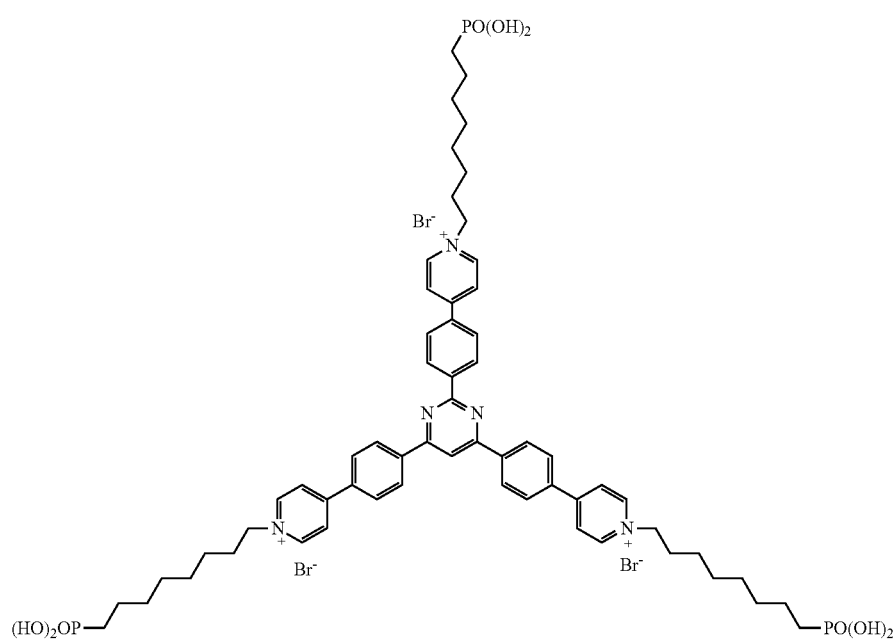

Electrochromic Compound (80)

Structural Formula (80)

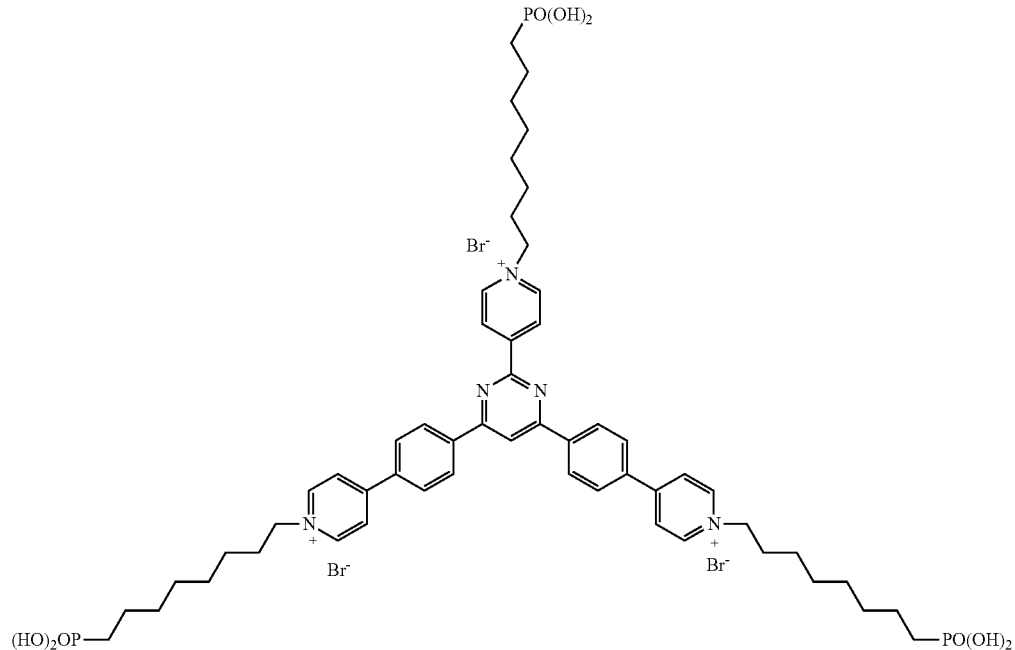

Next, a production method of the electrochromic compound of the present invention, which is represented by the general formula (III), is explained.

A method for synthesizing the electrochromic compound of the present invention is not particularly limited, and the electrochromic compound can be synthesized by various conventional coupling methods. In the case where the electrochromic compound represented by the general formula (III) is synthesized, one example of the synthesis method is a method where enone synthesized through aldol condensation and amidine are allowed to react to form a pyridine ring, followed by introducing the pyridine ring through an aryl-aryl coupling reaction, such as Suzuki coupling, and finally heating is performed in the presence of a halogenated product to quaternize the terminal pyridine.

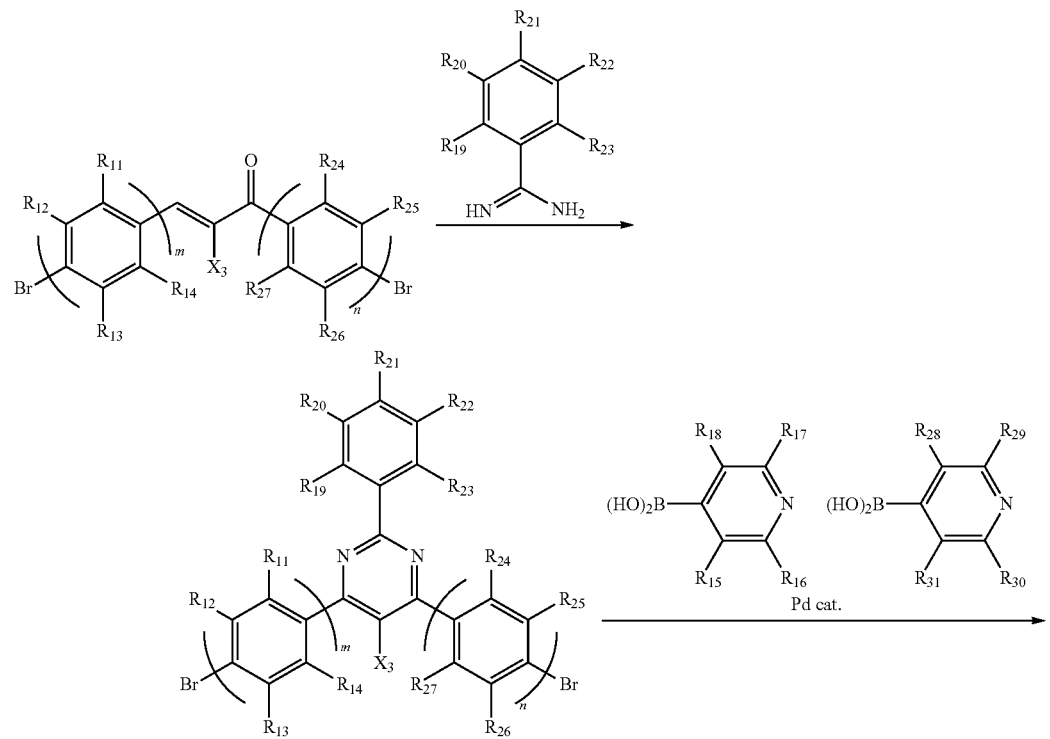

-continued

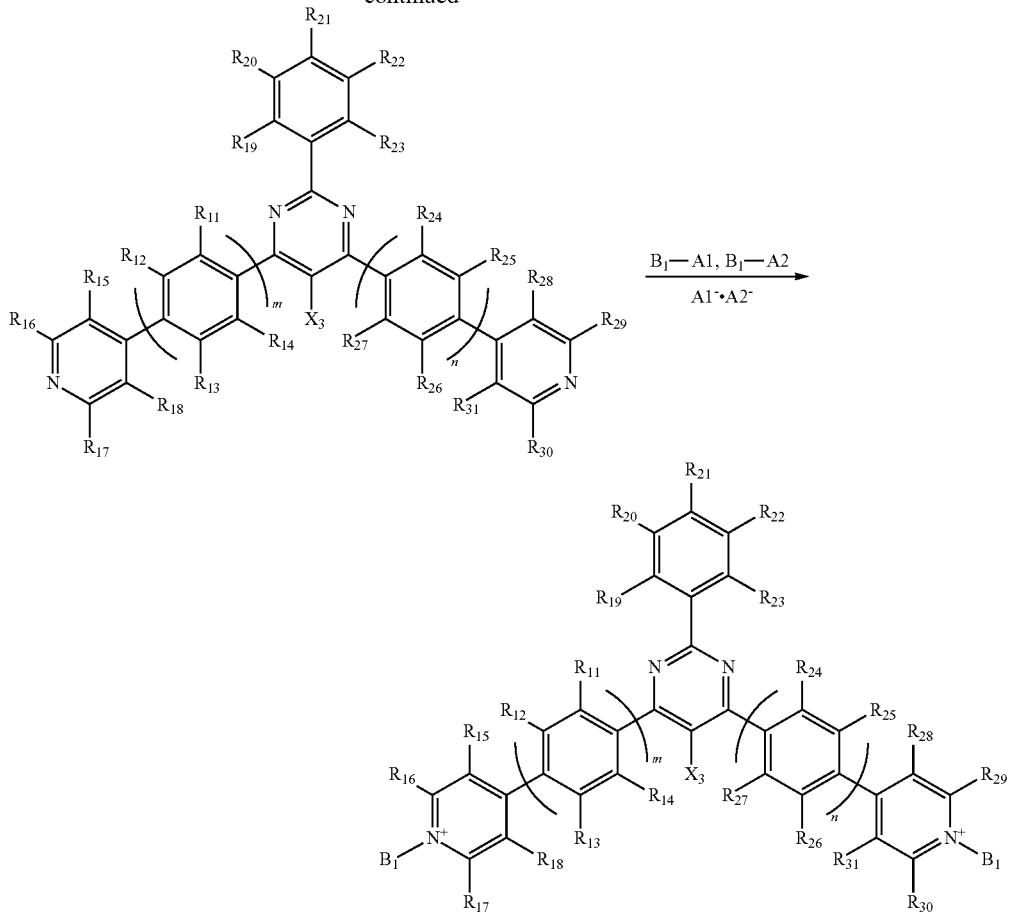

In the case where the electrochromic compound represented by the general formula (IV) is obtained, a quaternization reaction is performed using about 0.5-fold moles of a bifunctional compound, such as dihalogenated product to dimerize, and again, a quaternization reaction of a terminal pyridine ring is performed.

In the second embodiment, the electrochromic compound of the present invention is represented by the following general formula (Ia):

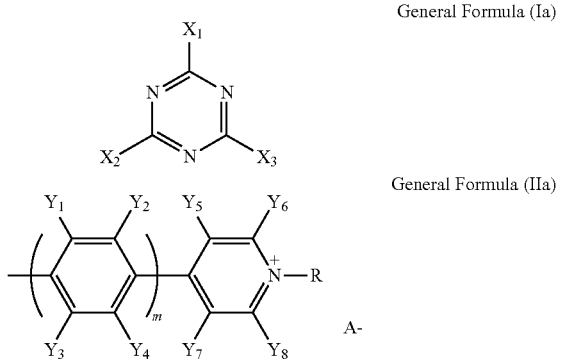

General Formula (Ia)

General Formula (IIa)

In the general formula (Ia), at least two of $X_1$, $X_2$, and $X_3$ have a structure represented by the general formula (IIa). In the case where two of them have a structure represented by the general formula (IIa), the rest, $X_1$, $X_2$, or $X_3$ is an aliphatic hydrocarbon group that may contain a functional group, an aromatic hydrocarbon group that may contain a functional group, or a hydrogen atom. $Y_1$ to $Y_8$ are each independently a hydrogen atom, or a monovalent group that may have a substituent. R is a substituted or unsubstituted monovalent group that may have a functional group. m is any of 0 to 3. $A^-$ is a monovalent anion. The structures of $Y_1$ to $Y_8$, m, and $A^-$ in the general formula (IIa) that is any of $X_1$, $X_2$, or $X_3$ of the general formula (Ia) may be each independently different.

The monovalent groups represented with $Y_1$ to $Y_8$ in the general formula (IIa) are each independently a monovalent group selected from the group consisting of a hydrogen atom, a halogen atom, a hydroxyl group, a nitro group, a cyano group, a carboxyl group, a carbonyl group, an amide group, an aminocarbonyl group, a sulfonic acid group, a sulfonyl group, a sulfonamide group, an aminosulfonyl group, an amino group, an alkyl group, an alkenyl group, an alkynyl group, an aryl group, an alkoxy group, an aryloxy group, an alkylthio group, an arylthio group, and a heterocyclic group. These monovalent groups may have a substituent. Moreover, the monovalent group represented with R is a monovalent group selected from the group consisting of an alkyl group, an alkenyl group, an alkynyl group, and an aryl group, which may have a functional group. These monovalent groups may have a substituent. Examples of the carbonyl group, which may have a substituent, include an alkoxy carbonyl group, an aryloxy carbonyl group, an alkyl carbonyl group, and an aryl carbonyl group. Examples of the aminocarbonyl group, which may have a substituent, include a monoalkyl aminocarbonyl group, a dialkyl aminocarbonyl group, a monoaryl aminocarbonyl group, and a diaryl aminocarbonyl group. Examples of the sulfonyl group, which may have a substituent, include an alkoxy sulfonyl group, an aryloxy sulfonyl group, an alkyl sulfonyl group, and an aryl sulfonyl group. Examples of the aminosulfonyl group, which may have a substituent, include a monoalkyl aminosulfonyl group, a dialkyl aminosulfonyl group, a monoaryl aminosulfonyl group, and a diaryl aminosulfonyl group. Examples of the amino group, which may have a substituent, include a monoalkyl amino group, and a dialkyl amino group.

Specifically, examples of the monovalent groups represented with $Y_1$ to $Y_8$ in the general formula (IIa) include a hydrogen atom, a halogen atom, a hydroxyl group, a nitro group, a cyano group, a carboxyl group, a substituted or unsubstituted alkoxy carbonyl group, a substituted or unsubstituted aryloxy carbonyl group, a substituted or unsubstituted alkyl carbonyl group, a substituted or unsubstituted aryl carbonyl group, an amide group, a substituted or unsubstituted monoalkyl aminocarbonyl group, a substituted or unsubstituted dialkylaminocarbonyl group, a substituted or unsubstituted monoarylaminocarbonyl group, a substituted or unsubstituted diarylaminocarbonyl group, a sulfonic acid group, a substituted or unsubstituted alkoxysulfonyl group, a substituted or unsubstituted aryloxysulfonyl group, a substituted or unsubstituted alkylsulfonyl group, a substituted or unsubstituted arylsulfonyl group, a sulfone amide group, a substituted or unsubstituted monoalkylaminosulfonyl group, a substituted or unsubstituted dialkylaminosulfonyl group, a substituted or unsubstituted monoarylaminosulfonyl group, a substituted or unsubstituted diarylaminosulfonyl group, an amino group, a substituted or unsubstituted monoalkylamino group, a substituted or unsubstituted dialkylamino group, a substituted or unsubstituted alkyl group, a substituted or unsubstituted alkenyl group, a substituted or unsubstituted alkynyl group, a substituted or unsubstituted aryl group, a substituted or unsubstituted alkoxy group, a substituted or unsubstituted aryloxy group, a substituted or unsubstituted alkylthio group, a substituted or unsubstituted arylthio group, and a substituted or unsubstituted heterocyclic group. Examples of the monovalent group represented with B include an alkyl group that may have a functional group, an alkenyl group that may have a functional group, an alkynyl group that may have a functional group, and an aryl group that may have a functional group. These monovalent groups may have a substituent.

Owing to the monovalent groups of $Y_1$ to $Y_8$, solubility to a solvent is provided to an electrochromic compound, and therefore a production process of an element becomes easy. On the other hand, these groups may lower stability, such as heat resistance and light resistance. Therefore, preferred is a hydrogen atom, a halogen atom, or a substituent having 6 or fewer carbon atoms.

$A^-$ is a monovalent anion, and is not particularly limited as long as it stably forms a pair with a cation site, but preferred is Br ion ($Br^-$), Cl ion ($Cl^-$), $ClO_4$ ion ($ClO_4^-$), $PF_6$ ion ($PF_6^-$), $BF_4$ ion ($BF_4^-$), or trifluoromethane sulfonate ion ($CF_3SO_3^-$).

The electrochromic compound of the present invention has a structure where two or three of $X_1$ to $X_3$ of the general formula (I) are each a structure represented by the general formula (II). The electrochromic compound colors in black in the cases where two of $X_1$ to $X_3$ of the general formula (I) are each a structure represented by the general formula (II), or three of them. The case where two of $X_1$ to $X_3$ of the general formula (I) are each a structure represented by the general formula (II) is preferable, because a resulting electrochromic compound has high solubility, and therefore a production process of an element becomes easy.

The electrochromic compound of the present invention preferably contains a functional group capable of directly or indirectly bonding to a hydroxyl group. A structure of the functional group capable of directly or indirectly bonding to a hydroxyl group is not limited, as long as it is a functional group capable of directly or indirectly bonding to a hydroxyl group through a hydrogen bond, absorption, or a chemical reaction. Preferred examples thereof include: a phosphonic acid group; a phosphoric acid group; a silyl group (or a silanol group), such as a trichlorosilyl group, a trialkoxysilyl group, a monochlorosilyl group, and a monoalkoxysilyl group; and a carboxyl group. The trialkoxy silyl group is preferably a triethoxysilyl group, a trimethoxysilyl group. Among them, particularly preferred are a phosphonic acid group or a silyl group (a trialkoxysilyl group or a trihydroxysilyl group) having a strong bonding force to an electroconductive or semiconductive nano structure.

The position of the functional group capable of directly or indirectly bonding to a hydroxyl group is most preferably the side of R in the general formula (IIa). In the structure where a group represented by the general formula (IIa) are introduced in two selected from $X_1$, $X_2$, and $X_3$ in the general formula (Ia), moreover, the functional group capable of directly or indirectly bonding to a hydrogen group may be introduced in the remaining of $X_1$, $X_2$, and $X_3$. Of course, not only one, but also two or three functional groups each capable of directly or indirectly bonding to a hydroxyl group may be introduced.

Specific examples of the electrochromic compound of the present invention according to the second embodiment are listed as the following structural formulae (3) to (29), but the electrochromic compound of the present invention is not limited to these structural formulae.

Structural Formula (3)
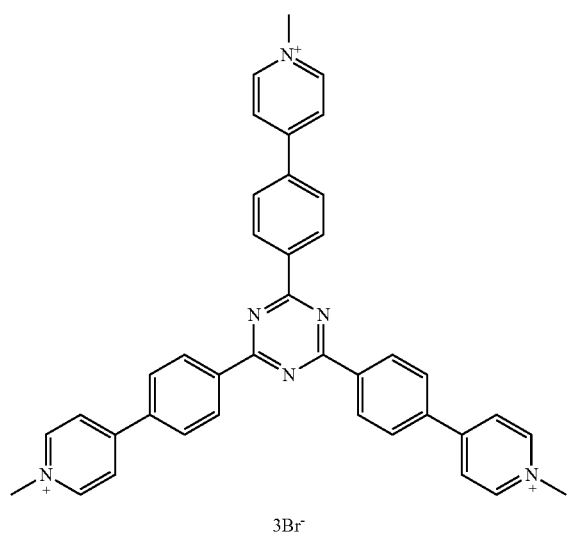
3Br⁻
Structural Formula (4)
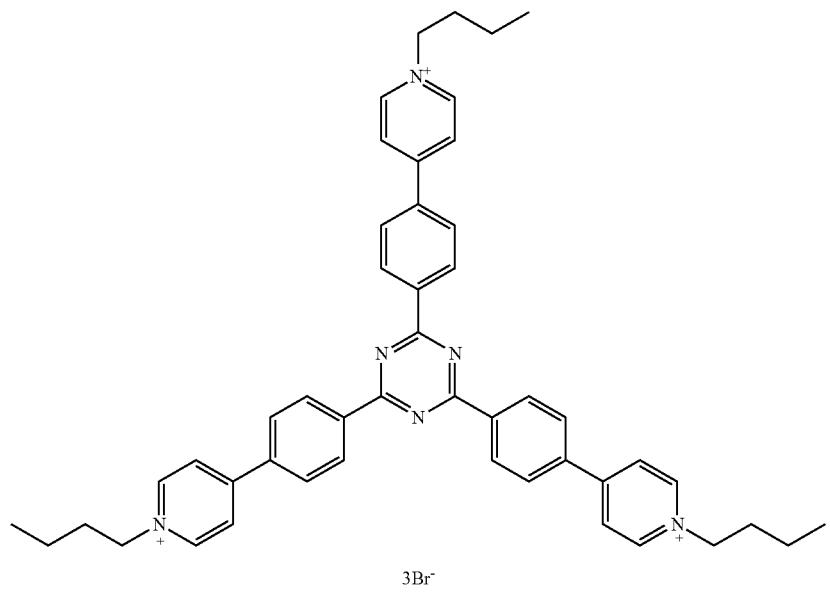
3Br⁻
Structural Formula (5)
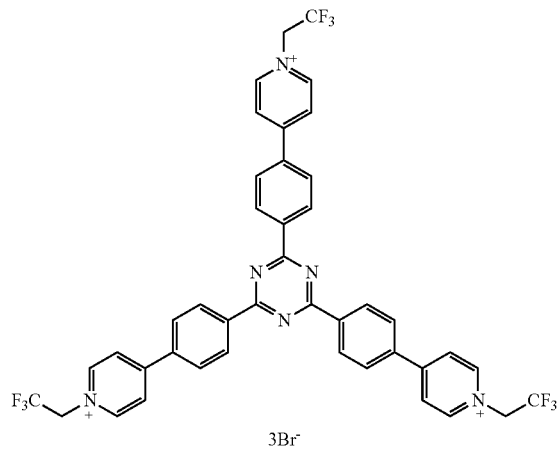
3Br⁻
Structural Formula (6)
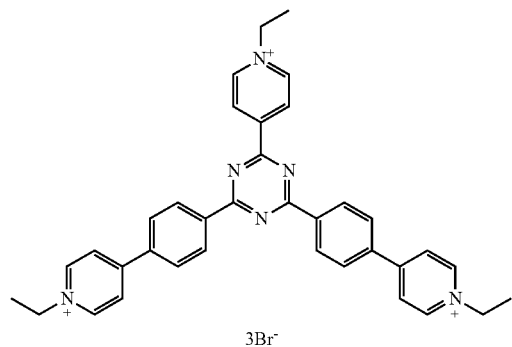
3Br⁻

Structural Formula (7)
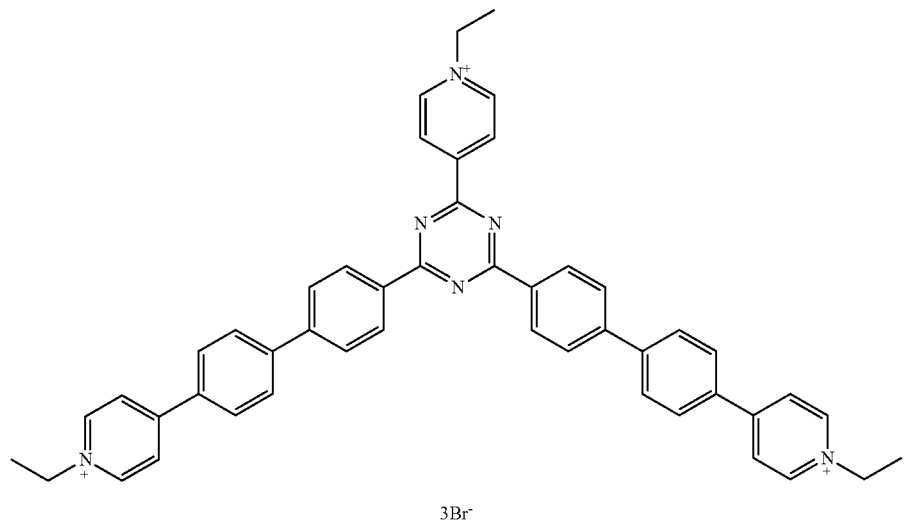
Structural Formula (8)
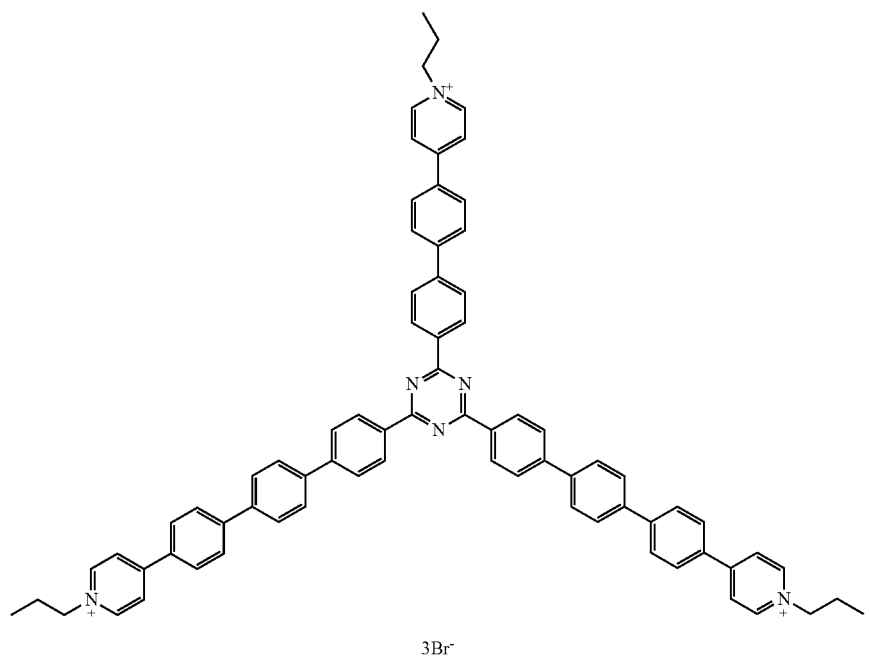

Structural Formula (9)
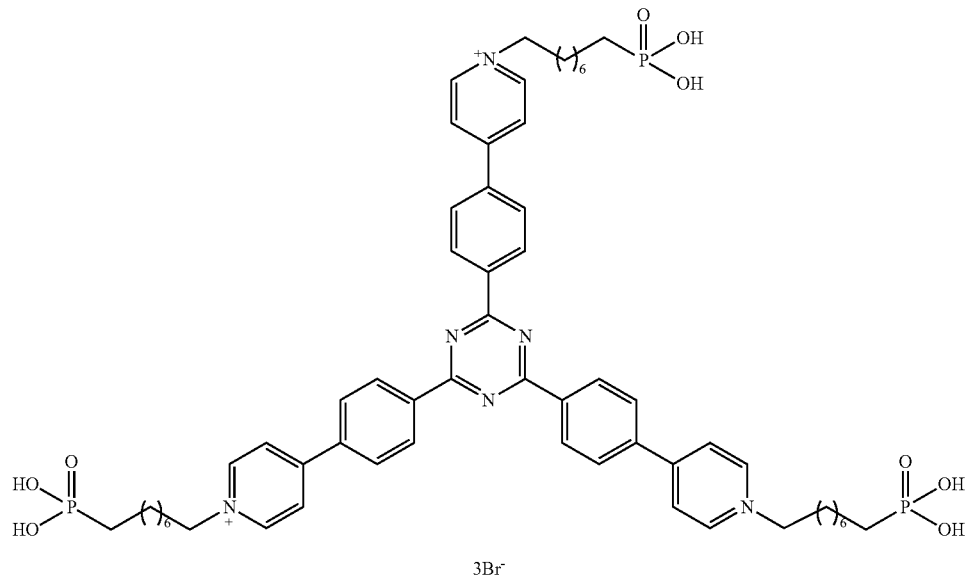
3Br⁻
Structural Formula (10)
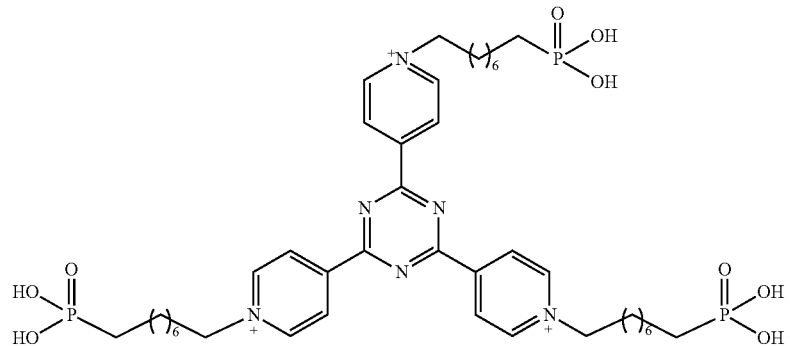
3Br⁻
Structural Formula (11)
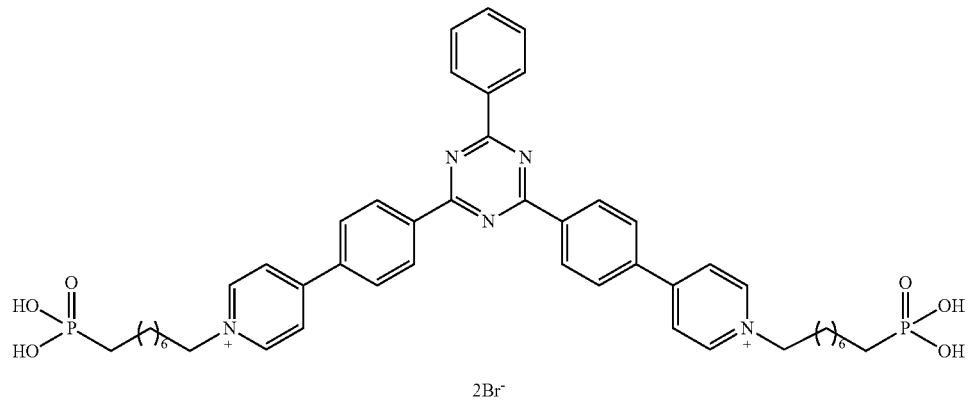
2Br⁻

-continued
Structural Formula (12)
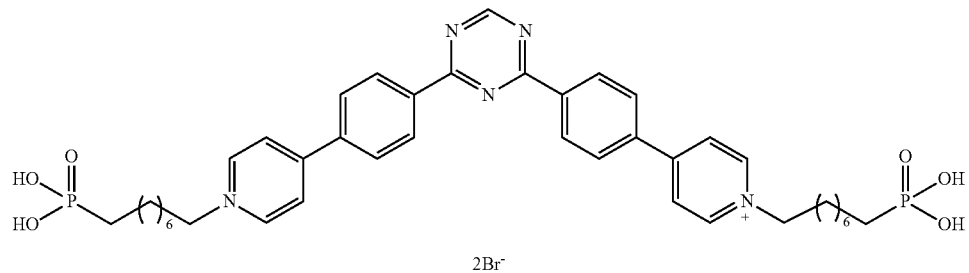
2Br⁻
Structural Formula (13)
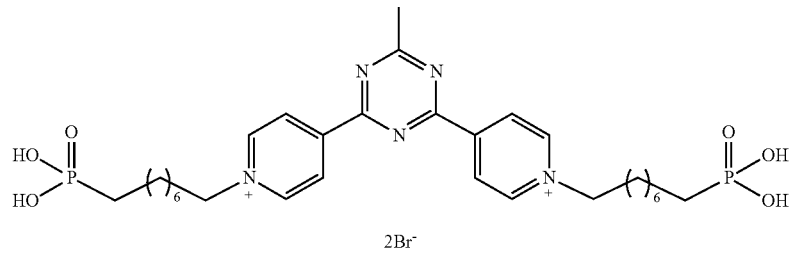
2Br⁻
Structural Formula (14)
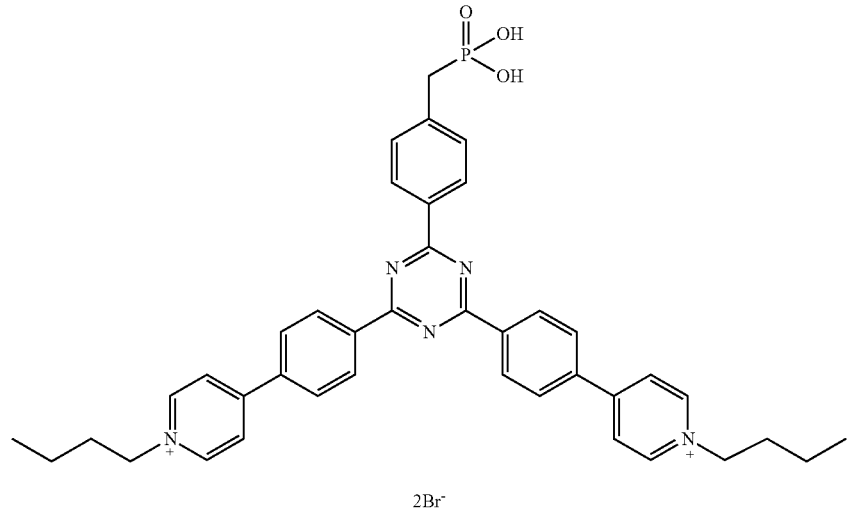
2Br⁻
Structural Formula (15)
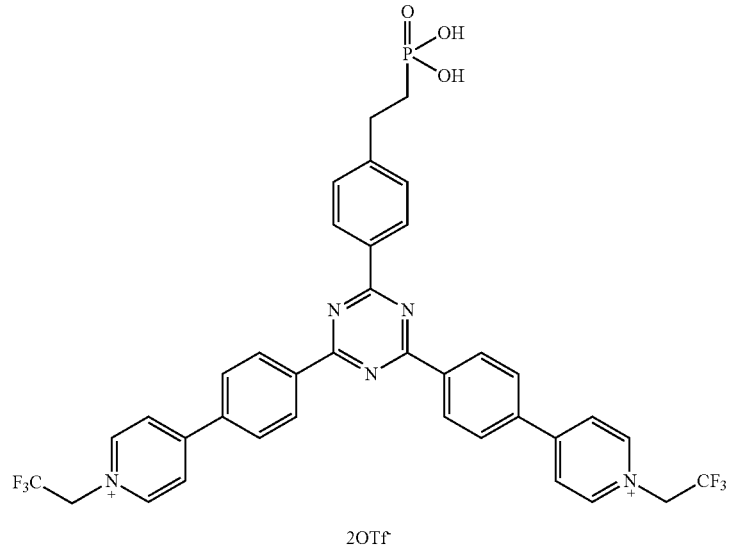
2OTf⁻

Structural Formula (16)
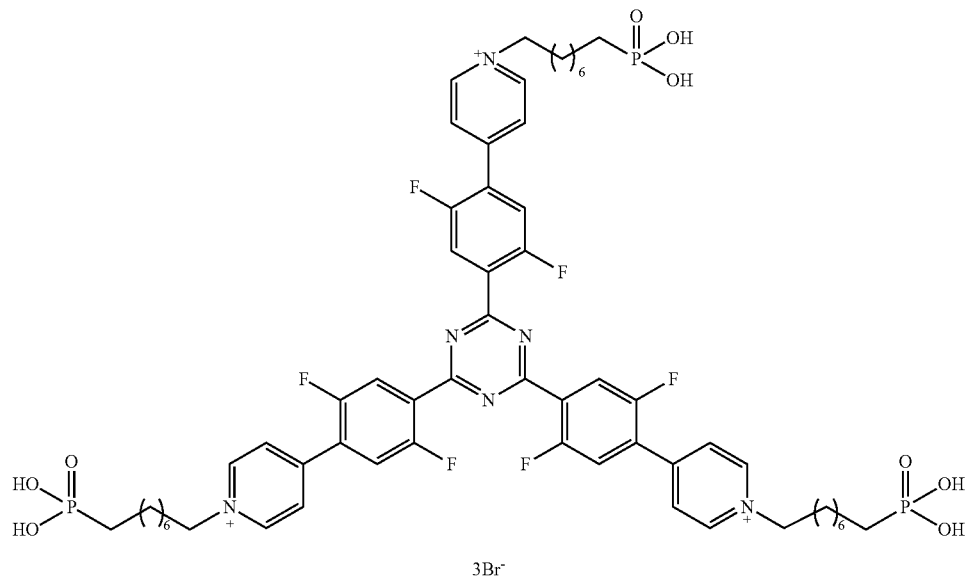
Structural Formula (17)
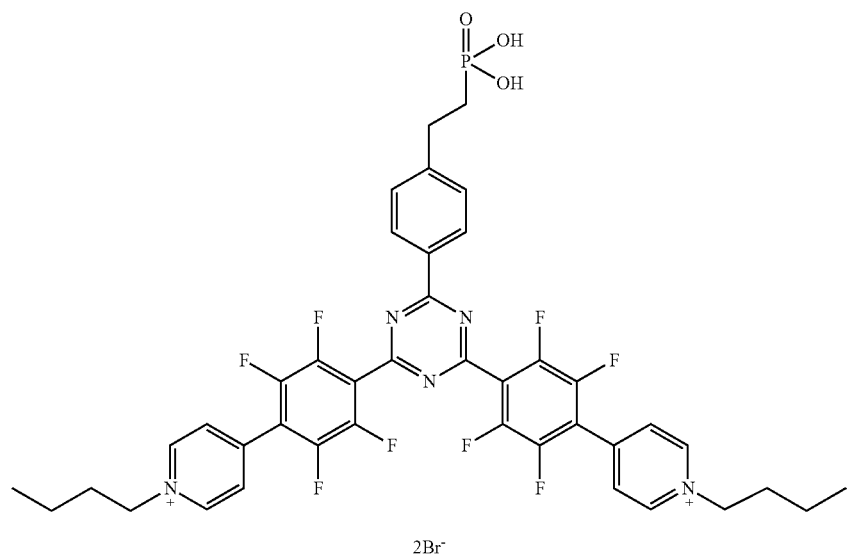
Structural Formula (18)
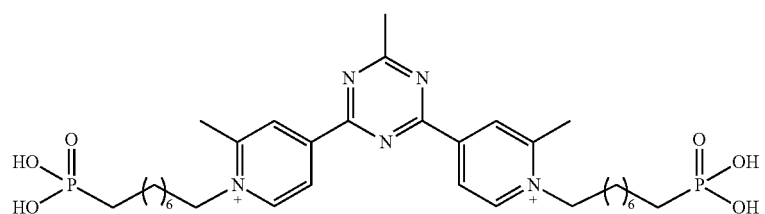

Structural Formula (19)
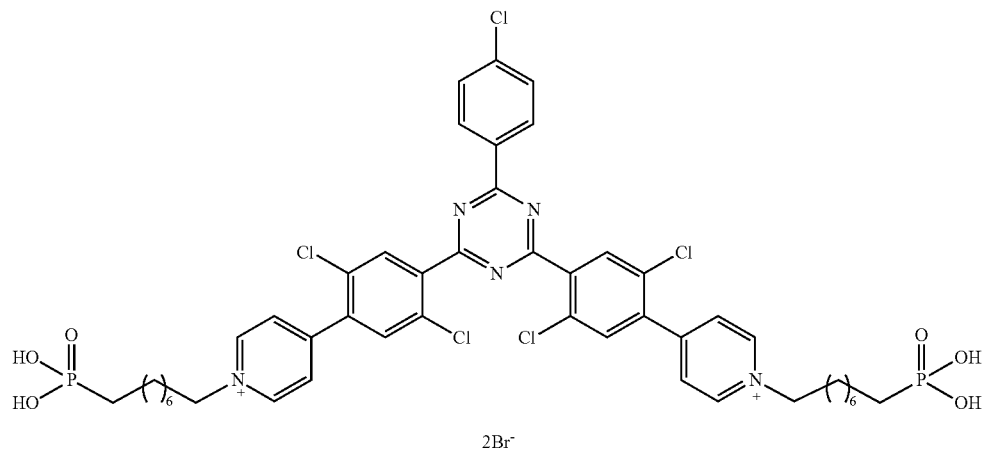
Structural Formula (20)
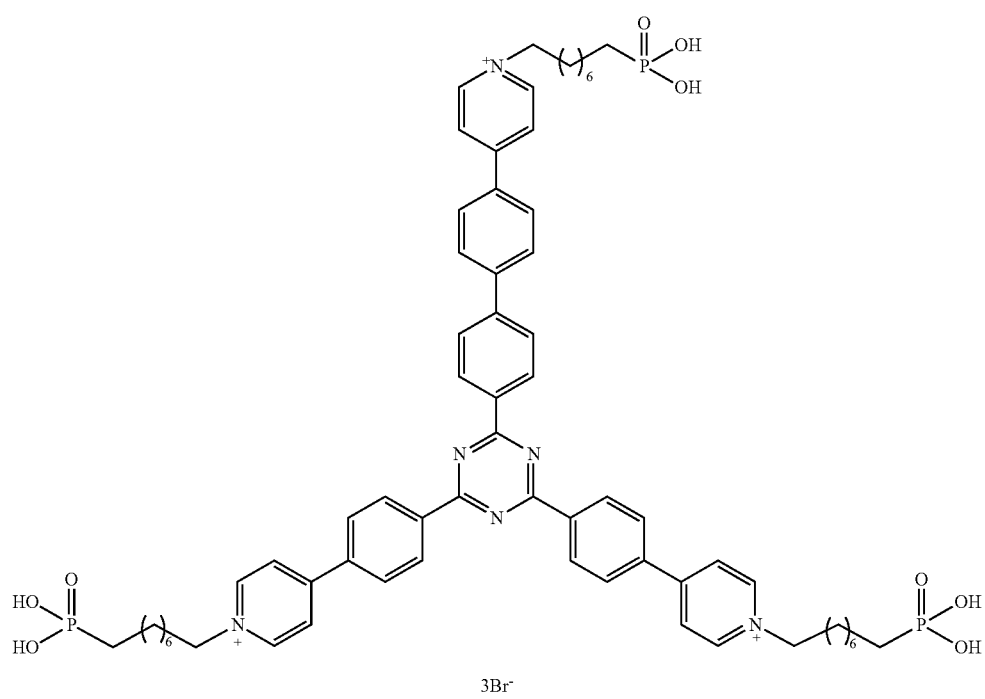
Structural Formula (21)
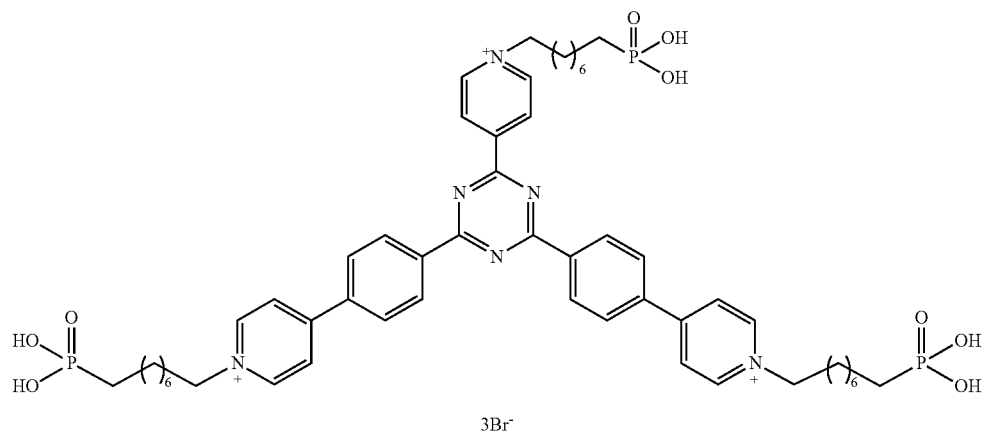

Structural Formula (22)
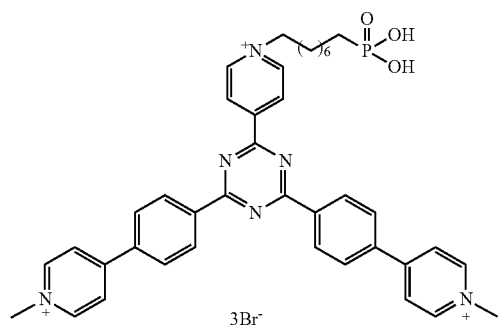
Structural Formula (23)
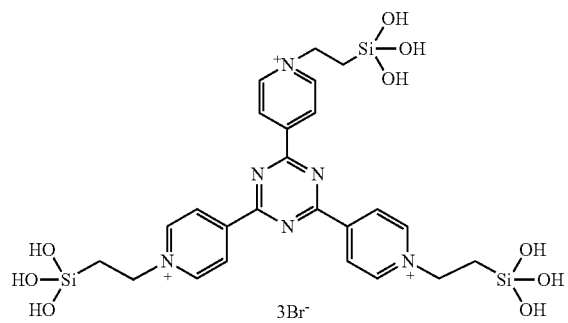
Structural Formula (24)
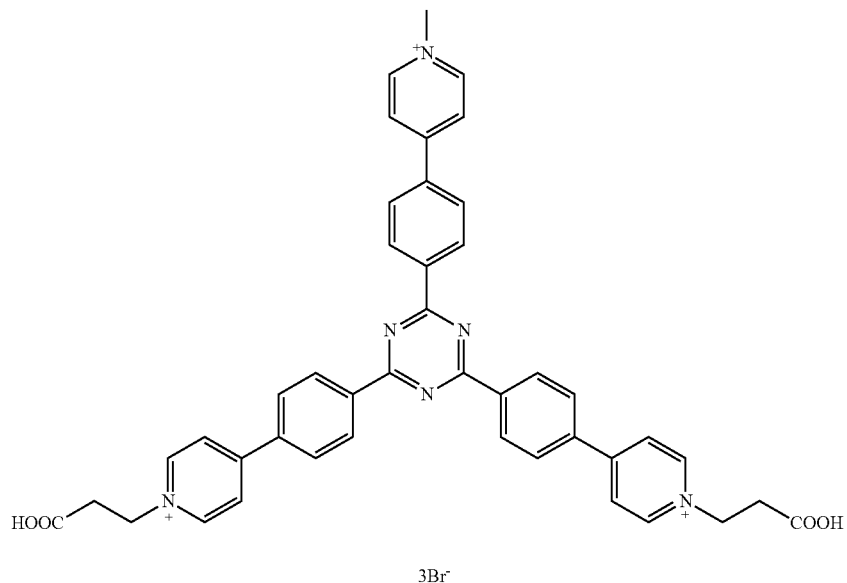
Structural Formula (25)
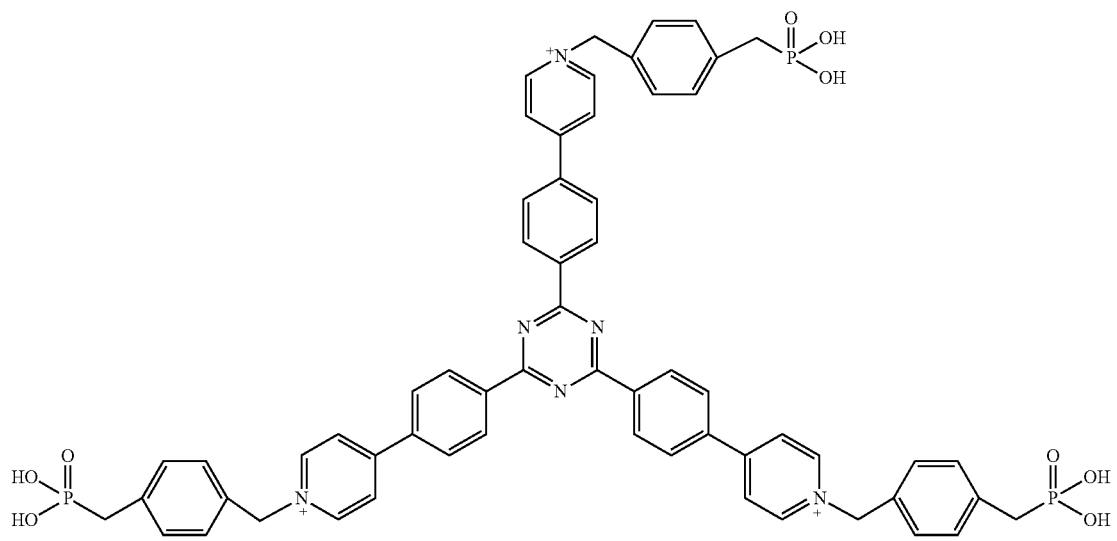

-continued
Structural Formula (26)
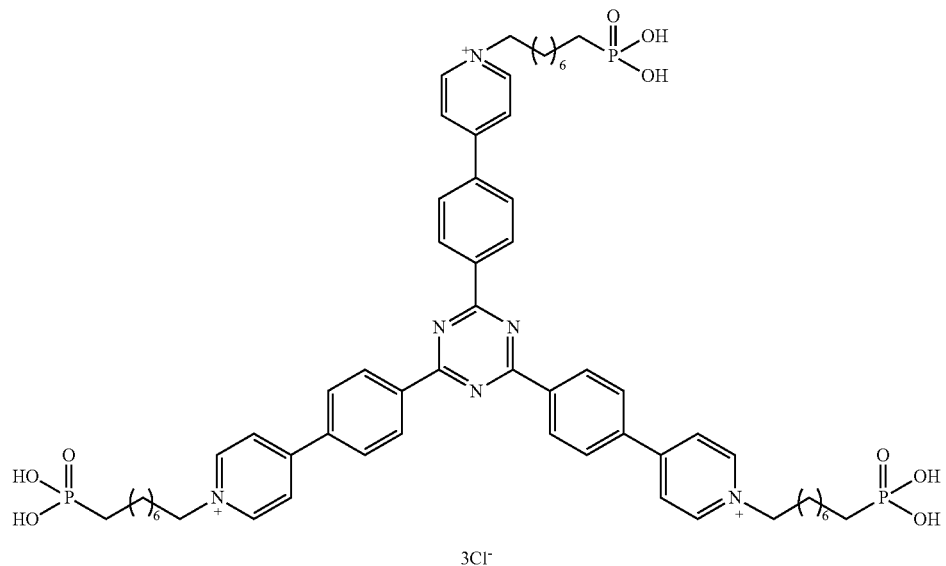
Structural Formula (27)
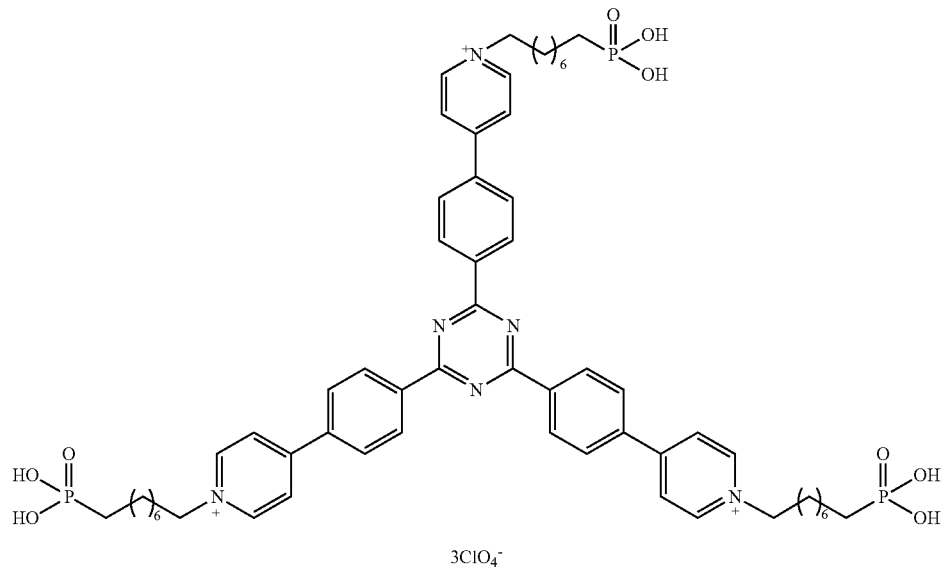

Structural Formula (28)

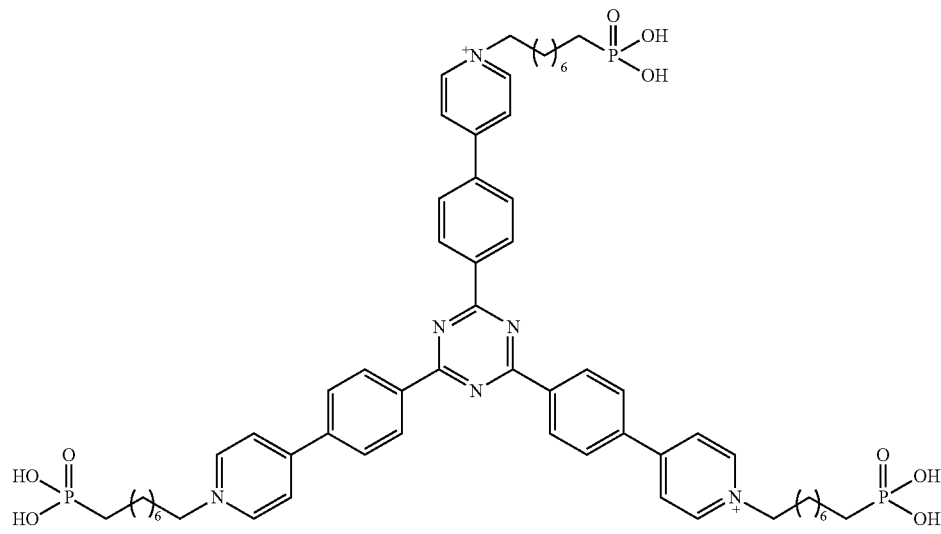

3PF$_6^-$

Structural Formula (29)

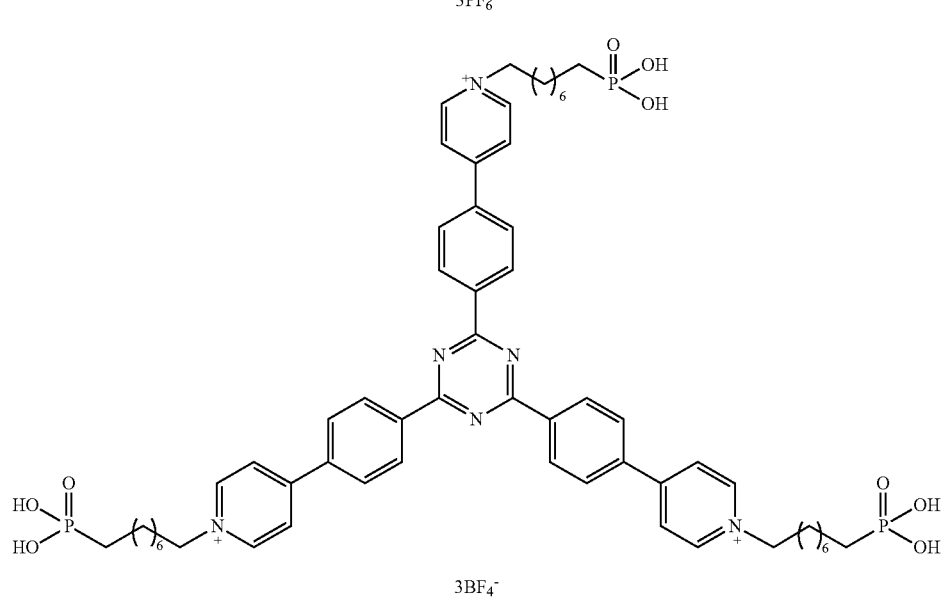

3BF$_4^-$

Moreover, the electrochromic composition of the present invention contains an electroconductive or semiconductive nano structure, to which the electrochromic compound of the present invention [the electrochromic compound represented by the general formula (I), (Ia), (III), (IV), or (V)] is adsorbed.

The electrochromic composition of the present invention colors in black when used in an electrochromic display element, and has excellent memory of an image, and excellent color image retaining properties. Note that, the electroconductive or semiconductive nanostructure is nano particles, a nano porous structure, or a structure having nano-scale irregularities.

In the case where $B_1$, or $B_2$, or the both have a functional group capable of directly or indirectly bonding to a hydroxyl group, the electrochromic compound is easily form a composite with the nanostructure to form an electrochromic composition having excellent color image retention properties, for example, when the electrochromic compound of the present invention contains a sulfonic acid group, a phosphorous acid group (a phosphonic acid group), a phosphoric acid group, or a carboxyl group (a carboxylic acid group), as a bonding or adsorbing structure. The electrochromic compound may contain a plurality of the aforementioned sulfonic acid group, phosphorous acid group, phosphoric acid group, or carboxyl group. When the electrochromic compound of the present invention contains a silyl group or a silanol group, moreover, the electrochromic compound is bonded to the nanostructure via a siloxane bond, which is a solid bonding, and therefore a stable electrochromic composition is attained. In the present specification, the siloxane bond is a chemical bond formed through a silicon atom and oxygen atoms. Moreover, a bonding method or embodiment of the electrochromic composition is not particularly limited as long as the electrochromic composition has a structure where the electrochromic compound and the nanostructure are bonded through a siloxane bond.

As for a material for constituting the electroconductive or semiconductive nanostructure, metal oxide is preferable in view of transparency and electroconductivity. Examples of the metal oxide include metal oxide containing, as a main component, titanium oxide, zinc oxide, tin oxide, zirconium oxide, cerium oxide, yttrium oxide, boron oxide, magnesium oxide, strontium titanate, potassium titanate, barium titanate, calcium titanate, calcium oxide, ferrite, hafnium oxide, tungsten oxide, iron oxide, copper oxide, nickel oxide, cobalt oxide, barium oxide, strontium oxide, vanadium oxide, aluminosilicate, calcium phosphate, or aminosilicate. These metal oxides may be used alone, or in combination as a mixture.

Considering electric properties, such as electric conductivity, and physical properties, such as optical properties, excellent coloring-discoloring response speed is achieved when at least one metal oxide selected from the group consisting of titanium oxide, zinc oxide, tin oxide, zirconium oxide, iron oxide, magnesium oxide, indium oxide, and tungsten oxide, or a mixture thereof is used. Especially when titanium oxide is used, excellent coloring-discoloring response speed is attained.

As for a shape of the metal oxide, metal oxide particles having the average primary particle diameter of 30 nm or smaller are preferable. Use of the smaller particle diameter thereof improves transmittance of light to the metal oxide, and realizes use of a shape having a large surface area per unit (referred to as "specific surface area" hereinafter). Use of the metal oxide having a large specific surface area can more efficiently bear the electrochromic compound thereon, which realizes monochrome display having excellent display contrast of coloring and discoloring. The specific surface area of the nanostructure is not particularly limited, but for example, the specific surface area thereof is $100 \, m^2/g$ or greater.

Next, the display element of the present invention is explained.

The display element of the present invention contains a display electrode, a counter electrode provided facing the display electrode with a space therebetween, and an electrolyte provided between the both electrodes. A display layer containing the electrochromic compound represented by the general formula (I), (III), (IV), or (V) is provided on a surface of the display electrode facing the counter electrode.

FIG. 1 illustrates an example of a structure of a typical display element using the electrochromic compound of the present invention. As illustrated in FIG. 1, the display element 10 of the present invention contains a display electrode 1, a counter electrode 2 provided facing the display electrode 1 with a space therebetween, and an electrolyte 3, which is provided between both electrodes (the display electrode 1 and the counter electrode 2), and contains at least the electrochromic compound (organic electrochromic compound) 4 of the present invention dissolved therein. In this display element, the electrochromic compound colors and discolors through an oxidization reduction reaction only at surface of the electrode.

Figure 2:
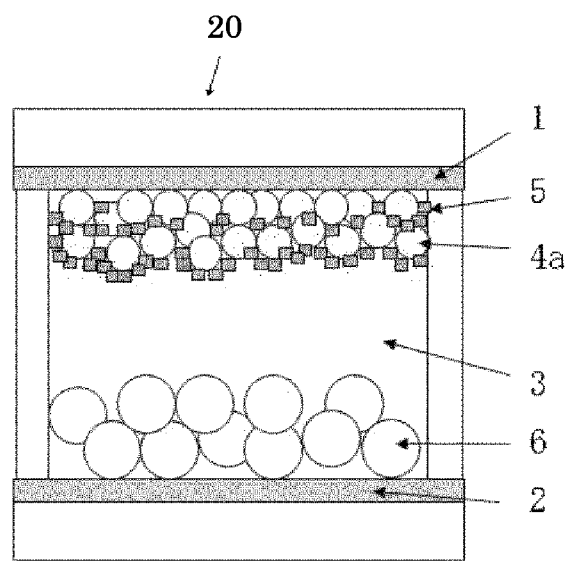
FIG. 2 is a schematic diagram illustrating an example of a structure of a typical display element using the electrochromic composition of the present invention.

FIG. 2 illustrates another example of a structure of a typical display element using the electrochromic compound of the present invention.

The display element 20 of the present invention contains a display electrode 1, a counter electrode 2 provided facing the display electrode 1 with a space therebetween, and an electrolyte 3 provided between both electrodes (the display electrode 1 and the counter electrode 2). A display layer 5 containing at least the electrochromic composition 4a of the present invention is provided on a surface of the display electrode 1. Moreover, a white reflective layer 6 composed of white particles is provided a surface of the counter electrode 2 at the side of the display electrode 1.

As for the electrochromic compound in the electrochromic composition of the present invention, an electrochromic compound having, in a molecular structure thereof, a functional group (absorption group) capable of directly or indirectly bonding to a hydroxyl group, so-called a linking group, is used. The linking group is bonded to the electroconductive or semiconductive nanostructure, to thereby form an electrochromic composition. Then, the electrochromic compositions are provided on the display electrode 1 in the form of a layer, to thereby form a display layer 5.

Materials used in the electrochromic display elements 10 and 20 in accordance with the embodiments of the present invention are explained hereinafter.

As for a material for constituting the display electrode 1, a transparent electroconductive substrate is preferably used. The transparent electroconductive substrate is glass or a plastic film coated with a transparent electroconductive thin film.

The transparent electroconductive thin film material is not particularly limited, provided that it is a material having electroconductivity, but a transparent electroconductive material that is transparent and has excellent electroconductivity, as it is necessary to secure transmittance of light. Use of the aforementioned material can enhance visibility of color to be colored.

As for the transparent electroconductive material, an inorganic material, such as tin-doped indium oxide (abbrev.: ITO), fluorine-doped tin oxide (abbrev.: FTO), and antimony-doped tin oxide (abbrev.: ATO), can be used. Particularly preferred is an inorganic material containing at least one selected from the group consisting of indium oxide (referred to as In oxide hereinafter), tin oxide (referred to as Sn oxide hereinafter), and zinc oxide (referred to as Zn oxide hereinafter). The In oxide, Sn oxide and Zn oxide are materials, which can be easily formed into a film by sputtering, and give excellent transparency and electroconductivity. Moreover, particularly preferable materials are InSnO, GaZnO, SnO, $In_2O_3$, and ZnO.

Examples of a material for constituting a display substrate (no reference number is provided), to which the display electrode 1 is provided, include glass, and plastic. In the case where a plastic film is used as the display substrate, a light and flexible display element can be produced.

As for the counter electrode 2, a transparent electroconductive film (e.g., ITO, FTO, and zinc oxide), an electroconductive metal film (e.g., zinc, and platinum), or carbon is used. The counter electrode 2 is typically formed on the counter substrate (reference number is not provided). The counter electrode substrate is also preferably glass or a plastic film. In the case where a metal plate, such as titanium, and zinc, is used as the counter electrode 2, the counter electrode 2 also functions as a substrate.

In the case where a material for constituting the counter electrode 2 contains a material that induces a reverse reaction to the oxidation reduction reaction carried out by the electrochromic composition of the display layer, coloring and discoloring are performed stably. In the case where the electrochromic composition colors as a result of oxidation, specifically, a reduction reaction is carried out.

In the case where the electrochromic composition colors as a result of reduction, use of a material that induces an oxidation reaction as the counter electrode 2 stabilizes a coloring and discoloring reaction performed in the display layer 5 containing the electrochromic composition.

As for a material constituting the electrolyte 3, a solvent, in which a supporting electrolyte is dissolved, is typically used.

As for the supporting electrolyte, for example, a supporting electrolyte of an inorganic ion salt (e.g., alkali metal salt, and alkali earth metal salt), quaternary ammonium salt, acid, or alkali can be used. Specific examples thereof include $LiClO_4$, $LiBF_4$, $LiAsF_6$, $LiPF_6$, $CF_3SO_3Li$, $CF_3COOLi$, KCl, $NaClO_3$, NaCl, $NaBF_4$, NaSCN, $KBF_4$, $Mg(ClO_4)_2$, and $Mg(BF_4)_2$.

As for the solvent, moreover, usable are propylene carbonate, acetonitrile, γ-butyrolactone, ethylene carbonate, sulfolane, dioxolane, tetrahydrofuran, 2-methyltetrahydrofuran, dimethylsulfoxide, 1,2-dimethoxyethane, 1,2-ethoxymethoxyethane, polyethylene glycol, and alcohol.

As the electrolyte is not particularly limited to a fluid electrolyte in which a supporting electrolyte is dissolved in a solvent, a gel electrolyte, or a solid electrolyte, such as a polymer electrolyte can be also used. Examples of the solid electrolyte include a perfluorosulfonic acid-based polymer membrane. The solution electrolyte has an advantage that it has high ion conductivity, and the solid electrolyte is suitable for producing an element that does not deteriorate and has high durability.

In the case where the display element of the present invention is used as a reflecting display element, moreover, it is preferred that a white reflective layer 6 be provided between the display electrode 1 and counter electrode 2, as illustrated in FIG. 2. As for the formation of the white reflective layer 6, the simplest production method thereof is dispersing white pigment particles in a resin, and applying the resultant onto the counter electrode 2.

As for the white pigment particles, particles formed of typical metal oxide can be used. Specific examples thereof include titanium oxide, aluminum oxide, zinc oxide, silicon oxide, cesium oxide, and yttrium oxide. Moreover, the electrolyte can be also functioned as a white reflecting layer by mixing the white pigment particles with a polymer electrolyte.

As for a driving method of the display elements 10 and 20, any method may be used as long as the predetermined voltage and current can be applied. Use of a passive driving system can produce an inexpensive display element. Moreover, use of an active driving system can perform display of high definition and high speed. The active driving can be easily realized by providing active driving elements on the counter substrate.

Figure 3:
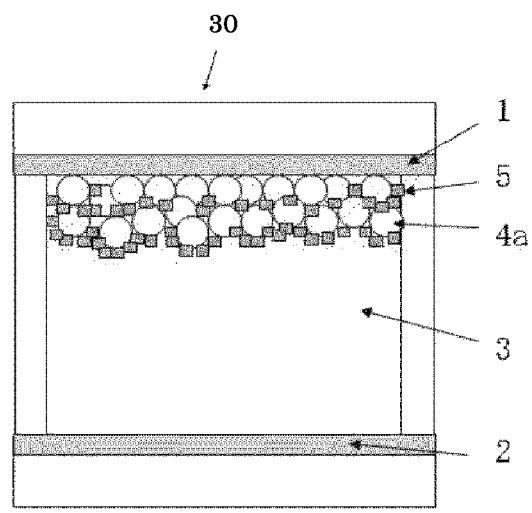
FIG. 3 is a schematic diagram illustrating an example of a structure of a typical dimming element using the electrochromic composition of the present invention.

Another example of a structure of typical display element using the electrochromic compound of the present invention is depicted in FIG. 3.

The dimming element 30 of this example contains a display electrode 1, a counter electrode 2 provided to face the display electrode 1 with a space therebetween, and an electrolyte 3 provided between both electrodes (the display electrode 1 and the counter electrode 2). A display layer 5 containing at least the electrochromic composition 4a of the present invention is provided in the electrolyte 3 at the side of the surface of the display electrode 1.

In this display element, the electrochromic compound colors and discolors through an oxidation reduction reaction only at a surface of the electrode. The transparency of the entire element is important for the dimming element.

As for the electrochromic compound in the electrochromic composition of the present invention, an electrochromic compound having, in a molecular structure thereof, a functional group (absorption group) capable of directly or indirectly bonding to a hydroxyl group, so-called a linking group, is used. The linking group is bonded to the electroconductive or semiconductive nanostructure, to thereby form an electrochromic composition. Then, the electrochromic compositions are provided on the display electrode 1 in the form of a layer, to thereby form a display layer 5.

Materials used for the electrochromic dimming element 30 in accordance with the embodiment of the present invention are explained hereinafter.

As for a material for constituting the display electrode 1, it is important that a transparent electroconductive substrate is used. As for the transparent electroconductive substrate, preferred is glass or a plastic film coated with a transparent electroconductive thin film A material of the transparent electroconductive thin film is not particularly limited as long as it is a material having electroconductivity. In order to secure light transmittance, however, a transparent electroconductive material, which is transparent and has excellent electroconductivity, is used. Use of the transparent electroconductive material can enhance visibility of a color to be colored.

As for the transparent electroconductive material, an inorganic material, such as tin-doped indium oxide (abbrev.: ITO), fluorine-doped tin oxide (abbrev.: FTO), and antimony-doped tin oxide (abbrev.: ATO), can be used. Particularly preferred is an inorganic material containing at least one selected from the group consisting of indium oxide (referred to as In oxide hereinafter), tin oxide (referred to as Sn oxide hereinafter), and zinc oxide (referred to as Zn oxide hereinafter). The In oxide, Sn oxide and Zn oxide are materials, which can be easily formed into a film by sputtering, and give excellent transparency and electroconductivity. Moreover, particularly preferable materials are InSnO, GaZnO, SnO, $In_2O_3$, and ZnO.

Examples of a material for constituting a display substrate (no reference number is provided), to which the display electrode 1 is provided, include glass and plastic. Use of a plastic film as a display substrate can produce a light and flexible display element.

Similarly to the display electrode 1, it is also important that a transparent electroconductive substrate is used for the counter electrode 2. The transparent electroconductive substrate is preferably glass or a plastic film coated with a transparent electroconductive thin film.

A material of the transparent electroconductive thin film of the counter electrode 2 is not particularly limited as long as it is a material having electroconductivity. In order to secure light transmittance, however, a transparent electroconductive material, which is transparent and has excellent electroconductivity, is used. Use of the transparent electroconductive material can enhance visibility of a color to be colored.

As for the transparent electroconductive material, an inorganic material, such as tin-doped indium oxide (abbrev.: ITO), fluorine-doped tin oxide (abbrev.: FTO), and antimony-doped tin oxide (abbrev.: ATO), can be used. Particularly preferred is an inorganic material containing at least one selected from the group consisting of indium oxide (referred to as In oxide hereinafter), tin oxide (referred to as Sn oxide hereinafter), and zinc oxide (referred to as Zn oxide hereinafter). The In oxide, Sn oxide and Zn oxide are materials, which can be easily formed into a film by sputtering, and give excellent transparency and electroconductivity. Moreover, particularly preferable materials are InSnO, GaZnO, SnO, $In_2O_3$, and ZnO.

Similarly to the display electrode 1, examples of a display substrate (no reference number is provided), to which the counter electrode 2 is provided, include glass, and plastic. In the case where a plastic film is used as the display substrate, a light and flexible display element can be produced.

In the case where a material for constituting the counter electrode 2 contains a material that induces a reverse reaction to the oxidation reduction reaction carried out by the electrochromic composition of the display layer, coloring and discoloring are performed stably. Specifically, when a material that induces a reduction reaction if the electrochromic composition colors as a result of oxidation, or a material that induces an oxidation reaction if the electrochromic composition colors as a result of reduction, is used as the counter electrode 2, a coloring and discoloring reaction is stably performed in the display layer 5 containing the electrochromic composition.

As for a material constituting the electrolyte 3, a solvent, in which a supporting electrolyte is dissolved, is typically used. In case of a dimming element, particularly, the electrolyte 3 needs to be colorless and transparent.

As for the supporting electrolyte, for example, a supporting electrolyte of an inorganic ion salt (e.g., alkali metal salt, and alkali earth metal salt), quaternary ammonium salt, acid, or alkali can be used. Specific examples thereof include $LiClO_4$, $LiBF_4$, $LiAsF_6$, $LiPF_6$, $CF_3SO_3Li$, $CF_3COOLi$, KCl, $NaClO_3$, NaCl, $NaBF_4$, NaSCN, $KBF_4$, $Mg(ClO_4)_2$, and $Mg(BF_4)_2$.

As for the solvent, moreover, usable are propylene carbonate, acetonitrile, γ-butyrolactone, ethylene carbonate, sulfolane, dioxolane, tetrahydrofuran, 2-methyltetrahydrofuran, dimethylsulfoxide, 1,2-dimethoxyethane, 1,2-ethoxymethoxyethane, polyethylene glycol, and alcohol.

As the electrolyte is not particularly limited to a fluid electrolyte in which a supporting electrolyte is dissolved in a solvent, a gel electrolyte, or a solid electrolyte, such as a polymer electrolyte can be also used. Examples of the solid electrolyte include a perfluorosulfonic acid-based polymer membrane. The solution electrolyte has an advantage that it has high ion conductivity, and the solid electrolyte is suitable for producing an element that does not deteriorate and has high durability.

As for a driving method of the dimming element 30, any method may be used as long as the predetermined voltage and current can be applied. Use of a passive driving system can produce an inexpensive display element. Moreover, use of a transparent active driving element, dimming can be performed highly precisely and at high speed. Examples of the transparent active driving element include IGZO.

EXAMPLES

The electrochromic compound and electrochromic composition of the present invention, and the display element and dimming element using the electrochromic compound and electrochromic composition are explained through Examples, hereinafter. These Examples however shall not be construed as to limit the scope of the present invention in any way.

Example 1

<Synthesis of Electrochromic Compound [Structural Formula (19)]>
<a> Synthesis of Intermediate (19-1)

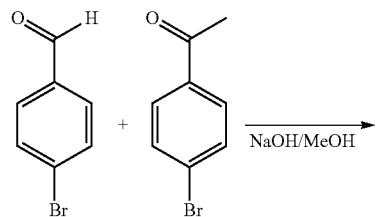

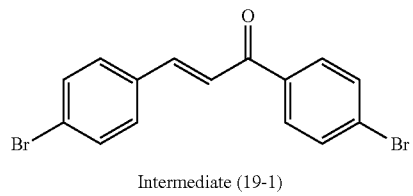

Intermediate (19-1)

A 100 mL three-necked rotary flask was charged with 9.25 g (50 mmol) of 4-bromobenzaldehyde, and 9.94 g (50 mmol) of 4-bromoacetophenone, and the contents were dissolved in 50 mL of methanol. To the flask, 0.10 g (2.25 mmol) of sodium hydroxide was added, and the resultant was stirred for 6 hours in nitrogen atmosphere at room temperature. After the reaction, the material was obtained through filtration. The obtained material was washed with distilled water and methanol, to thereby obtain a target intermediate (19-1), which was yellow powder.

The intermediate (19-1) had Mp of 184.5° C. to 185.5° C. (lit. 183° C. to 184° C.).

The yielded amount was 17.0 g, and the yield was 92.9%.

<b> Synthesis of Intermediate (19-2)

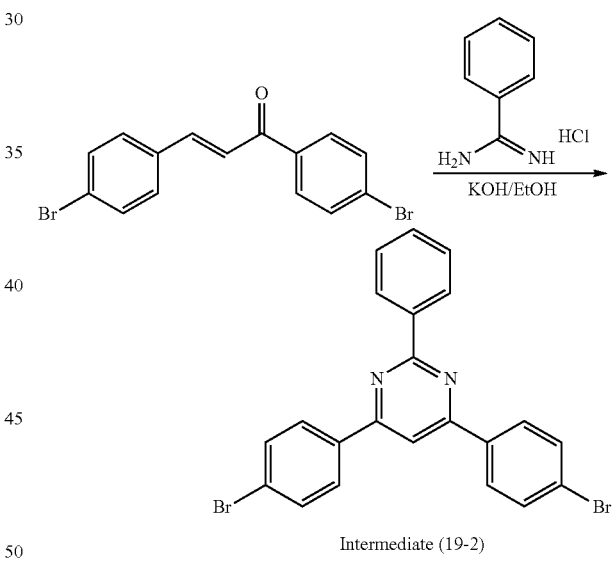

Intermediate (19-2)

In 70 mL of ethanol, 10.0 g (27.3 mmol) of the intermediate (19-1), and 2.28 g (13.7 mmol) of benzamidine hydrochloride (94%) were dissolved. To this, a solution obtained by dissolving 1.80 g (32.1 mmol) of potassium hydroxide (85%) in 50 mL of ethanol was added dropwise over 15 minutes, followed by performing reflux for 24 hours. The resultant was washed with distilled water, and a generated product was purified by silica-gel column chromatography (toluene). The resulting crude product was purified by recrystallizing in toluene/hexane, to thereby obtain a target.

The intermediate (19-2) had Mp of 204.5° C. to 205.0° C. (lit. 203° C. to 205° C.).

The yielded amount was 5.06 g, and the yield was 39.8%.

<c> Synthesis of Intermediate (19-3)

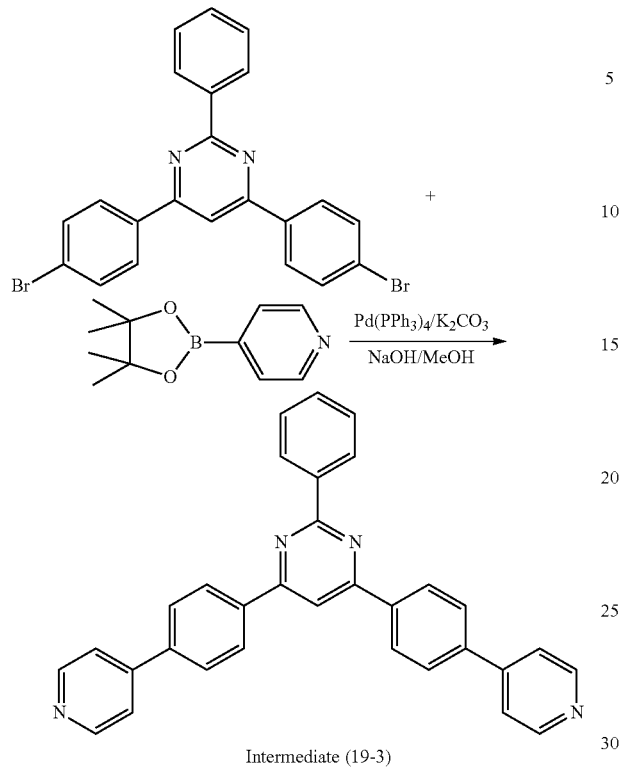

Intermediate (19-3)

A 100 mL three-necked rotary flask was charged with 10 mL of toluene, which had been deaired in advance, and 2 mL of ethanol, and 0.47 g (1.0 mmol) of the intermediate (19-2) and 0.62 g (3.0 mmol) of 4-pyridineboronic acid pinacol ester were dissolved therein. While blowing nitrogen into the rotary flask, 36 mg (0.03 mmol; 3 mol %) of tetrakis (triphenylphosphine)palladium and 2.5 g of 2M potassium carbonate were added, followed by performing reflux for 14 hours. To the resulting solution, toluene was added to extract an organic layer, followed by washing the organic layer with distilled water.

After adding magnesium sulfate as a desiccant to the organic layer to dehydrate, the solvent was removed under the reduced pressure. The resulting crude product was then refluxed with a mixed solvent of ethanol/ethyl acetate, to thereby obtain a target, which was colorless powder.

The yielded amount was 0.34 g, and the yield was 72.3%.

<d> Synthesis of Electrochromic Compound (19) [Structural Formula (19)]

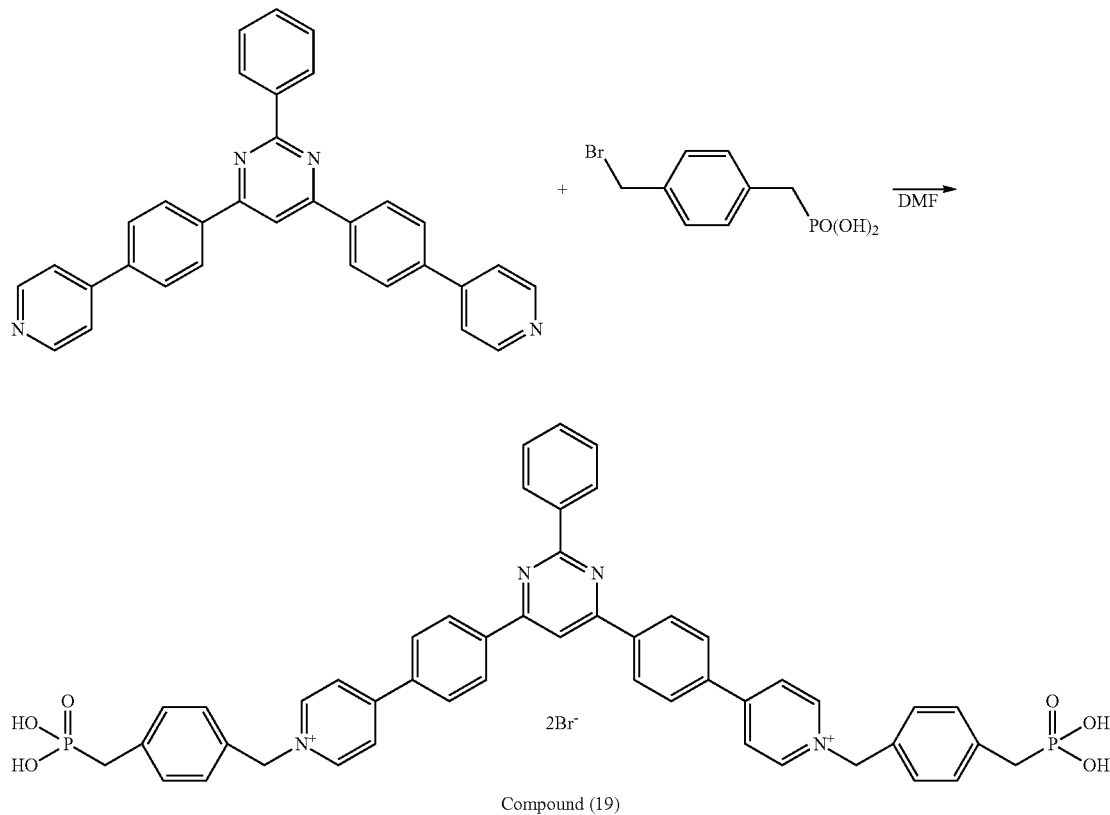

Compound (19)

A 25 mL three-necked flask was charged with 0.113 g (0.40 mmol) of the intermediate (19-3), 0.358 g (1.35 mmol) of 4-bromomethylbenzyl phosphonate, and 3.0 mL of dimethyl formamide, and the resulting mixture was allowed to react for 2 hours at 90° C. After returning the resulting solution to room temperature, the solution was discolored into 2-propanol. Subsequently, the obtained solids were dispersed in 2-propanol, followed by collecting the solids. The obtained solids were dried under the reduced pressure for 2 days at 100° C., to thereby obtain a target.

The yielded amount was 0.29 g, and the yield was 90%.
[Production and Evaluation of Electrochromic Display Element]
(a) Formation of Display Electrode and Electrochromic Display Layer First, a glass substrate with FTO electric conductive film in the size of 25 mm×30 mm (manufactured by AGC Fabritech Co., Ltd.) was provided. Onto the 19 mm×15 mm region of the top surface of the glass substrate, a titanium oxide nano particle dispersion liquid (SP210, manufactured by Showa Titanium K.K.) was applied by spin coating, followed by performing annealing for 15 minutes at 120° C., to thereby form a titanium oxide particle film.

Onto the titanium oxide particle film, a 1% by weight 2,2,3,3-tetrafluoropropanol solution of the compound represented by the structural formula (19) was applied as a coating liquid by spin coating, and the applied solution was subjected to annealing for 10 minutes at 120° C., to thereby form a display layer 5 having the electrochromic compound adsorbed on surfaces of the titanium oxide particles.

Note that, a structure of the produced electrochromic display element conformed to the structure of FIG. 2 (provided that, a white reflective layer was excluded).
(b) Formation of White Reflective Layer Moreover, a solution, in which a urethane paste (HW140SF, manufactured by DIC Corporation) was dissolved as a binding polymer in an amount of 10% by weight in a 2,2,3,3-tetrafluoropropanol solution, was provided. To this solution, 50% by weight of titanium oxide particles (product name: CR90, manufactured by ISHIHARA SANGYO KAISHA, LTD., average particle diameter: about 250 nm) were dispersed to prepare a paste. The paste was applied onto a surface of the electrochromic layer by spin coating, and the coated paste was subjected to annealing for 5 minutes at 120° C., to thereby form a white reflective layer of about 1 μm.
(c) Formation of Counter Electrode Separately from the glass substrate, a glass substrate with a 25 mm×30 mm ITO electroconductive film (manufactured by GEOMATEC Co., Ltd.) was provided, and used as a counter substrate.

(d) Production of Electrochromic Display Element

A cell was produced by bonding the display substrate and the counter substrate together via a spacer having a thickness of 75 μm. Next, 20% by weight of tetrabutyl ammonium perchlorate was dissolved in dimethyl sulfoxide, to thereby an electrolyte solution. The electrolyte solution was then enclosed in the cell, to thereby produce an electrochromic display element.

Comparative Example 1

The electrochromic compound represented by the following structural formula (82), which was described as [Chem. 46] in PTL 2 (JP-A No. 2011-102287), was synthesized.

Structural Formula 82

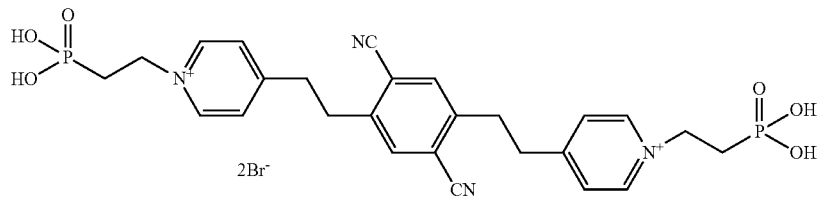

A display electrode and an electrochromic display layer were formed in the same manner as (a) to (d) of Example 1, provided that the obtained electrochromic compound was used, and then an electrochromic display element was produced.
[Coloring Discharging Comparison Test 1]

Figure 4:
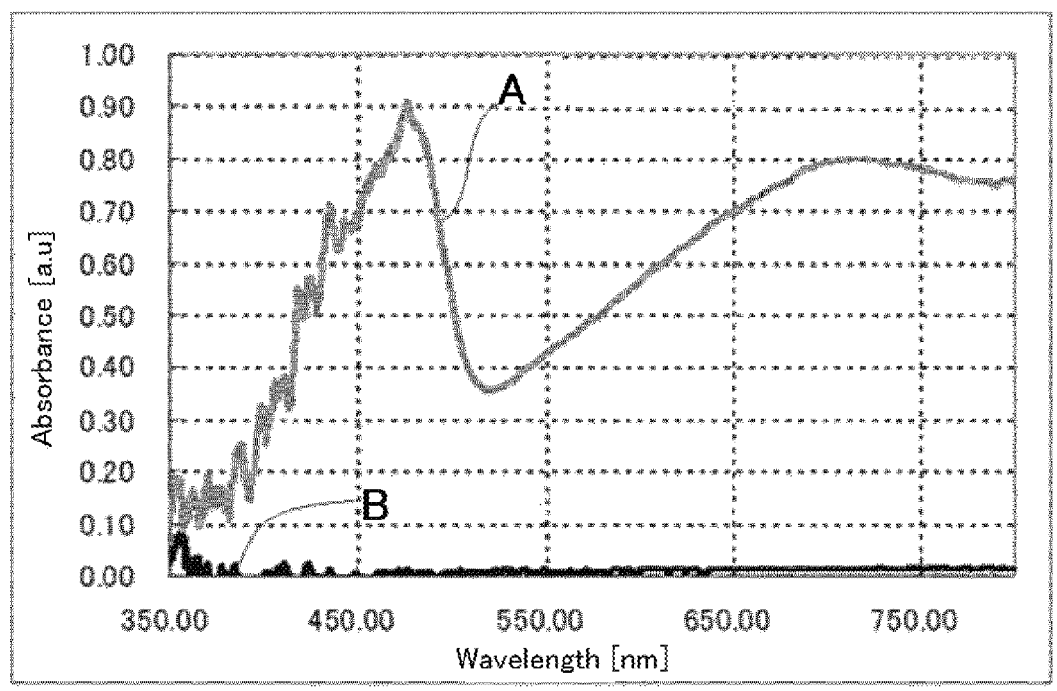
FIG. 4 is a diagram depicting absorption spectra of the discolored state and colored state of the display electrode with the electrochromic display layer produced in Example 1, where A denotes the absorption spectrum of the compound of Example 1 in the colored state, and B denotes the absorption spectrum of the compound of Example 1 in the discolored state.

Each of the display electrodes (a) to each of which the electrochromic display layer had been formed, which were produced in Example 1 and Comparative Example 1, was placed in a quartz cell. A platinum electrode was used as a counter electrode, and an Ag/Ag+ (RE-7, manufactured by BAS Inc.) was used as a reference electrode. An electrolyte solution was prepared by dissolving 0.1 M of tetrabutylammonium perchlorate in dimethyl sulfoxide, and the cell was filled with the electrolyte solution. To this quartz cell, light was applied from a deuterium tungsten halogen light source (DH-2000, manufactured by Ocean Optics, Inc.). The transmitted light was detected by a spectrometer (USB4000, manufactured by Ocean Optics, Inc.), to measure the absorption spectrum. The absorption spectra of the discolored state and colored state are presented in FIG. 4.

In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Figure 5:
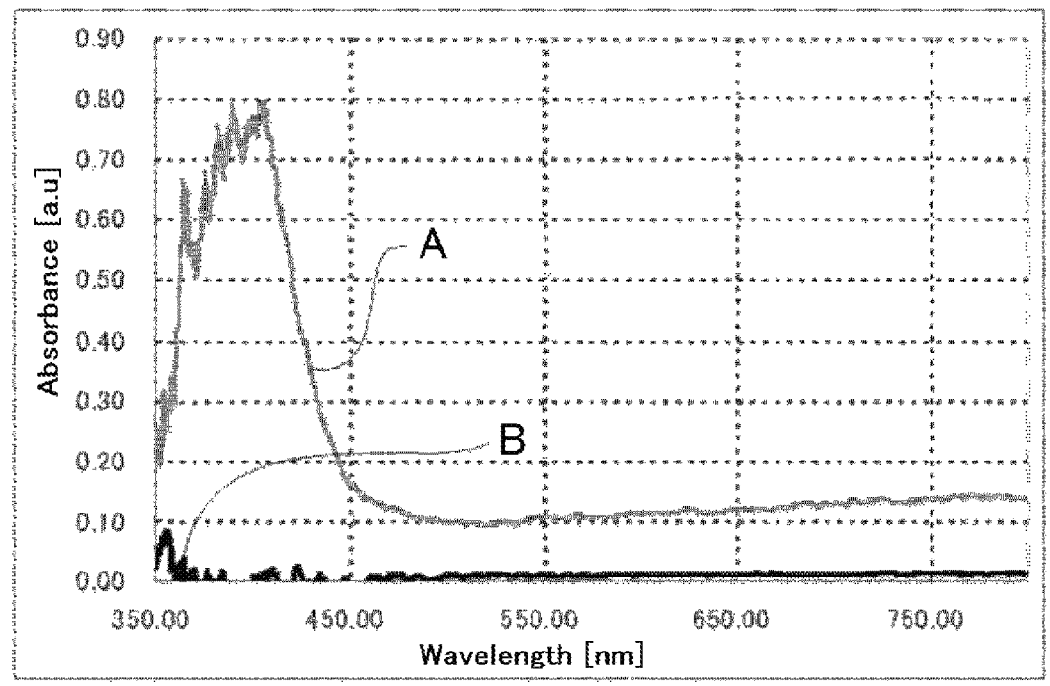
FIG. 5 is a diagram depicting absorption spectra of the discolored state of the electrochromic display element produced in Example 1 and the electrochromic display element in Comparative Example 1, where A denotes the absorption spectrum of the compound of Comparative Example 1 in the discolored state, and B denotes the absorption spectrum of the compound of Example 1 in the discolored state.

A comparison between the absorption spectrum of the discolored state of the electrochromic display layer (d) of Example 1 and the absorption spectrum of the discolored state of the electrochromic display layer (d) of Comparative Example 1 is depicted in FIG. 5. In Comparative Example 1, the absorption was observed at around 400 nm even in the discolored state, and the discolored body had tinted more than the electrochromic compound of Example 1.

Figure 6:
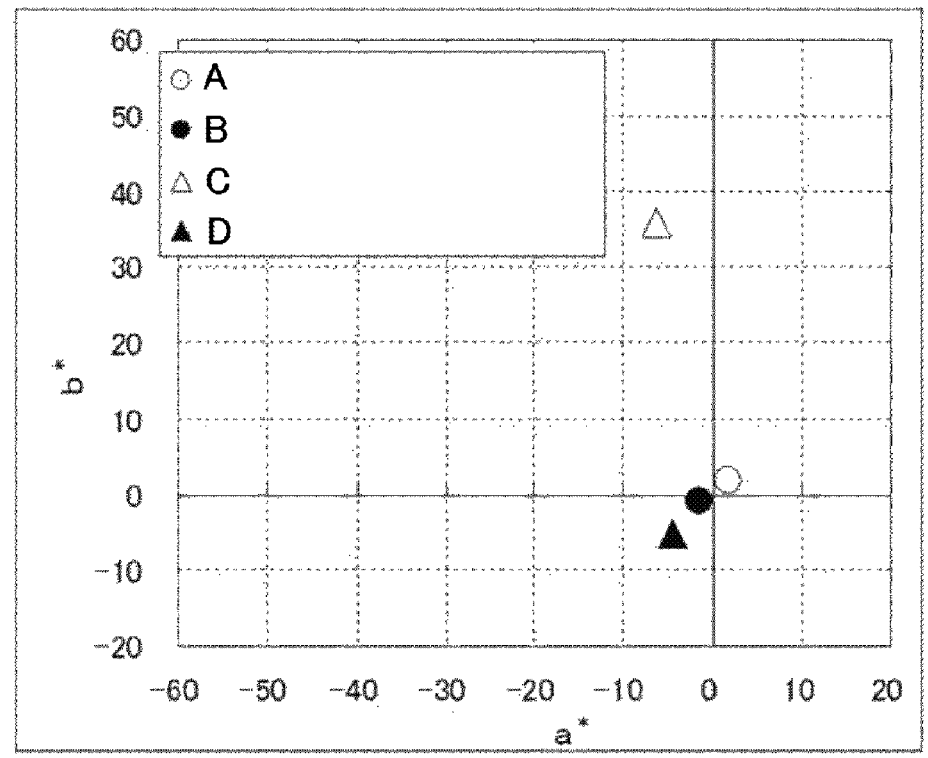
FIG. 6 is a diagram depicting a comparison in a color value between the electrochromic display element produced in Example 1 and the electrochromic display element in Comparative Example 1, where A denotes the color value of the compound of Example 1 in the discolored state, B denotes the color value of the compound of Example 1 in the colored state, C denotes the color value of the compound of Comparative Example 1 in the discolored state, and D denotes the color value of the compound of Comparative Example 1 in the colored state.

The electrochromic display elements (d) produced in Example 1 and Comparative Example 1 were each subjected to comparison evaluation of coloring and discoloring. The evaluation of coloring/discoloring was carried out by applying diffused light using a spectrophotometer MCPD7700, manufactured by Otsuka Electronics Co., Ltd. The color value was evaluated in CIE L*a*b* color space, and a* and b* were plotted in FIG. 6.

In the colored state after applying the voltage of −6.0 V to each display element, both of the electrochromic display elements of Example 1 and Comparative Example 1 had the values of a* and b* plotted to very close to the starting point (0), and it was confirmed that they were both colored substantially in black.

In the discolored state before applying the voltage, the plotted values a* and b* of Example 1 indicated that the color of Example 1 was substantially the same to Japan Color White that would be plotted on the starting point.

On the other hand, Comparative Example 1 had a large value of b*, which indicated that it was tinted with yellow.

It was found from the results above that Example 1 had fewer tints in the discolored state and had high white reflectance in comparison between the electrochromic display element of Example 1 and that of Comparative Example 1.

Example 2

Production and Evaluation of Electrochromic Dimming Element (a) Formation of Display Electrode and Electrochromic Display Layer First, a glass substrate with FTO electric conductive film in the size of 25 mm×30 mm (manufactured by AGC Fabritech Co., Ltd.) was provided. Onto the 19 mm×15 mm region of the top surface of the glass substrate, a titanium oxide nano particle dispersion liquid (SP210, manufactured by Showa Titanium K.K.) was applied by spin coating, followed by performing annealing for 15 minutes at 120° C., to thereby form a titanium oxide particle film.

Onto the titanium oxide particle film, a 1% by weight 2,2,3,3-tetrafluoropropanol solution of the compound (19) represented by the structural formula (19) was applied as a coating liquid by spin coating, and the applied solution was subjected to annealing for 10 minutes at 120° C., to thereby form a display layer 5 having the electrochromic compound adsorbed on a surface of the titanium oxide particles.

Note that, a structure of the produced electrochromic dimming element conformed to the structure of FIG. 3 (provided that, a white reflective layer was excluded).

(b) Formation of Counter Electrode

Separately from the glass substrate, a glass substrate with 25 mm×30 mm an ITO conductive film (manufactured by GEOMATEC Co., Ltd.) was provided, and was used as a counter substrate.

(c) Production of Electrochromic Dimming Element

The display substrate and the counter substrate were bonded together via a spacer of 75 μm, to thereby produce a cell. Next, 20% by weight of tetrabutyl ammonium perchlorate was dissolved in dimethyl sulfoxide, to thereby an electrolyte solution. The prepared electrolyte solution was enclosed in the cell, to thereby produce an electrochromic dimming element.

[Coloring Discharging Comparison Test 2]

To the dimming element (c) produced in Example 2, light was applied from a deuterium tungsten halogen light source (DH-2000, manufactured by Ocean Optics, Inc.). The transmitted light was detected by a spectrometer (USB4000, manufactured by Ocean Optics, Inc.), to measure a transmission spectrum. In the discolored state before applying voltage, there was hardly any absorption in the entire visible region of 400 nm to 700 nm, and the dimming element was transparent. Especially, the transmittance at 550 nm was 80%. When voltage of −6.0 V was applied to the dimming element for 2 seconds, the dimming element colored in black, and it was found that the transmittance at 550 nm was reduced to 10%.

Example 3

<Synthesis of Electrochromic Compound (26) [Structural Formula 37]>

<a> Synthesis of Intermediate (37-1)

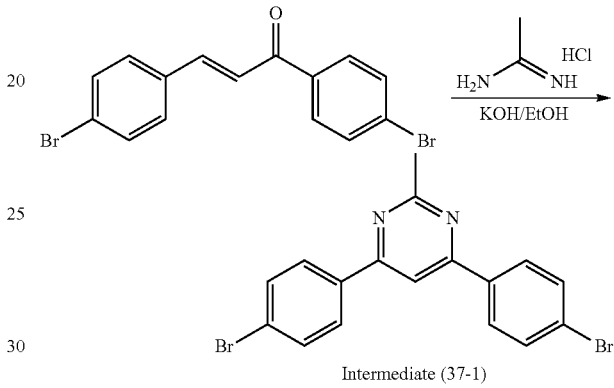

Intermediate (37-1)

A target was obtained in the same synthesis route to <b> in Example 1 using the intermediate (18-1) synthesized in Example 1<a>, provided that benzamidine hydrochloride was replaced with acetoamidine hydrochloride.

<c> Synthesis of Intermediate (37-2)

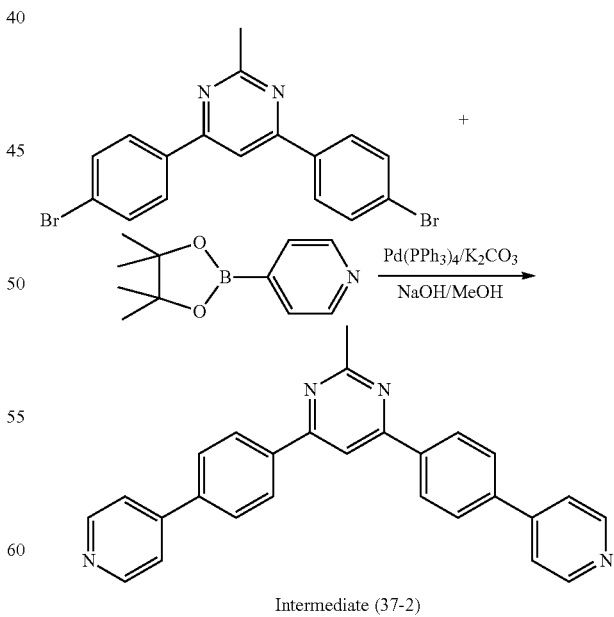

Intermediate (37-2)

The intermediate (37-1) and 4-pyridineboronic acid pinacol ester were allowed to react in the same synthesis route to <c> in Example 1 to thereby obtain a target.

<d> Synthesis of Electrochromic Compound (37) [Structural Formula (37)]

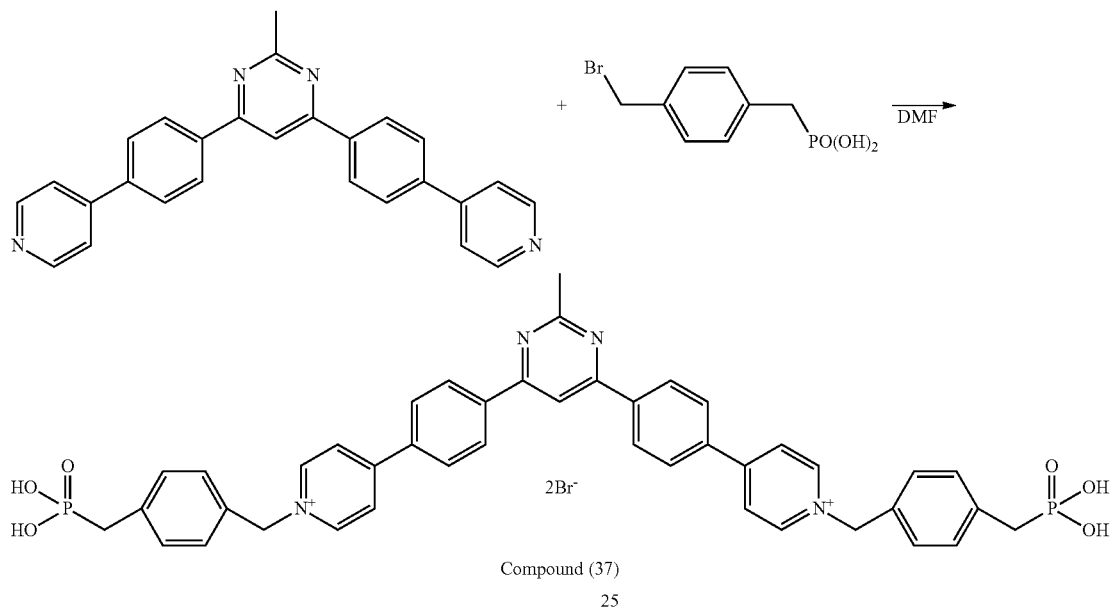

Compound (37)

Figure 7:
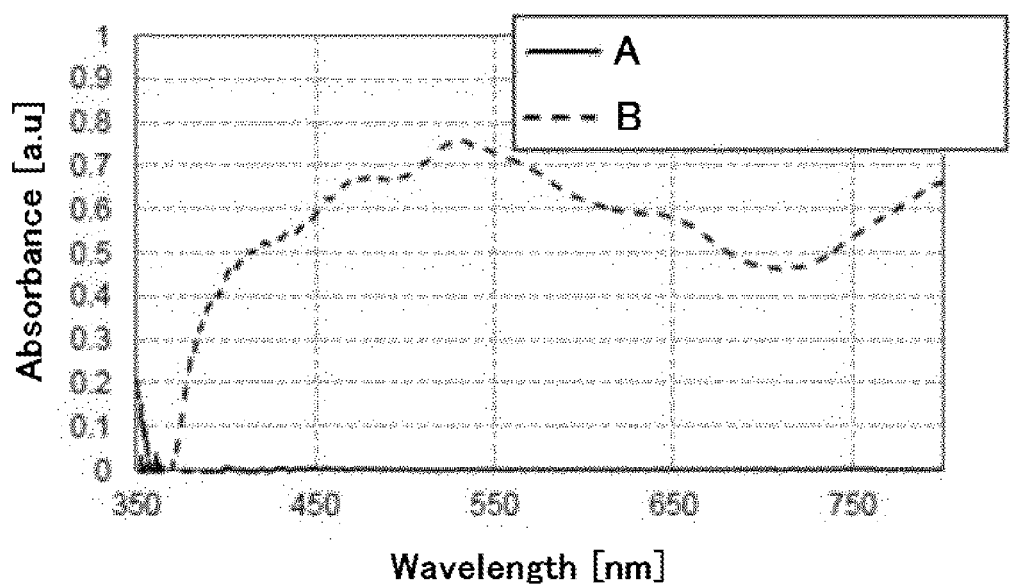
FIG. 7 is a diagram depicting absorption spectra of the discolored state and colored state of the display electrode with the electrochromic display layer produced in Example 3, where A denotes the absorption spectrum of the compound of Example 3 in the discolored state, and B denotes the absorption spectrum of the compound of Example 3 in the colored state.

A target, which was a colorless powder, was obtained using the intermediate (37-2) and 4-bromomethylbenzyl phosphonate in the same manner as in <d> of Example 1.
[Production and Evaluation of Electrochromic Display Element]
An electrochromic display element was produced in the same manner as the method described in [Production and Evaluation of Electrochromic Display Element] of Example 1, provided that the compound (37) represented by the structural formula (37) was used as a luminescent dye.
[Coloring Discharging Comparison Test 3]
An absorption spectrum was measured in the same manner as in [Coloring Discharging Comparison Test 1]. The discolored state and charged state of the absorption spectra are depicted in FIG. 7. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 4

<Synthesis of Electrochromic Compound (27) [Structural Formula (27)]>
<a> Synthesis of Intermediate (27-1)

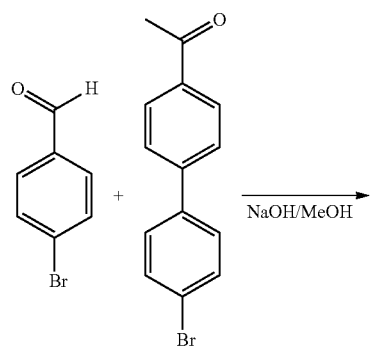

-continued

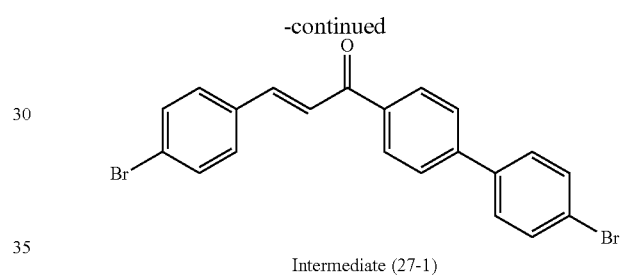

Intermediate (27-1)

A target was obtained in the same manner as in the synthesis method of the intermediate (26-1) in <a> of Example 1, provided that the reaction was carried out using 4-acetyl-4'-boromobiphenyl instead of 4-bromoacetophenone.
<b> Synthesis of Intermediate (27-2)

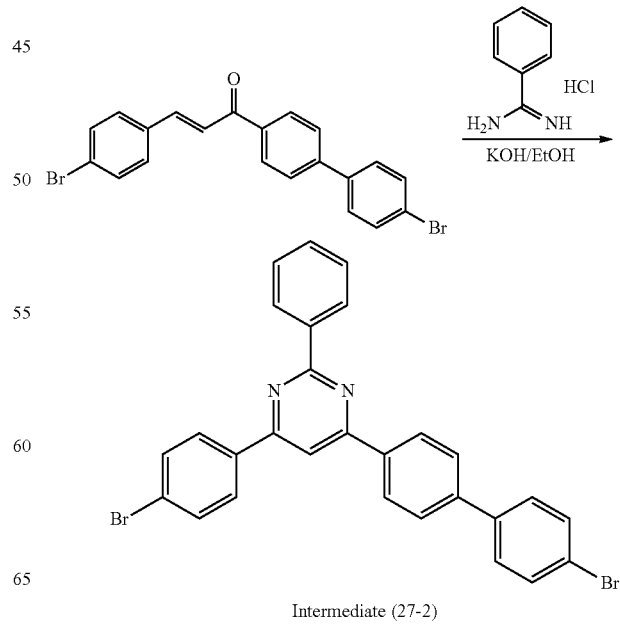

Intermediate (27-2)

A target was obtained from the intermediate (27-1) in the same synthesis method to that in Example 1<b>.
<c> Synthesis of Intermediate (27-3)
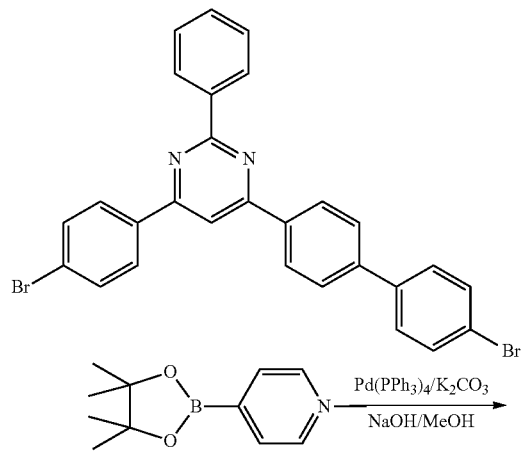
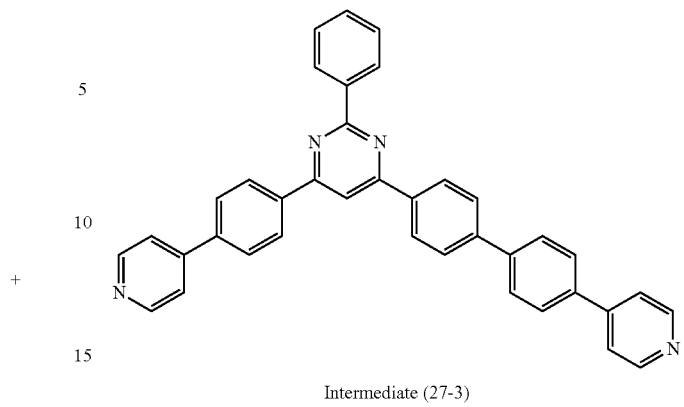
Intermediate (27-3)
A target was obtained from the intermediate (27-2) in the same synthesis method as in <c> of Example 1.
<d> Synthesis of Electrochromic Compound (27) [Structural Formula (27)]
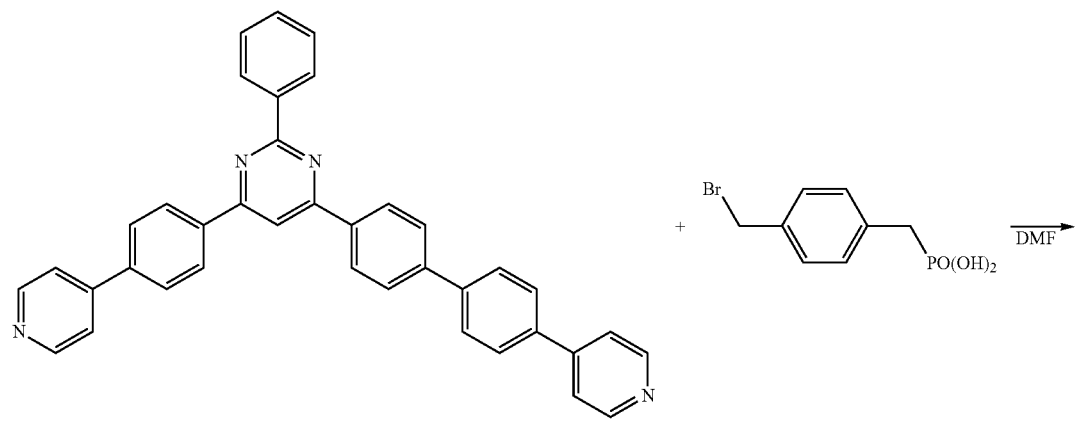
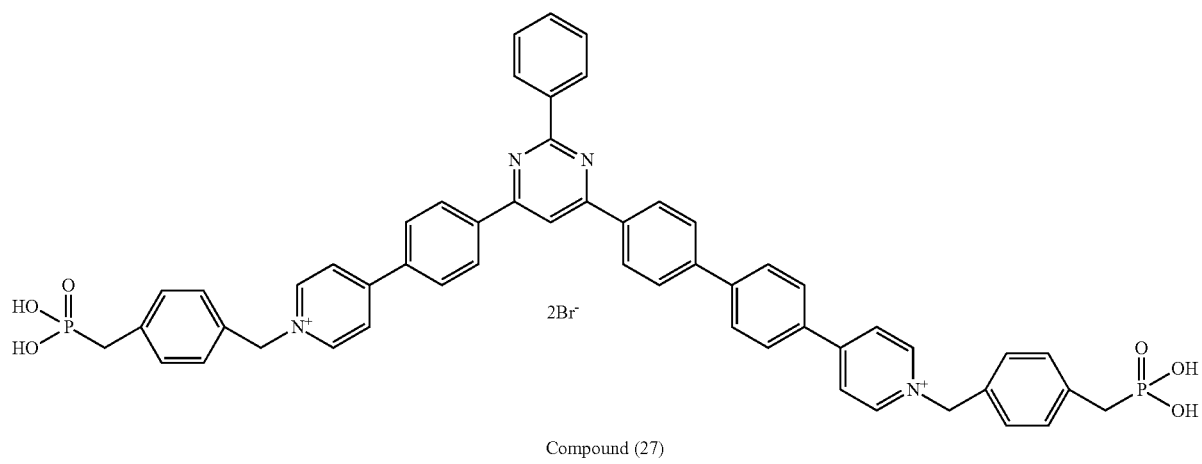
Compound (27)

A target was obtained using the intermediate (27-3) in the same manner as in <c> of Example 1.

[Production and Evaluation of Electrochromic Display Element]

An electrochromic display element was produced in the same manner as the method described in [Production and Evaluation of Electrochromic Display Element] of Example 1, provided that the compound (27) represented by the structural formula (27) was used as a luminescent dye.

[Coloring Discharging Comparison Test 4]

Figure 8:
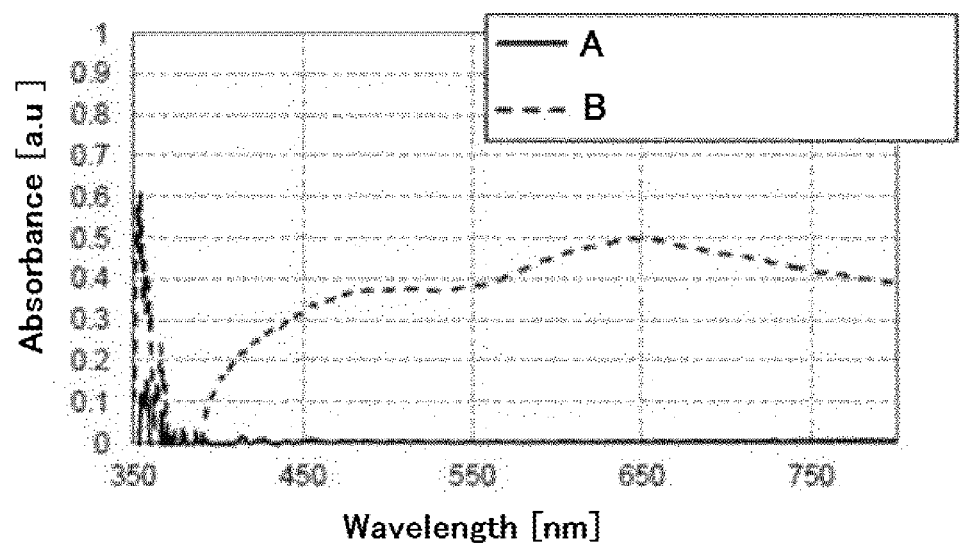
FIG. 8 is a diagram depicting absorption spectra of the discolored state and colored state of the display electrode with the electrochromic display layer produced in Example 4, where A denotes the absorption spectrum of the compound of Example 4 in the discolored state, and B denotes the absorption spectrum of the compound of Example 4 in the colored state.

An absorption spectrum was measured in the same manner as in [Coloring Discharging Comparison Test 1]. The discolored state and charged state of the absorption spectra are depicted in FIG. 8. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 5

<Synthesis of Electrochromic Compound (51) [Structural Formula (51)]>
<a> Synthesis of Intermediate (51-1)

Intermediate (51-1)

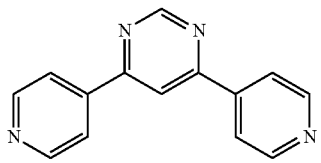

A flask was charged with 4,6-dichloropyridine (596 mg, 4 mmol), followed by being purged with argon gas. To the flask, thereafter, dioxane (60 mL), which had been deaerated with argon gas, 4-(4,4,5,5-tetramethyl-1,3,2-dioxadioxaborolan-2-yl)pyridine (8 mmol, 1.64 g), and bis(triphenylphosphine)palladium(II) dichloride (0.2 mmol, 140 mg) were added. After bubbling the solution with argon gas, a 2M potassium carbonate aqueous solution (20 mL) was added, and the resultant was heated and stirred at 100° C. for 8 hours. The resultant was filtered with Celite, and water and chloroform were added to the filtrate to separate an organic layer. Thereafter, a water layer was extracted 5 times with chloroform. The combined organic layer was washed with saturated salt water, followed by drying with sodium sulfate to condensate the filtrate, to thereby obtain a crude product. The crude product was purified by silica-gel column chromatography (eluent: chloroform/methanol=93/7 [volume ratio]), and the obtained solids were dispersed and washed in chloroform/hexane. The solids were collected by filtration, and the obtained solids were vacuum dried to thereby obtain an intermediate (51-1) as pale yellow solids (the yielded amount: 268 mg, the yield: 29%).

$^1$H NMR (500 MHz, CDCl$_3$, δ): 9.46 (d, J=1.7 Hz, 1H), 8.86 (dd, J$_1$=4.0 Hz, J$_2$=1.7 Hz, 4H), 8.21 (d, J=1.7 Hz, 1H), 8.04 (dd, J$_1$=4.6 Hz, J$_2$=1.7 Hz, 4H)

(b) Synthesis of Electrochromic Compound (51) [Structural Formula (51)]

Structural Formula (51)

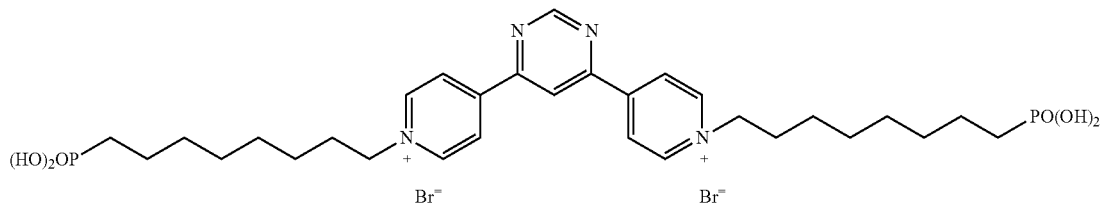

A flask was charged with the intermediate (51-1) (234 mg, 1 mmol), bromooctyl phosphonate (1.09 g, 4 mmol), DMF (10 mL), and the resultant was heated and stirred at 100° C. for 4 hours. After removing DMF under the reduced pressure, 2-propanol was added to the resultant, and the precipitated solids were collected through filtration. The solids were vacuum dried to thereby obtain a target as yellow solids. The yielded amount was 702 mg, and the yield was 90%.

[Production and Evaluation of Electrochromic Display Element]

An electrochromic display element was produced in the same manner as the method described in [Production and Evaluation of Electrochromic Display Element] of Example 1, provided that the compound (51) represented by the structural formula (51) was used as a luminescent dye.

[Coloring Discharging Comparison Test 5]

Figure 9:
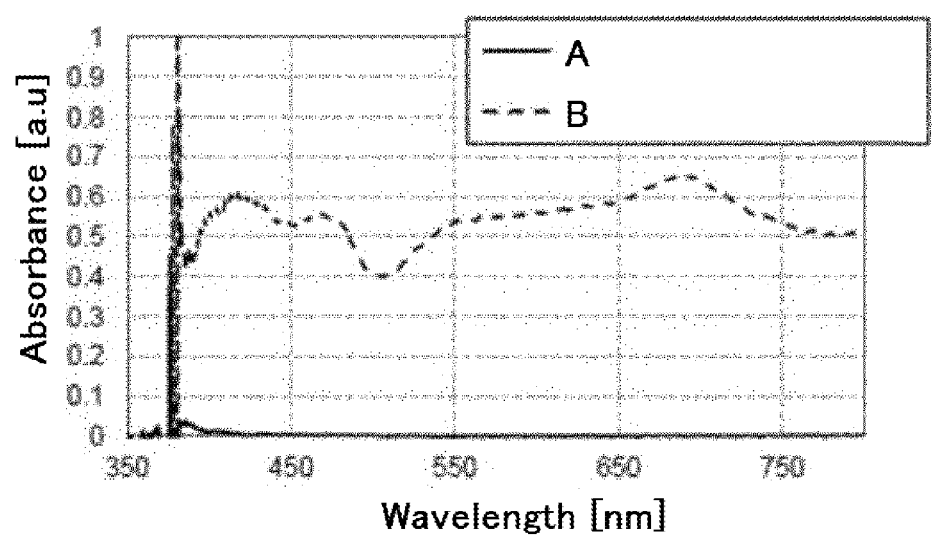
FIG. 9 is a diagram depicting absorption spectra of the discolored state and colored state of the display electrode with the electrochromic display layer produced in Example 5, where A denotes the absorption spectrum of the compound of Example 5 in the discolored state, and B denotes the absorption spectrum of the compound of Example 5 in the colored state.

An absorption spectrum was measured in the same manner as in [Coloring Discharging Comparison Test 1]. The discolored state and charged state of the absorption spectra are depicted in FIG. 9. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 6

Synthesis of Electrochromic Compound (50)
[Structural Formula (50)]

<a> Synthesis of Intermediate (50-1)

Intermediate (50-1)

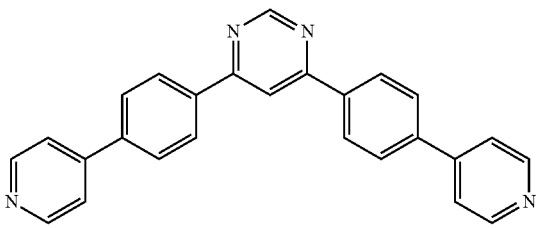

A reaction and purification were performed in the same manner as in Example 5, provided that 4-(4,4,5,5-tetramethyl-1,3,2-dioxadioxaborolan-2-yl)pyridine was replaced with 4-(4-pyridyl)phenyl boronic acid pinacol ester, to thereby obtain to thereby obtain an intermediate (50-1) (yielded amount: 592 mg, yield: 38%).

H NMR (500 MHz, CDCl$_3$, δ): 9.39 (d, J=1.8 Hz, 1H), 8.73 (dd, J$_1$=4.6 Hz, J$_2$=2.2 Hz, 4H), 8.32 (d, J=8.6 Hz, 4H), 8.22 (d, J=1.2 Hz, 1H), 7.85 (d, J=8.6 Hz, 4H), 7.60 (dd, J$_1$=4.6 Hz, J$_2$=1.2 Hz, 4H)

<b> Synthesis of Electrochromic Compound (50) [Structural Formula (50)]

Structural Formula (50)

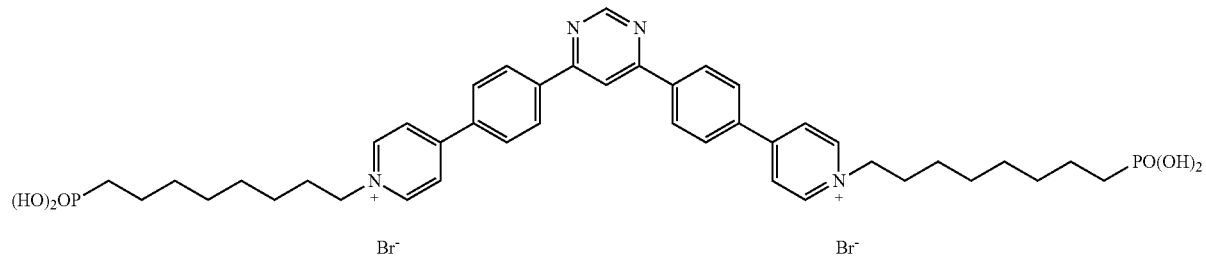

A reaction and purification were carried out in the same manner as in Example 5, to thereby obtain a target (yielded amount: 830 mg, yield: 89%).

[Production and Evaluation of Electrochromic Display Element]

An electrochromic display element was produced in the same manner as the method described in [Production and Evaluation of Electrochromic Display Element] of Example 1, provided that the compound (50) represented by the structural formula (50) was used as a luminescent dye.

[Coloring Discharging Comparison Test 6]

Figure 10:
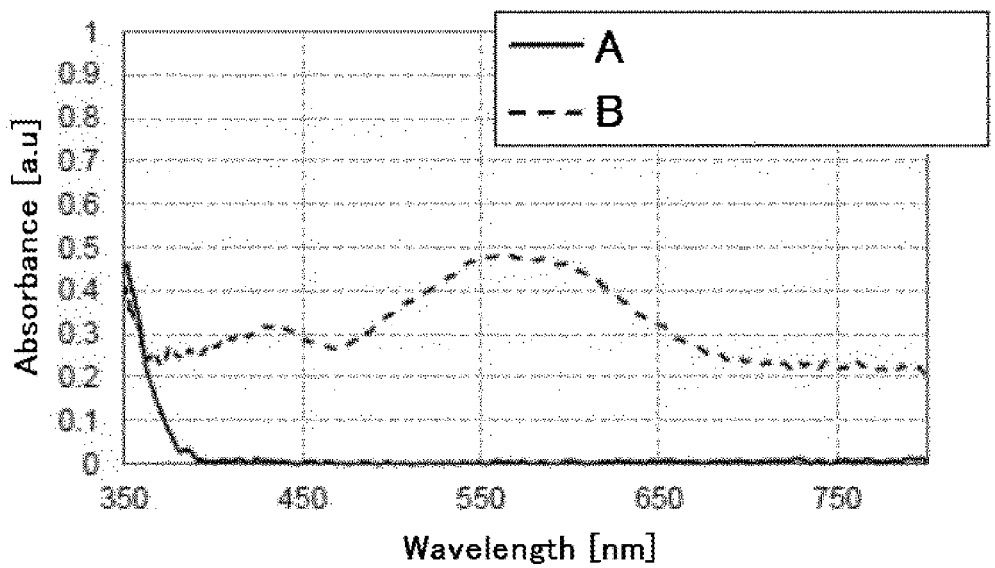
FIG. 10 is a diagram depicting absorption spectra of the discolored state and colored state of the display electrode with the electrochromic display layer produced in Example 6, where A denotes the absorption spectrum of the compound of Example 6 in the discolored state, and B denotes the absorption spectrum of the compound of Example 6 in the colored state.

An absorption spectrum was measured in the same manner as in [Coloring Discharging Comparison Test 1]. The discolored state and charged state of the absorption spectra are depicted in FIG. 10. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 7

Synthesis of Electrochromic Compound (78) [Structural Formula (78)]

<a> Synthesis of Intermediate (78-1)

Intermediate (78-1)

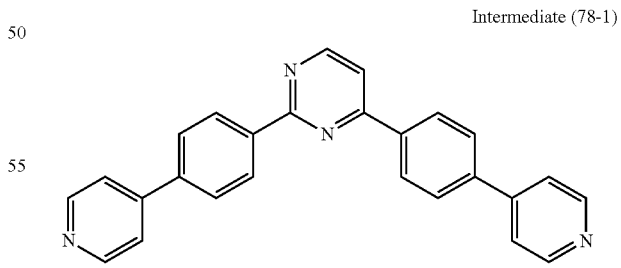

A reaction and purification were carried out in the same manner as in Example 6, provided that 4,6-dichloropyridine was replaced with 2,4-dichloropyridine, to thereby obtain an intermediate (78-1). The yielded amount was 1.39 g, and the yield was 90%.

$^1$H NMR (500 MHz, CDCl$_3$, δ): 8.92 (d, J=5.7 Hz, 1H), 8.71-8.74 (m, 6H), 8.38 (dd, J$_1$=6.3 Hz, J$_2$=1.7 Hz 2H), 7.82-7.85 (m, 4H), 7.70 (d, J=5.3 Hz, 1H), 7.59-7.62 (m, 4H)

\<b\> Synthesis of Electrochromic Compound (78) [Structural Formula (78)]

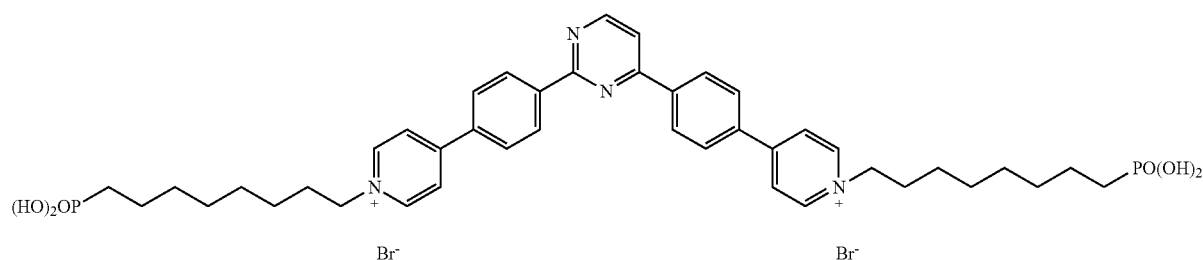

Structural Formula (78)

A reaction and purification were carried out in the same manner as in Example 5 to thereby obtain a target (yielded amount: 793 mg, yield: 85%).

[Production and Evaluation of Electrochromic Display Element]

An electrochromic display element was produced in the same manner as the method described in [Production and Evaluation of Electrochromic Display Element] of Example 1, provided that the compound (78) represented by the structural formula (78) was used as a luminescent dye.

[Coloring Discharging Comparison Test 7]

Figure 11:
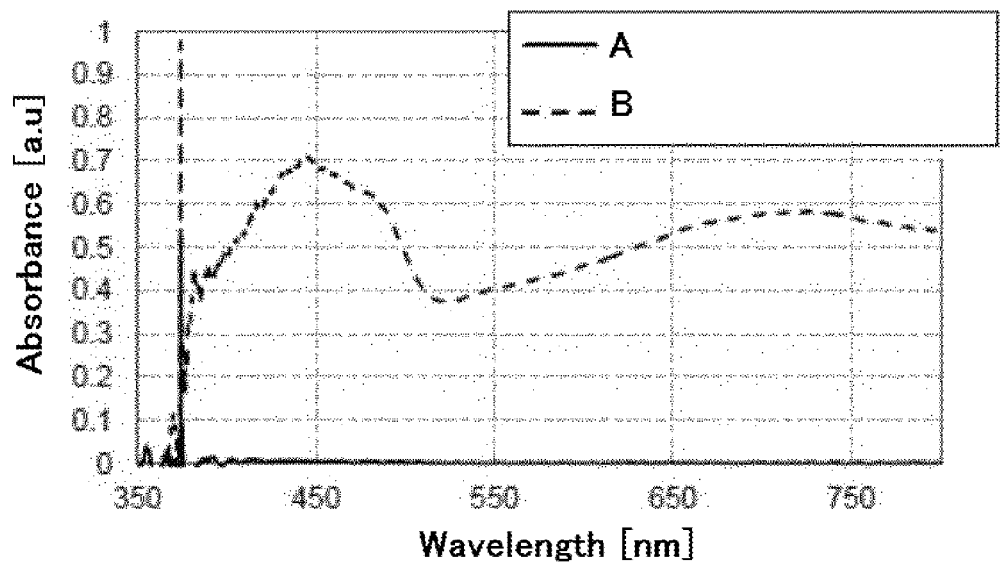
FIG. 11 is a diagram depicting absorption spectra of the discolored state and colored state of the display electrode with the electrochromic display layer produced in Example 7, where A denotes the absorption spectrum of the compound of Example 7 in the discolored state, and B denotes the absorption spectrum of the compound of Example 7 in the colored state.

An absorption spectrum was measured in the same manner as in [Coloring Discharging Comparison Test 1]. The discolored state and charged state of the absorption spectra are depicted in FIG. 11. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 8

Synthesis of Electrochromic Compound (79) [Structural Formula (79)]

\<a\> Synthesis of Intermediate (79-1)

Intermediate (79-1)

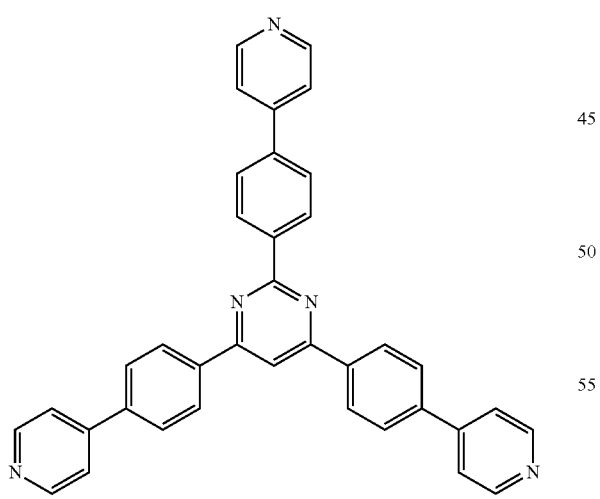

A reaction and purification were carried out in the same manner as in Example 6, provided that 4,6-dichloropyridine was replaced with 2,4,6-trichloropyridine, to thereby obtain an intermediate (79-1). The yielded amount was 1.56 g, and the yield was 72%.

$^1$H NMR (500 MHz, CDCl$_3$, δ): 8.87 (d, J=8.6 Hz, 2H), 8.75-8.72 (m, 6H), 8.15 (s, 1H), 8.46 (d, J=8.6 Hz, 4H), 7.89-7.85 (m, 6H), 7.64-7.61 (m, 6H)

<b> Synthesis of Electrochromic Compound (79) [Structural Formula (79)]

Structural Formula (79)

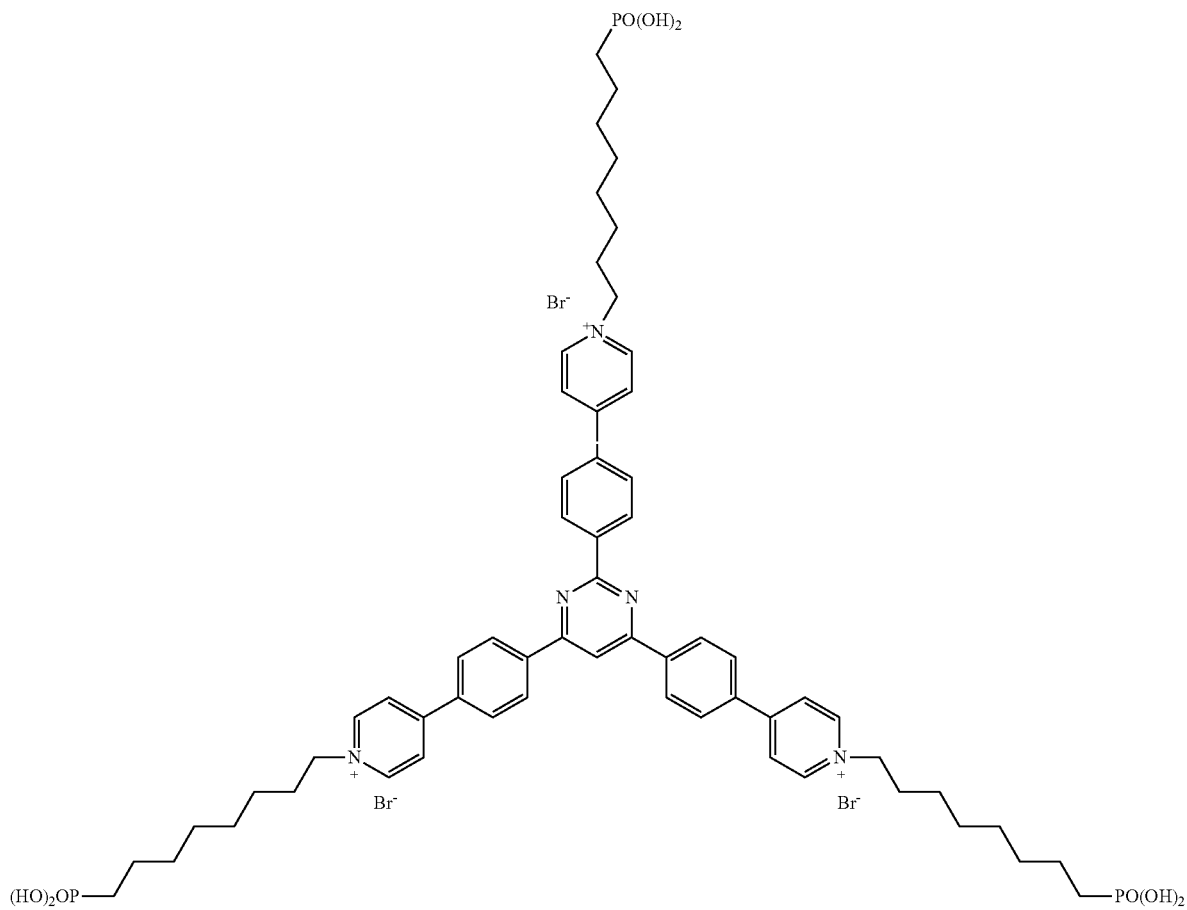

A reaction and purification were carried out in the same manner as in Example 5, to thereby obtain a target (yielded amount: 1.09 g, yield: 80%).

[Production and Evaluation of Electrochromic Display Element]

An electrochromic display element was produced in the same manner as the method described in [Production and Evaluation of Electrochromic Display Element] of Example 1, provided that the compound (79) represented by the structural formula (79) was used as a luminescent dye.

[Coloring Discharging Comparison Test 8]

Figure 12:
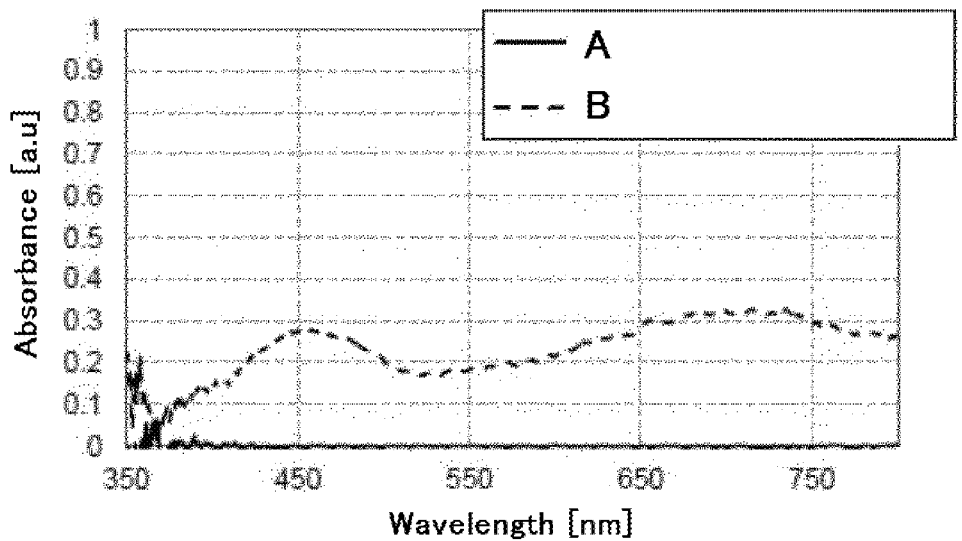
FIG. 12 is a diagram depicting absorption spectra of the discolored state and colored state of the display electrode with the electrochromic display layer produced in Example 8, where A denotes the absorption spectrum of the compound of Example 8 in the discolored state, and B denotes the absorption spectrum of the compound of Example 8 in the colored state.

An absorption spectrum was measured in the same manner as in [Coloring Discharging Comparison Test 1]. The discolored state and charged state of the absorption spectra are depicted in FIG. 12. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 9

Synthesis of Electrochromic Compound (44)(Structural Formula (44)]

<a> Synthesis of Intermediate (44-1)

Intermediate (44-1)

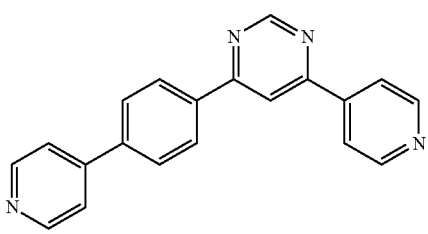

A flask was charged with 4,6-dichloropyridine (596 mg, 4.0 mmol), followed by being purged with argon gas. To the flask, thereafter, dioxane (60 mL), which had been deaerated with argon gas, 4-(4-pyridyl)phenyl boronic acid pinacol ester (4.0 mmol, 2.26 g), bis(triphenylphosphine)palladium (II) dichloride (0.3 mmol, 210 mg) were added. After bubbling the solution with argon gas, 2M $K_2CO_3$ (20 mL) was added, and the resultant was heated and stirred at 50° C. for 4 hours. Subsequently, 4-(4,4,5,5-tetramethyl-1,3,2-dioxaborolan-2-yl)pyridine (4 mmol, 820 mg) was added, and the resulting mixture was heated and stirred at 100° C. for 4 hours. The resultant was filtered with Celite, and water and chloroform were added to the filtrate to separate an organic layer. Thereafter, a water layer was extracted 5 times with chloroform. The combined organic layer was washed with saturated salt water, followed by drying with sodium sulfate to condensate the filtrate, to thereby obtain a crude product. The crude product was purified by silica-gel column chromatography (eluent: chloroform/methanol=93/7), and the obtained solids were dispersed and washed in chloroform/hexane. The solids were collected by filtration, and the obtained solids were vacuum dried to thereby obtain an intermediate (44-1) as pale yellow solids (the yielded amount: 892 mg, the yield: 72%).

$^1$H NMR (500 MHz, CDCl$_3$, δ): 9.42 (d, J=1.7 Hz, 1H), 8.85 (dd, J$_1$=5.8 Hz, J$_2$=1.8 Hz, 2H), 8.73 (dd, J$_1$=6.3 Hz, J$_2$=1.7 Hz, 2H), 8.31 (d, J=8.6 Hz, 2H), 8.21 (d, J=1.7 Hz, 1H), 8.04 (dd, J$_1$=6.3 Hz, J$_2$=1.7 Hz, 2H), 7.84 (d, J=6.9 Hz, 2H), 7.59 (d, J$_1$=5.8 Hz, J$_2$=1.8 Hz, 2H)

<b> Synthesis of Electrochromic Compound (44) [Structural Formula (44)]

Structural Formula (44)

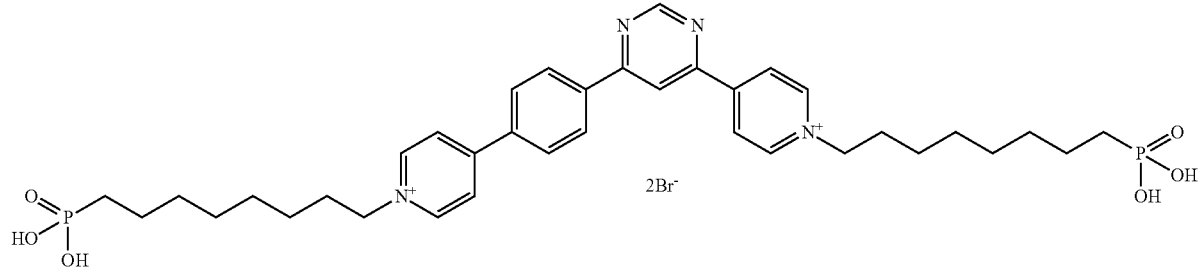

A reaction and purification were carried out in the same manner as in Example 5, to thereby obtain a target (yielded amount: 771 mg, yield: 90%).

[Production and Evaluation of Electrochromic Display Element]

An electrochromic display element was produced in the same manner as the method described in [Production and Evaluation of Electrochromic Display Element] of Example 1, provided that the compound (44) represented by the structural formula (44) was used as a luminescent dye.

[Coloring Discharging Comparison Test 9]

Figure 13:
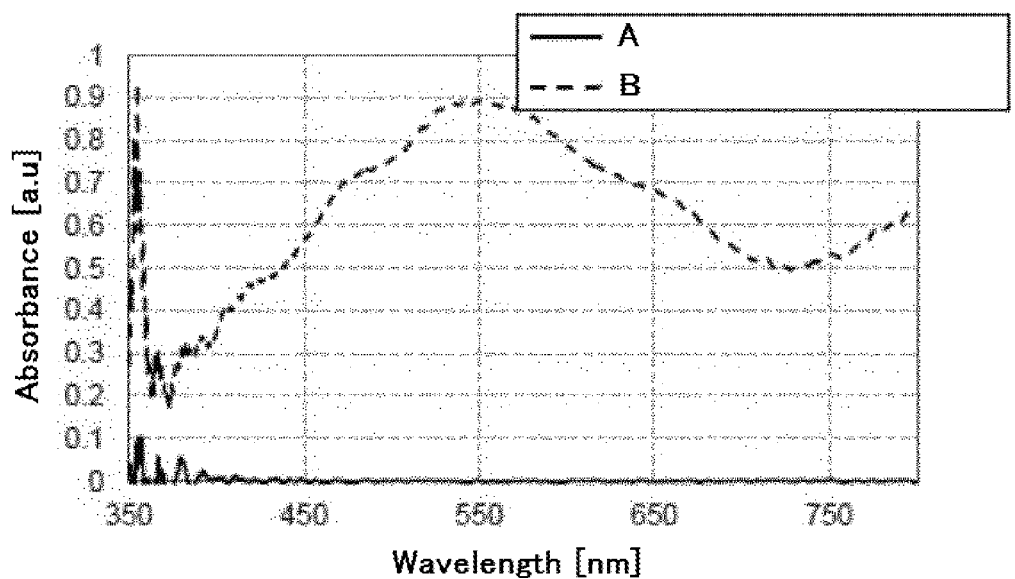
FIG. 13 is a diagram depicting absorption spectra of the discolored state and colored state of the display electrode with the electrochromic display layer produced in Example 9, where A denotes the absorption spectrum of the compound of Example 9 in the discolored state, and B denotes the absorption spectrum of the compound of Example 9 in the colored state.

An absorption spectrum was measured in the same manner as in [Coloring Discharging Comparison Test 1]. The discolored state and charged state of the absorption spectra are depicted in FIG. 13. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 10

Synthesis of Electrochromic Compound [Structural Formula (80)]

<a> Synthesis of Intermediate (80-1)

Intermediate (80-1)

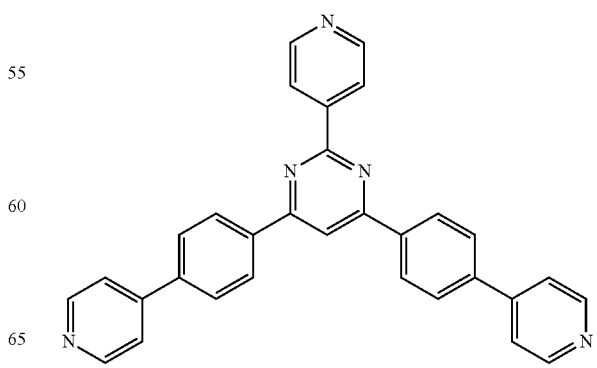

A flask was charged with 2,4,6-trichloropyridine (732 mg, 4.0 mmol), followed by being purged with argon gas. To the flask, thereafter, dioxane (60 mL), which had been deaerated with argon gas, 4-(4-pyridyl)phenyl boronic acid pinacol ester (8.0 mmol, 2.26 g), and bis(triphenylphosphine)palladium(II) dichloride (0.3 mmol, 210 mg) were added. After bubbling the solution with argon gas, 2M $K_2CO_3$ (20 mL) was added, and the resultant was heated and stirred at 50° C. for 4 hours. Next, 4-4,4,5,5-tetramethyl-1,3,2-dioxaborolan-2-yl)pyridine (4 mmol, 820 mg) was added and the resultant was heated and stirred at 100° C. for 4 hours. Subsequently, the resultant was filtered with Celite, and water and chloroform were added to the filtrate to separate an organic layer. Thereafter, a water layer was extracted 5 times with chloroform. The combined organic layer was washed with saturated salt water, followed by drying with sodium sulfate to condensate the filtrate, to thereby obtain a crude product. The crude product was purified by silica-gel column chromatography (eluent: chloroform/methanol=93/7), and the obtained solids were dispersed and washed in chloroform/hexane. The solids were collected by filtration, and the obtained solids were vacuum dried to thereby obtain an intermediate (80-1) as pale yellow solids (the yielded amount: 1.19 g, the yield: 64%).

$^1$H NMR (500 MHz, $CDCl_3$, δ): 8.87 (dd, $J_1$=4.7 Hz, $J_2$=1.7 Hz, 2H), 8.75 (dd, $J_1$=4.0 Hz, $J_2$=1.7 Hz, 4H), 8.58 (dd, $J_1$=4.7 Hz, $J_2$=1.7 Hz, 2H), 8.45 (dt $J_1$=8.0 Hz, $J_2$=1.7 Hz, 4H), 8.21 (s, 1H), 7.88 (dd, $J_1$=8.6 Hz, $J_2$=1.7 Hz, 4H), 7.61 (dd, $J_1$=4.7 Hz, $J_2$=1.7 Hz, 4H)

<b> Synthesis of Electrochromic Compound [Structural Formula (80)]

A reaction and purification were carried out in the same manner as in Example 5 to thereby obtain a target (the yielded amount: 1.06 g, the yield: 83%).

[Production and Evaluation of Electrochromic Display Element]

An electrochromic display element was produced in the same manner as the method described in [Production and Evaluation of Electrochromic Display Element] of Example 1, provided that the compound (80) represented by the structural formula (80) was used as a luminescent dye.

[Coloring Discharging Comparison Test 10]

Figure 14:
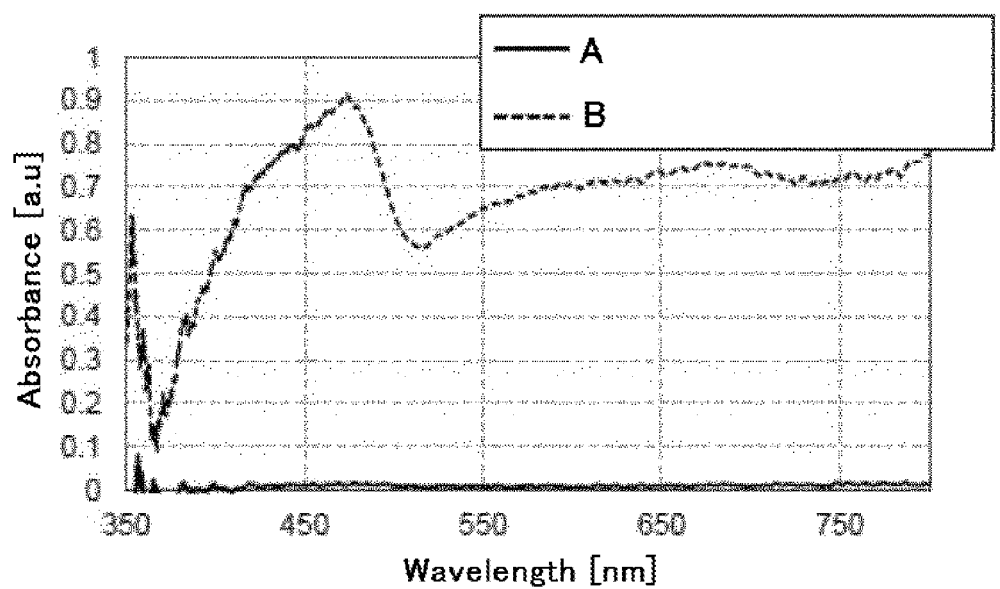
FIG. 14 is a diagram depicting absorption spectra of the discolored state and colored state of the display electrode with the electrochromic display layer produced in Example 10, where A denotes the absorption spectrum of the compound of Example 10 in the discolored state, and B denotes the absorption spectrum of the compound of Example 10 in the colored state.

An absorption spectrum was measured in the same manner as in [Coloring Discharging Comparison Test 1]. The discolored state and charged state of the absorption spectra are depicted in FIG. 14. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Structural Formula (80)

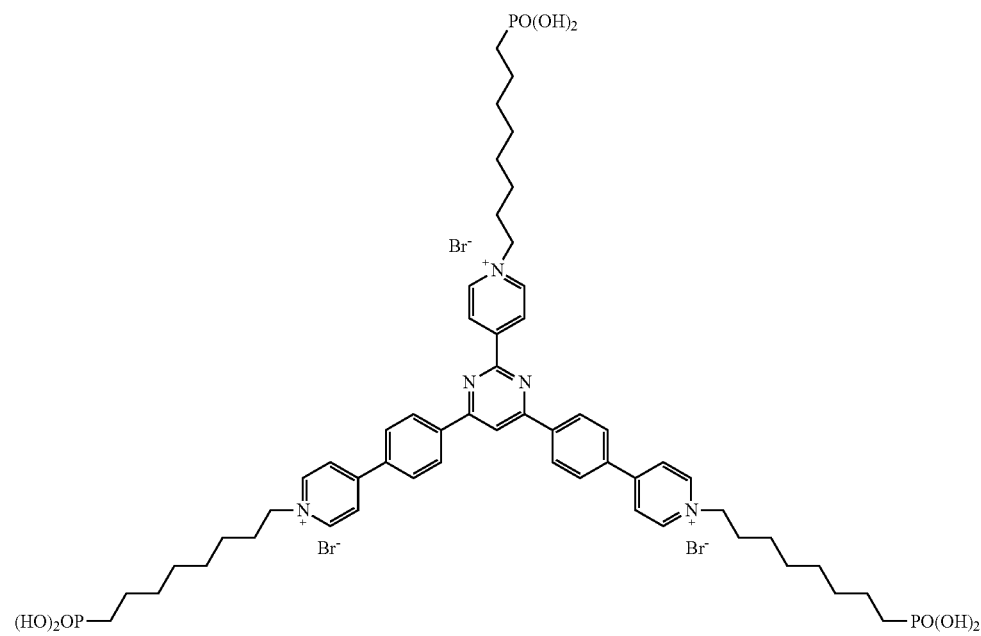

Example 11

Synthesis of Electrochromic Compound (36)
[Structural Formula (36)]

<a> Synthesis of Intermediate (36-1)

Intermediate (36-1)

An intermediate (36-1) was obtained by carrying out a reaction and purification in the same manner as in Example 9, provided that the intermediate (44-1) used in Example 9 was replaced with the intermediate (50-1) obtained in Example 6, and 4-(4,4,5,5-tetramethyl-1,3,2-dioxaborolan-2-yl)pyridine was replaced with 4-(trifluoromethyl)phenyl boronate. The yielded amount was 740 mg, and the yield was 65%.

<b> Synthesis of Electrochromic Compound (36) [Structural Formula (36)]

A reaction and purification were carried out in the same manner as in Example 5, to thereby obtain a target (the yielded amount: 915 g, the yield: 85%).

[Production and Evaluation of Electrochromic Display Element]

An electrochromic display element was produced in the same manner as the method described in [Production and Evaluation of Electrochromic Display Element] of Example 1, provided that the compound (36) represented by the structural formula (36) was used as a luminescent dye.

[Coloring Discharging Comparison Test 11]

Figure 15:
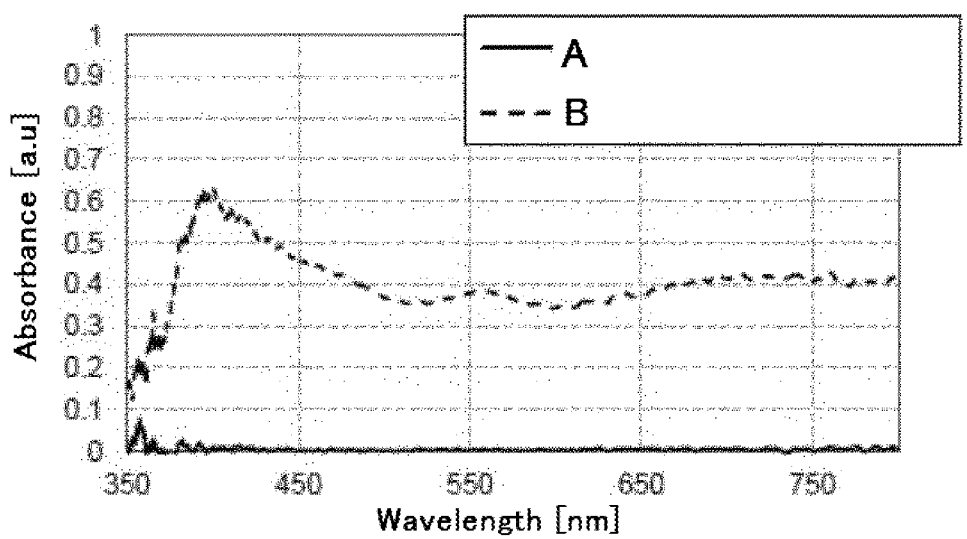
FIG. 15 is a diagram depicting absorption spectra of the discolored state and colored state of the display electrode with the electrochromic display layer produced in Example 11, where A denotes the absorption spectrum of the compound of Example 11 in the discolored state, and B denotes the absorption spectrum of the compound of Example 11 in the colored state.

An absorption spectrum was measured in the same manner as in [Coloring Discharging Comparison Test 1]. The discolored state and charged state of the absorption spectra are depicted in FIG. 15. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 12

Synthesis of Electrochromic Compound (38)
[Structural Formula (38)]

<a> Synthesis of Intermediate (38-1)

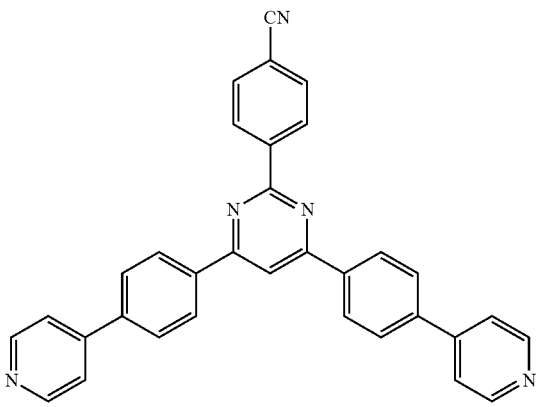

Intermediate (38-1)

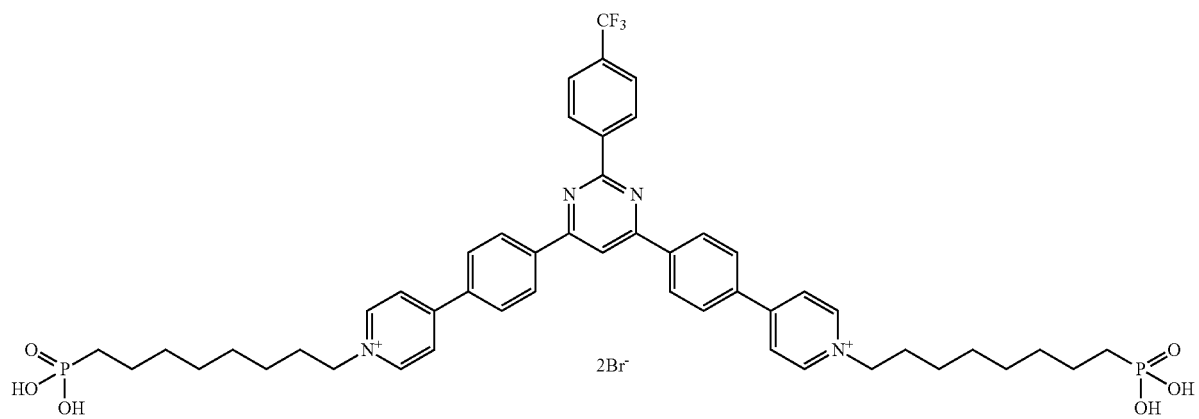

Structural Formula (36)

An intermediate (38-1) was obtained by carrying out a reaction and purification in the same manner as in Example 9, provided that the intermediate (44-1) used in Example 9 was replaced with the intermediate (50-1) obtained in Example 6, and 4-(4,4,5,5-tetramethyl-1,3,2-dioxaborolan-2-yl)pyridine was replaced with 4-(cyano)phenyl boronate. The yielded amount was 304 mg, and the yield was 16%.

<b> Synthesis of Electrochromic Compound (38) [Structural Formula (38)]

Structural Formula (38)

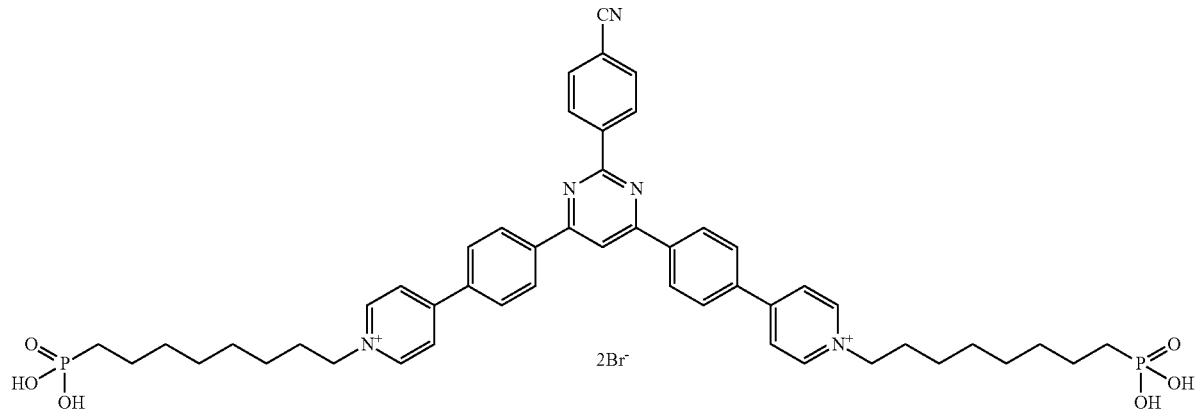

A reaction and purification were carried out in the same manner as in Example 5, to thereby obtain a target (the yielded amount: 919 mg, the yield: 89%)

[Production and Evaluation of Electrochromic Display Element]

An electrochromic display element was produced in the same manner as the method described in [Production and Evaluation of Electrochromic Display Element] of Example 1, provided that the compound (38) represented by the structural formula (38) was used as a luminescent dye.

[Coloring Discharging Comparison Test 12]

Figure 16:
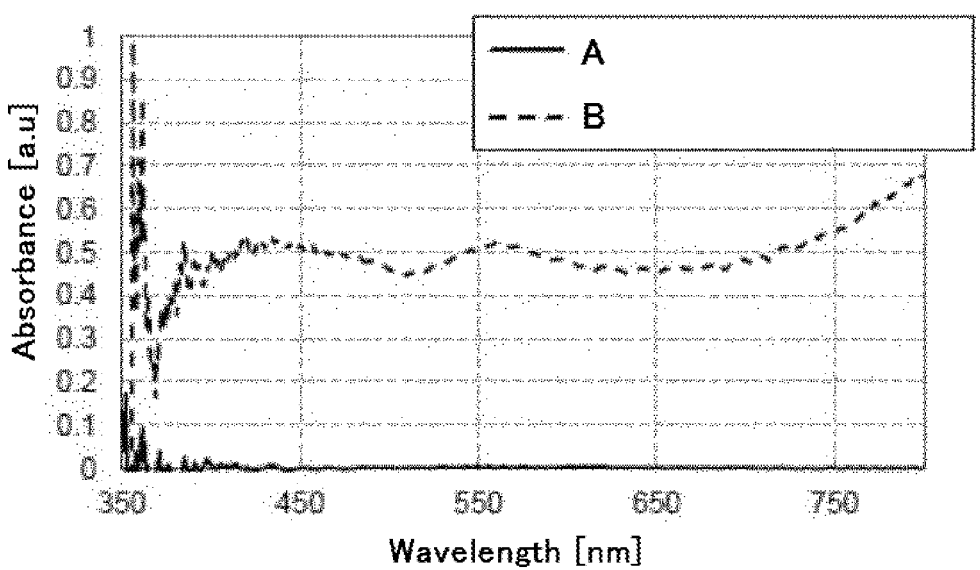
FIG. 16 is a diagram depicting absorption spectra of the discolored state and colored state of the display electrode with the electrochromic display layer produced in Example 12, where A denotes the absorption spectrum of the compound of Example 12 in the discolored state, and B denotes the absorption spectrum of the compound of Example 12 in the colored state.

An absorption spectrum was measured in the same manner as in [Coloring Discharging Comparison Test 1]. The discolored state and charged state of the absorption spectra are depicted in FIG. 16. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 13

Synthesis of Electrochromic Compound (42) [Structural Formula (42)]

<a> Synthesis of Intermediate (42-1)

Intermediate (42-1)

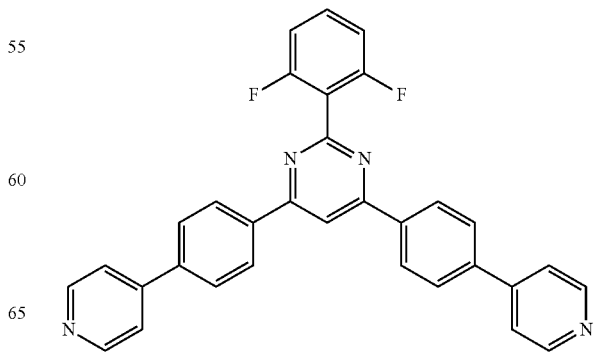

An intermediate (42-1) was obtained by carrying out a reaction and purification in the same manner as in Example 9, provided that the intermediate (44-1) used in Example 9 was replaced with the intermediate (50-1) obtained in Example 6, and 4-(4,4,5,5-tetramethyl-1,3,2-dioxaborolan-2-yl)pyridine was replaced with 4-(2,6-difluoro)phenyl boronate. The yielded amount was 396 mg, and the yield was 21%.

<b> Synthesis of Electrochromic Compound (42) [Structural Formula (42)]

Structural Formula (42)

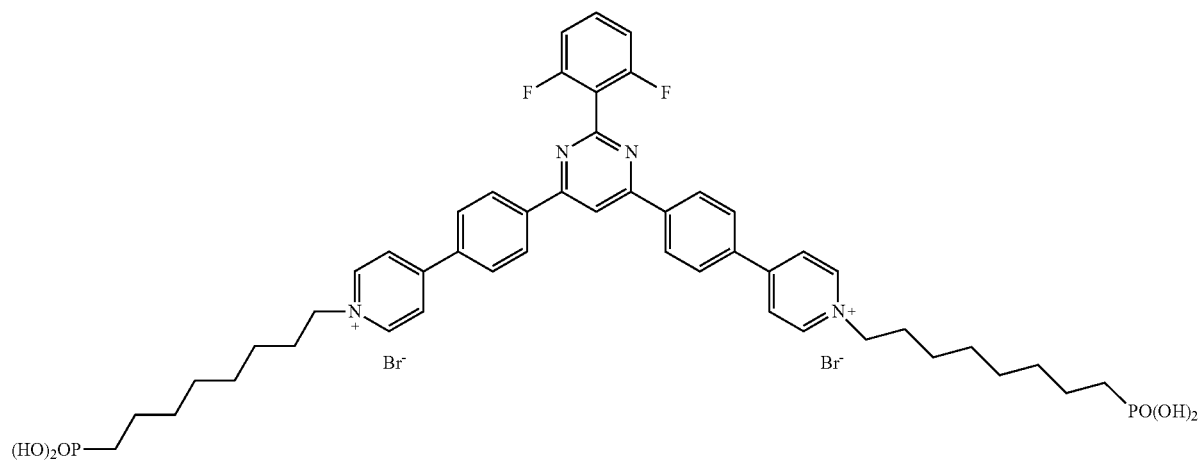

A reaction and purification were carried out in the same manner as in Example 5, to thereby obtain a target (the yielded amount: 835 mg, the yield: 80%)

[Production and Evaluation of Electrochromic Display Element]

An electrochromic display element was produced in the same manner as the method described in [Production and Evaluation of Electrochromic Display Element] of Example 1, provided that the compound (42) represented by the structural formula (42) was used as a luminescent dye.

[Coloring Discharging Comparison Test 13]

Figure 17:
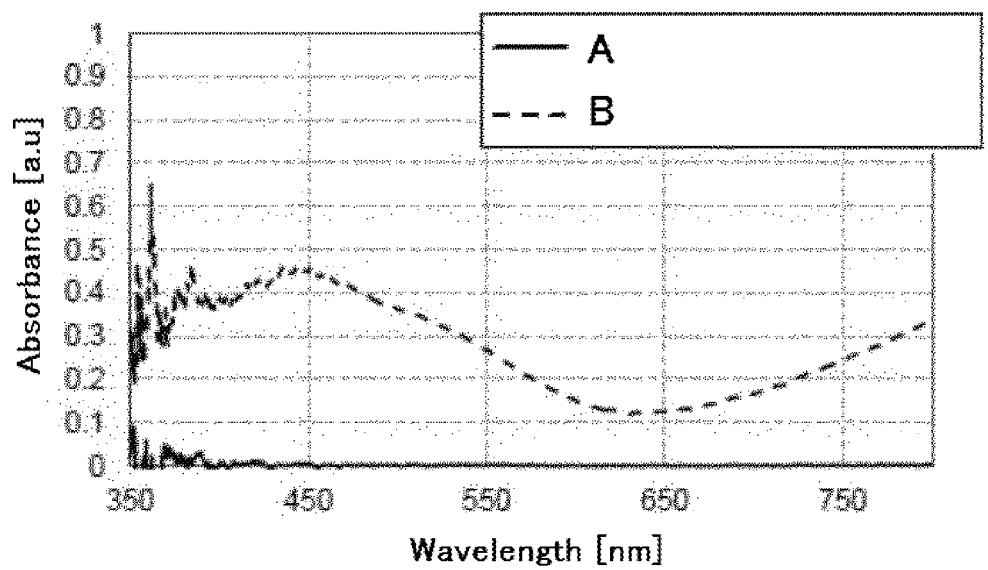
FIG. 17 is a diagram depicting absorption spectra of the discolored state and colored state of the display electrode with the electrochromic display layer produced in Example 13, where A denotes the absorption spectrum of the compound of Example 13 in the discolored state, and B denotes the absorption spectrum of the compound of Example 13 in the colored state.

An absorption spectrum was measured in the same manner as in [Coloring Discharging Comparison Test 1]. The discolored state and charged state of the absorption spectra are depicted in FIG. 17. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 14

Synthesis of Electrochromic Compound (31) [Structural Formula (31)]

<a> Synthesis of Intermediate (31-1)

Intermediate (31-1)

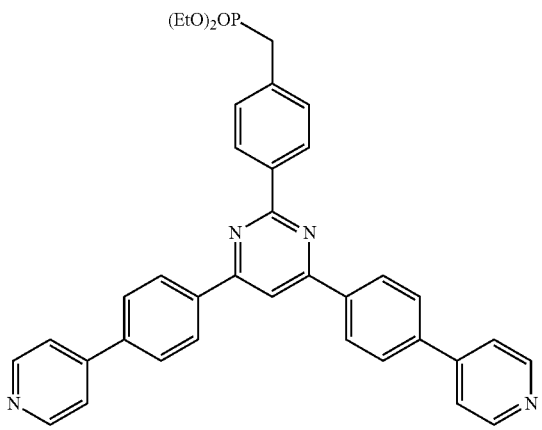

An intermediate (31-1) was obtained by carrying out a reaction and purification in the same manner as in Example 9, provided that the intermediate (44-1) used in Example 9 was replaced with the intermediate (50-1) obtained in Example 6, and 4-(4,4,5,5-tetramethyl-1,3,2-dioxaborolan-2-yl)pyridine was replaced with the compound represented by the following structural formula. The yielded amount was 1.74 g, and the yield was 73%.

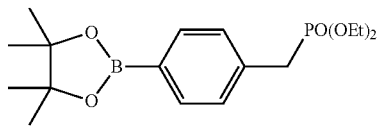

<b> Synthesis of Intermediate (31-2)

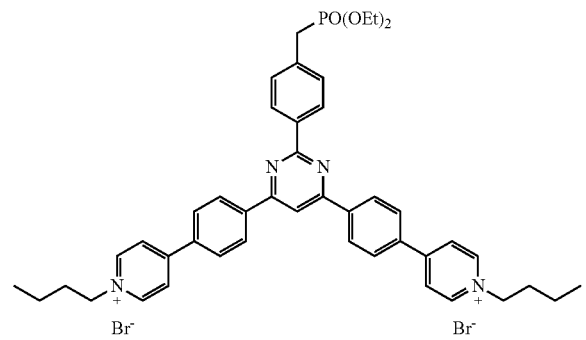

Intermediate (31-2)

A flask was charged with the above-synthesized intermediate (31-1) (0.338 mmol, 207 mg), n-butylbromide (1.35 mmol, 184 mg), DMF (15 mL), and the resulting mixture was stirred at 85° C. for 12 hours. DMF was removed from the mixture under the reduced pressure, and acetone was added to the resultant. The precipitated solids were then separated by filtration, and the solids were dried under the reduced pressure to thereby obtain an intermediate (31-2). The yielded amount was 278 mg, and the yield was 92%.

<c> Synthesis of Electrochromic Compound (31) [Structural Formula (31)]

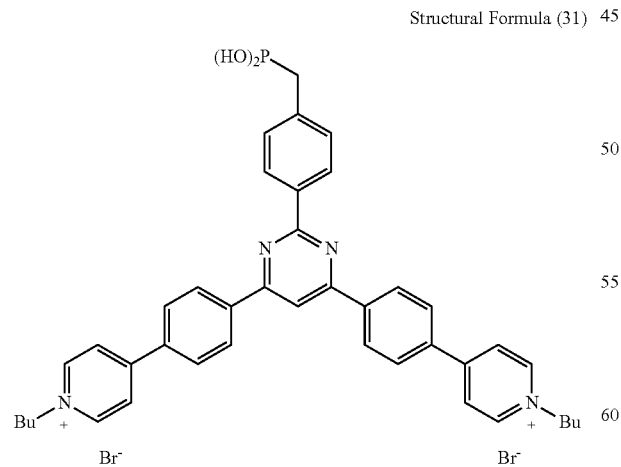

Structural Formula (31)

A flask was charged with the intermediate (31-2) (277 mg, 0.312 mmol), and chloroform (50 mL). to this, trimethylsilyl bromide (50 mL) was added dropwise, and the resulting mixture was stirred for 16 hours at room temperature. From the resultant, chloroform was removed under the reduced pressure. To this, methanol was added, and the mixture was stirred for 1 hour. From the resultant, methanol was removed under the reduced pressure, and acetone was added to the resultant to precipitate solids. The solids were collected through filtration, to thereby obtain a target. The yielded amount was 204 mg, and the yield was 78%.

$^1$H NMR (500 MHz, CDCl$_3$, δ): 9.20 (d, J=6.9 Hz, 4H), 8.85 (s, 1H), 8.80 (d, J=8.6 Hz, 4H), 8.69 (d, J=6.9 Hz, 4H), 8.61 (d, J=8.0 Hz, 2H), 8.36 (d, J=8.6 Hz, 4H), 7.51 (dd, J$_1$=6.3 Hz, J$_2$=2.3 Hz, 2H), 4.64 (t, J=6.9 Hz, 4H), 3.12 (d, J=21.8 Hz, 2H), 1.96 (quint, J=7.5 Hz, 4H), 1.37 (quint, J=7.5 Hz, 4H), 0.96 (t, J=7.5 Hz, 6H)

[Production and Evaluation of Electrochromic Display Element]

An electrochromic display element was produced in the same manner as the method described in [Production and Evaluation of Electrochromic Display Element] of Example 1, provided that the compound (31) represented by the structural formula (31) was used as a luminescent dye.

[Coloring Discharging Comparison Test 14]

Figure 18:
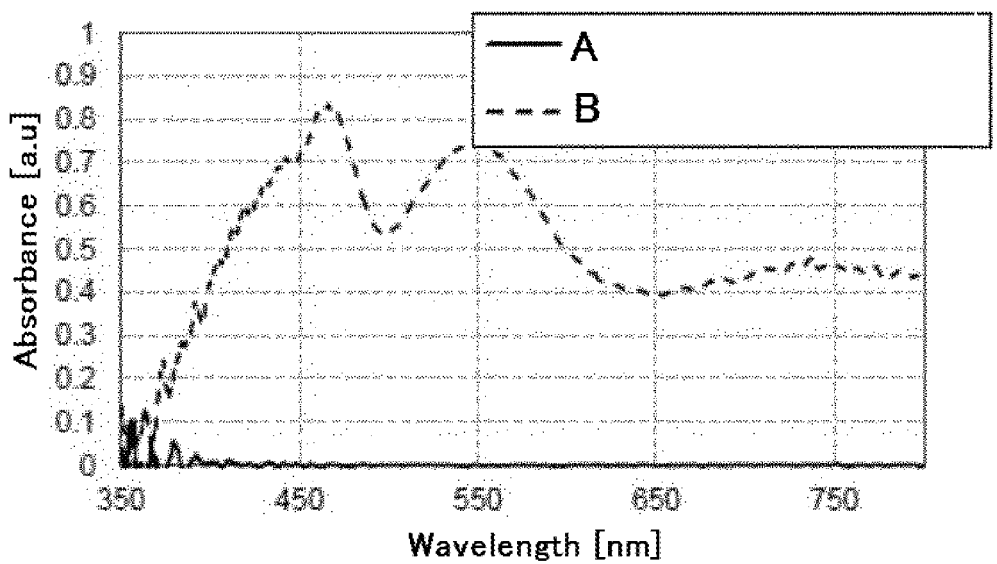
FIG. 18 is a diagram depicting absorption spectra of the discolored state and colored state of the display electrode with the electrochromic display layer produced in Example 14, where A denotes the absorption spectrum of the compound of Example 14 in the discolored state, and B denotes the absorption spectrum of the compound of Example 14 in the colored state.

An absorption spectrum was measured in the same manner as in [Coloring Discharging Comparison Test 1]. The discolored state and charged state of the absorption spectra are depicted in FIG. 18. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 15

Synthesis of Electrochromic Compound [Structural Formula (35)]

<a> Synthesis of Intermediate (35-1)

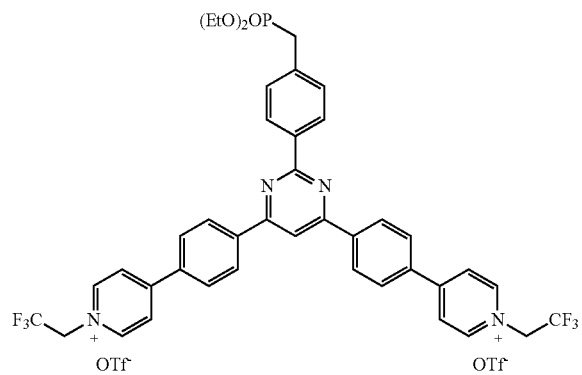

Structural Formula (35-1)

An intermediate (35-1) was obtained by carrying out a reaction and purification in the same manner as in Example 14, provided that, in (b) of Example 14, n-butyl bromide was replaced with 2,2,2-trifluoroethyl trifluoromethane sulfonate.

The yielded amount was 132 mg, and the yield was 60%.

\<c\> Synthesis of Electrochromic Compound (35) [Structural Formula (35)]

Structural Formula (35)

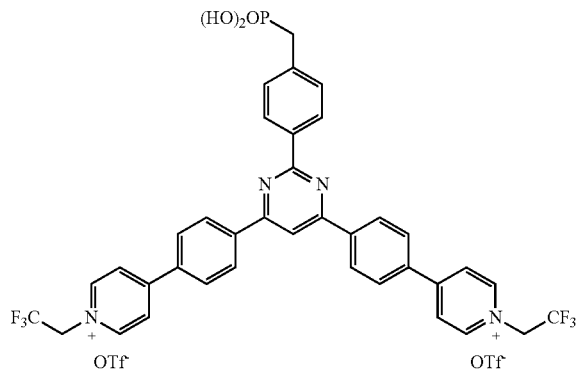

A target was obtained by carrying out a reaction and purification in the same manner as in Example 14, provided that, in (c) of Example 14, the intermediate (31-2) was replaced with the intermediate (35-1). The yielded amount was 119 mg, and the yield was 95%. In the Structural Formulae, "OTf⁻" represents the following triflate anion:

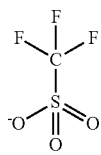

and "OTf" means trifluoromethanesulfonic acid.

$^1$H NMR (500 MHz, CDCl$_3$, δ): 9.30 (d, J=6.3 Hz, 4H), 8.83-8.88 (m, 9H), 8.62 (d, J=8.0 Hz, 2H), 8.40 (d, J=8.6 Hz, 4H), 7.52 (dd, J$_1$=8.0 Hz, J$_2$=1.7 Hz, 2H), 5.86 (q, J=8.6 Hz, 4H), 3.13 (d, J=21.2 Hz, 2H)

[Production and Evaluation of Electrochromic Display Element]

An electrochromic display element was produced in the same manner as the method described in [Production and Evaluation of Electrochromic Display Element] of Example 1, provided that the compound (35) represented by the structural formula (35) was used as a luminescent dye.

[Coloring Discharging Comparison Test 15]

Figure 19:
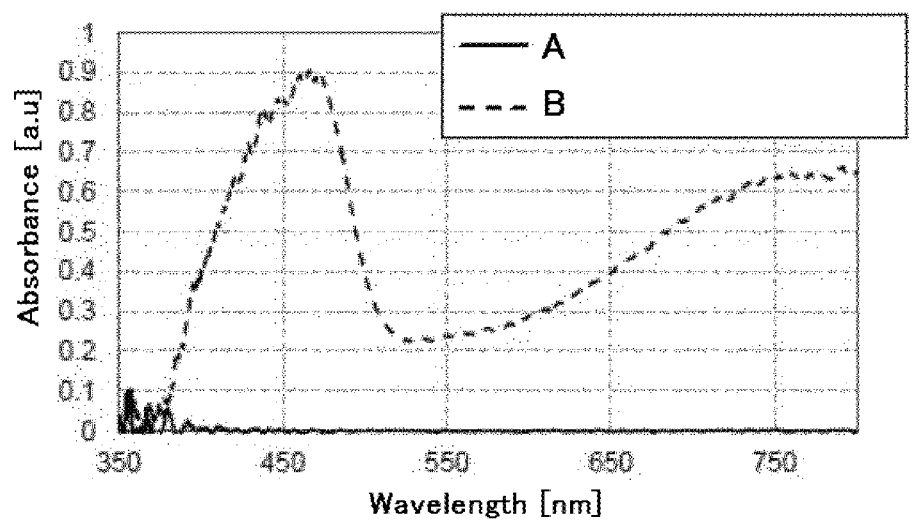
FIG. 19 is a diagram depicting absorption spectra of the discolored state and colored state of the display electrode with the electrochromic display layer produced in Example 15, where A denotes the absorption spectrum of the compound of Example 15 in the discolored state, and B denotes the absorption spectrum of the compound of Example 15 in the colored state.

An absorption spectrum was measured in the same manner as in [Coloring Discharging Comparison Test 1]. The discolored state and charged state of the absorption spectra are depicted in FIG. 19. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 16

Synthesis of Electrochromic Compound [Structural Formula (56)]

\<a\> Synthesis of Intermediate (56-1)

Intermediate (56-1)

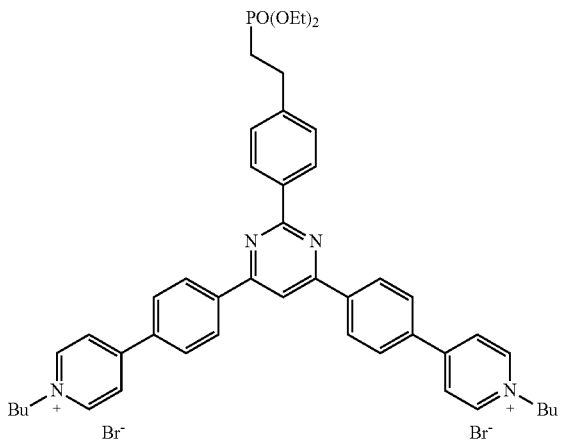

An intermediate (56-1) was obtained by carrying out a reaction and purification in the same manner as in Example 9, provided that the intermediate (44-1) used in Example 9 was replaced with the intermediate (50-1) obtained in Example 6, and 4-(4,4,5,5-tetramethyl-1,3,2-dioxaborolan-2-yl)pyridine was replaced with the compound represented by the following structural formula. The yielded amount was 1.86 g, and the yield was 74%.

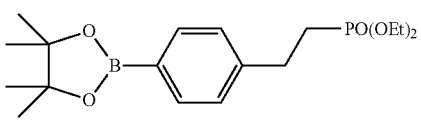

\<a\> Synthesis of Intermediate (56-2)

Intermediate (56-2)

An intermediate (56-2) was obtained by carrying out a reaction and purification in the same manner as in Example 14, provided that, in (b) of Example 14, the intermediate (31-1) was replaced with the intermediate (56-1). The yielded amount was 304 mg, and the yield was 90%.

<c> Synthesis of Electrochromic Compound (56) [Structural Formula (56)]

Structural Formula (56)

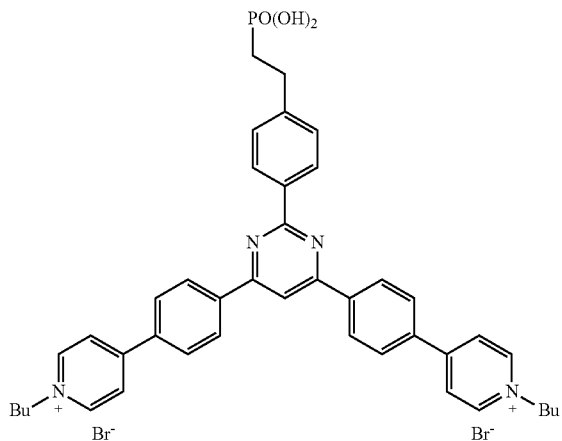

A target was obtained by carrying out a reaction and purification in the same manner as in Example 14, provided that, in (c) of Example 14, the intermediate (31-2) was replaced with the intermediate (56-2). The yielded amount was 244 mg, and the yield was 95%.

$^1$H NMR (500 MHz, CDCl$_3$, δ) 9.21 (d, J=7.5 Hz, 4H), 8.85 (s, 1H), 8.80 (d, J=8.6 Hz, 4H), 8.69 (d, J=6.9 Hz, 4H), 8.62 (d, J=8.0 Hz, 2H), 8.36 (d, J=8.6 Hz, 4H), 7.51 (d, J=8.0 Hz, 2H), 4.65 (t, J=7.5 Hz, 4H), 2.92 (quint, J=4.6 Hz, 2H), 1.95-2.00 (m, 4H). 0.96 (t, J=6.9 Hz, 6H)

[Production and Evaluation of Electrochromic Display Element]

An electrochromic display element was produced in the same manner as the method described in [Production and Evaluation of Electrochromic Display Element] of Example 1, provided that the compound (56) represented by the structural formula (56) was used as a luminescent dye.

[Coloring Discharging Comparison Test 16]

Figure 20:
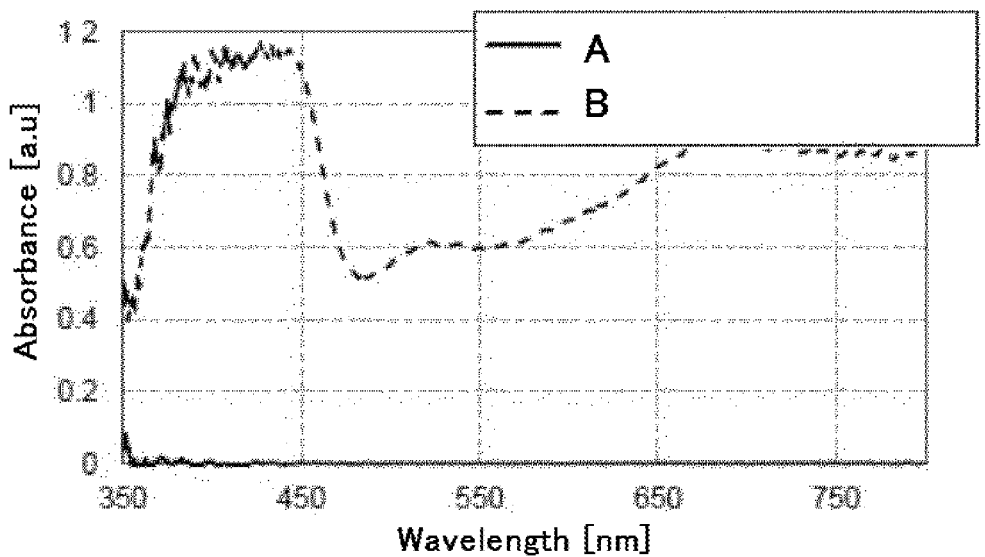
FIG. 20 is a diagram depicting absorption spectra of the discolored state and colored state of the display electrode with the electrochromic display layer produced in Example 16, where A denotes the absorption spectrum of the compound of Example 16 in the discolored state, and B denotes the absorption spectrum of the compound of Example 16 in the colored state.

An absorption spectrum was measured in the same manner as in [Coloring Discharging Comparison Test 1]. The discolored state and charged state of the absorption spectra are depicted in FIG. 20. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Example 17

Synthesis of Electrochromic Compound (57) [Structural Formula (57)]

<a> Synthesis of Intermediate (57-1, 57-2)

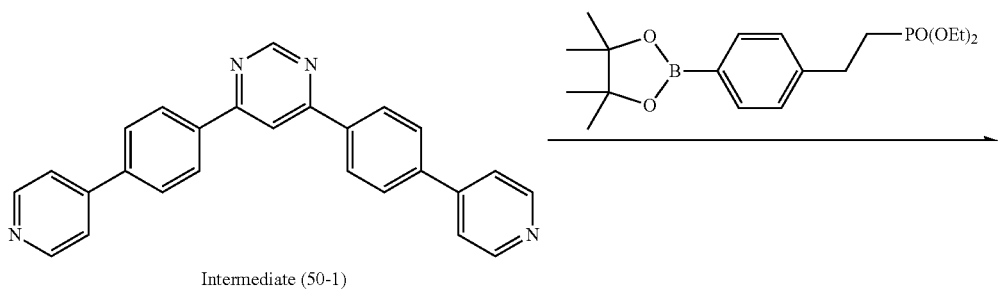

Intermediate (50-1)

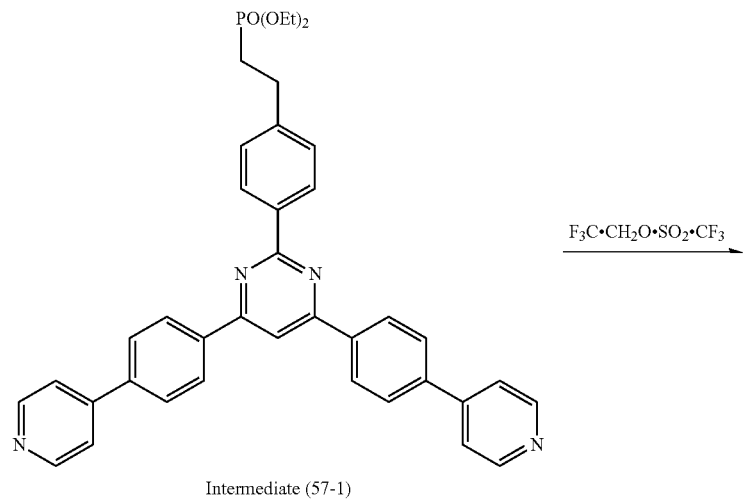

Intermediate (57-1)

-continued

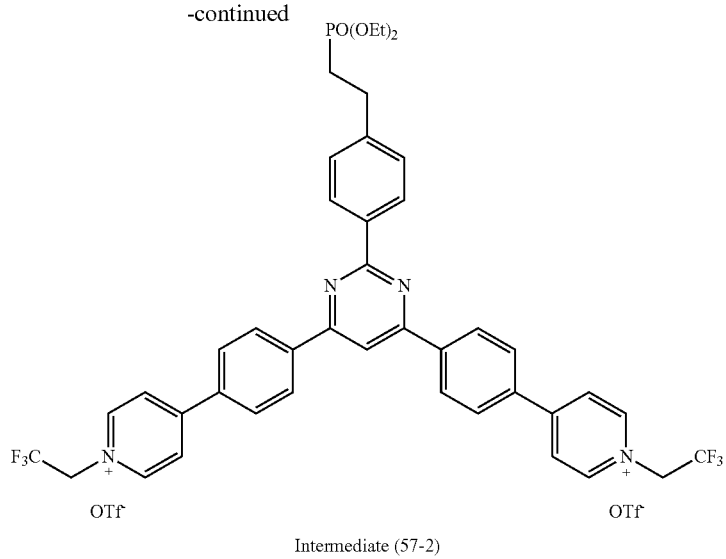

Intermediate (57-2)

An intermediate (57-2) was obtained by carrying out a reaction and purification in the same manner as in Example 14, provided that, in (b) of Example 14, n-butyl bromide was replaced with 2,2,2-trifluoroethyl trifluoromethane sulfonate. The yielded amount was 217 mg, and the yield was 59%.

<c> Synthesis of Electrochromic Compound [Structural Formula (57)]

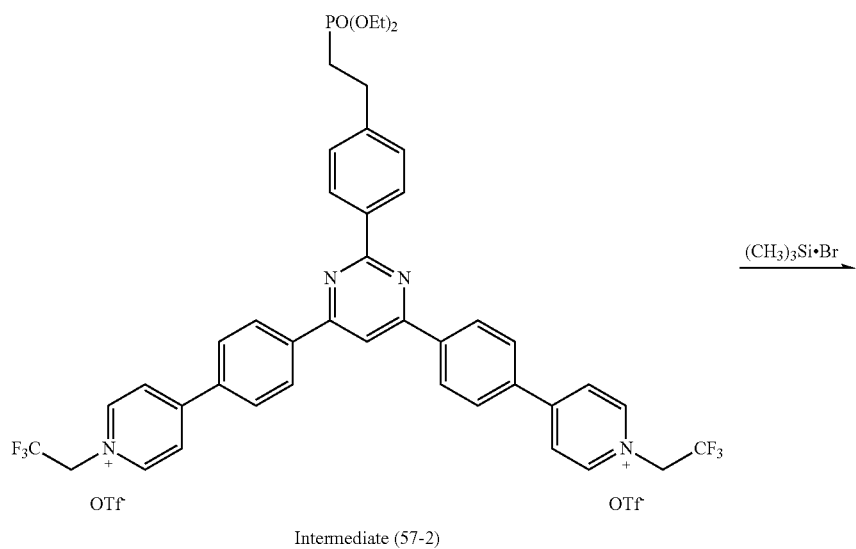

Intermediate (57-2)

-continued

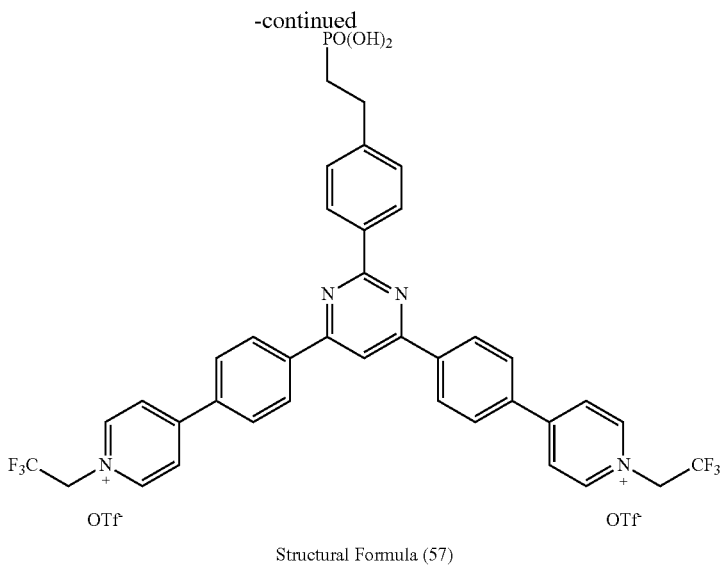

Structural Formula (57)

A target was obtained by carrying out a reaction and purification in the same manner as in Example 14, provided that, in (c) of Example 14, the intermediate (31-2) was replaced with the intermediate (57-2). The yielded amount was 198 mg, and the yield was 96%.

$^1$H NMR (500 MHz, CDCl$_3$, δ): 9.29 (d, J=6.9 Hz, 4H), 8.89 (s, 1H), 8.85 (t, J=7.5 Hz, 8H), 8.64 (d, J=8.0 Hz, 2H), 8.40 (d, J=9.2 Hz, 4H), 7.52 (d, J=8.5 Hz, 2H), 5.84 (q, J=8.6 Hz, 4H), 2.92 (quint., J=4.6 Hz, 2H), 1.88-1.95 (m, 2H)

[Production and Evaluation of Electrochromic Display Element]

An electrochromic display element was produced in the same manner as the method described in [Production and Evaluation of Electrochromic Display Element] of Example 1, provided that the compound (57) represented by the structural formula (57) was used as a luminescent dye.

[Coloring Discharging Comparison Test 17]

Figure 21:
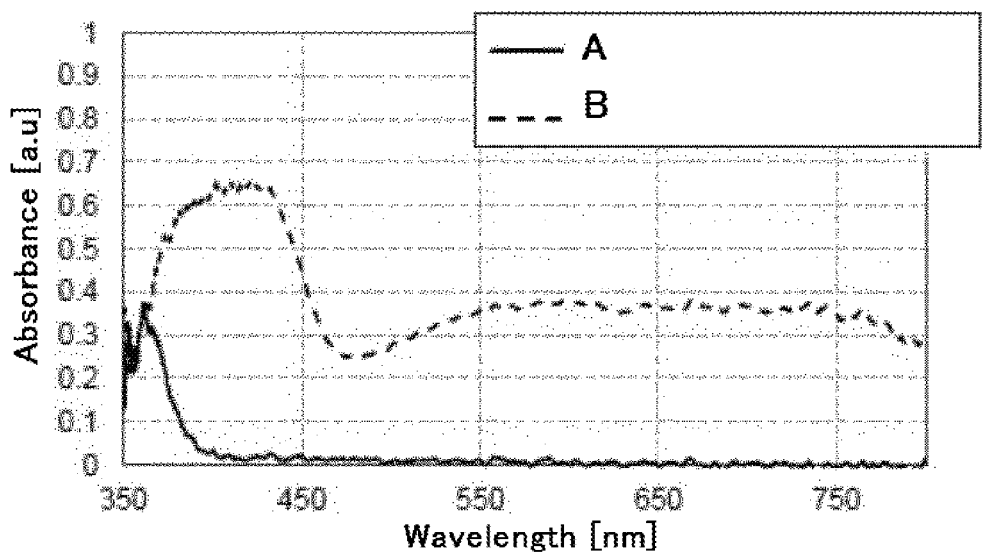
FIG. 21 is a diagram depicting absorption spectra of the discolored state and colored state of the display electrode with the electrochromic display layer produced in Example 17, where A denotes the absorption spectrum of the compound of Example 17 in the colored state, and B denotes the absorption spectrum of the compound of Example 17 in the discolored state.

An absorption spectrum was measured in the same manner as in [Coloring Discharging Comparison Test 1]. The discolored state and charged state of the absorption spectra are depicted in FIG. 21. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

(Summery of Results)

As depicted in FIGS. 4 to 21, it was confirmed from the results of the absorptions spectra of the discolored state of the compound that there was an absorption in the visible region and the electrochromic display layer was tinted with yellow in Comparative Example 1, but there was no absorption in the visible region and the electrochromic display layers were transparent in Examples 1 to 17. Moreover, it was further confirmed from the absorption spectra of the colored state that the electrochromic compounds thereof had the absorption in the entire visible region, and colored in black. These results were clear from the results of the color value measurement.

Based on these results, a high-contrast dimming element could be attained using the electrochromic compound of the present invention.

Example 18

Synthesis of Electrochromic Compound (9)
[Structural Formula (9)]

<a> Synthesis of Intermediate (9-1)

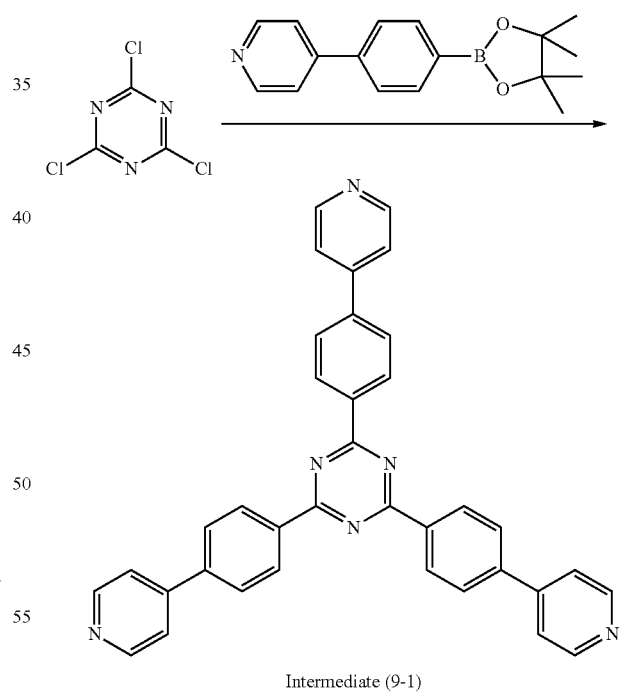

Intermediate (9-1)

A flask was charged with 3.0 g of 2,4,6-trichloro-1,3,5-triazine, and was purged with argon gas. To the flask, thereafter, dioxane (100 mL), phenylpyridine boronic acid pinacol ester (18.5 g), and PdCl$_2$ (PPh$_3$)$_2$ (600 mg) were added. To the mixture, 2M K$_2$CO$_3$ (17 mL) was added, and the resulting mixture was stirred for 14 hours at 50° C., followed by stirring for 16 hours at room temperature. The resultant was filtered with Celite, and water and chloroform were added to the filtrate to separate an organic layer. Thereafter, a water layer was extracted 3 times with chloroform. The combined organic layer was washed with saturated salt water, followed by drying with sodium sulfate to condensate the filtrate, to thereby obtain a crude product (the yielded amount: 7.5 g).

The crude product was purified by silica-gel column chromatography (eluent: $CHCl_3$/methanol=93/7), and the obtained solids were dispersed and washed in chloroform/hexane. The solids were collected by filtration, and the obtained solids were vacuum dried to thereby obtain a target (the yielded amount: 6.9 g, the yield: 78%) as white solids.

<b> Synthesis of Electrochromic Compound (9) [Structural Formula (9)]

The yielded amount was 1.1 g, and the yield was 85%.

[Production and Evaluation of Electrochromic Display Element]

(a) Formation of Display Electrode and Electrochromic Display Layer

First, a glass substrate with FTO electric conductive film in the size of 25 mm×30 mm (manufactured by AGC Fabritech Co., Ltd.) was provided. Onto the 19 mm×15 mm region of the top surface of the glass substrate, a titanium oxide nano particle dispersion liquid (SP210, manufactured by Showa Titanium K.K.) was applied by spin coating, followed by performing annealing for 15 minutes at 120° C., to thereby form a titanium oxide particle film. Onto the titanium oxide particle film, a 1% by weight 2,2,3,3-tetra-

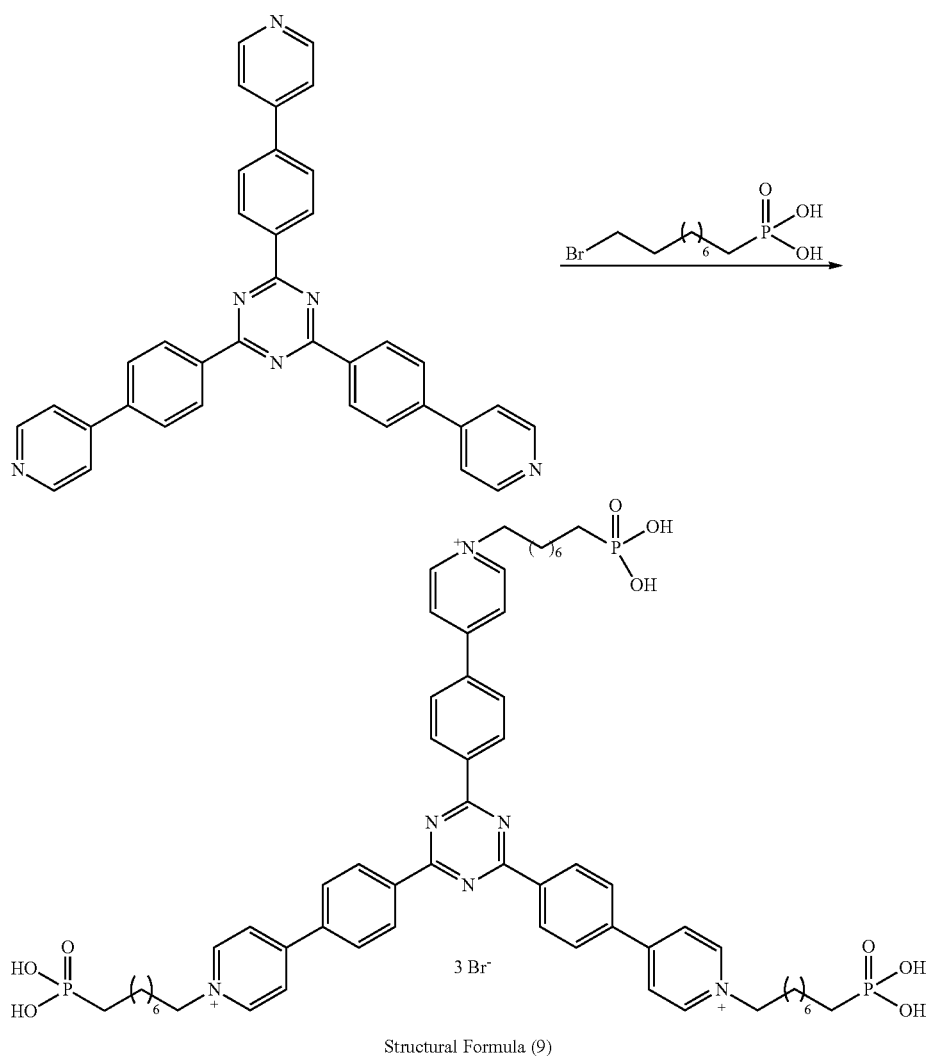

Structural Formula (9)

A 25 mL three-necked flask was charged with 0.5 g of the intermediate (9-1), 4.0 g of 8-bromooctyl phosphonate, and 3.0 mL of dimethyl formamide, and the resulting mixture was allowed to react for 8 hours at 90° C. After returning the resulting solution to room temperature, the solution was discolored into 2-propanol. Subsequently, the obtained solids were dispersed in 2-propanol, followed by collecting the solids. The obtained solids were vacuum dried for 2 days at 100° C., to thereby obtain a target.

fluoropropanol solution of the compound represented by the structural formula (22) was applied as a coating liquid by spin coating, and the applied solution was subjected to annealing for 10 minutes at 120° C., to thereby form a display layer 5 having the electrochromic compound adsorbed on surfaces of the titanium oxide particles.

Note that, a structure of the produced electrochromic display element conformed to the structure of FIG. 2 (provided that, a white reflective layer was excluded).

(b) Formation of White Reflective Layer

Moreover, a solution, in which a urethane paste (HW140SF, manufactured by DIC Corporation) was dissolved as a binding polymer in an amount of 10% by weight in a 2,2,3,3-tetrafluoropropanol solution, was provided. To this solution, 50% by weight of titanium oxide particles (product name: CR90, manufactured by ISHIHARA SANGYO KAISHA, LTD., average particle diameter: about 250 nm) were dispersed to prepare a paste. The paste was applied onto a surface of the electrochromic layer by spin coating, and the coated paste was subjected to annealing for 5 minutes at 120° C., to thereby form a white reflective layer of about 1 μm.

(c) Formation of Counter Electrode

Separately from the glass substrate, a glass substrate with a 25 mm×30 mm ITO electroconductive film (manufactured by GEOMATEC Co., Ltd.) was provided, and used as a counter substrate.

(d) Production of Electrochromic Display Element

A cell was produced by bonding the display substrate and the counter substrate together via a spacer having a thickness of 75 μm. Next, 20% by weight of tetrabutyl ammonium perchlorate was dissolved in dimethyl sulfoxide, to thereby an electrolyte solution. The electrolyte solution was then enclosed in the cell, to thereby produce an electrochromic display element.

Comparative Example 1

The electrochromic compound represented by the following structural formula (44), which was disclosed as [Chem. 46] in JP-A No. 2011-102287, was synthesized.

chromic display layer was transparent. When the voltage of −1.5 V was applied using a potentiostat (ALS-660C, manufactured by BAS Inc.), the electrochromic display layer was colored in black.

Figure 23:
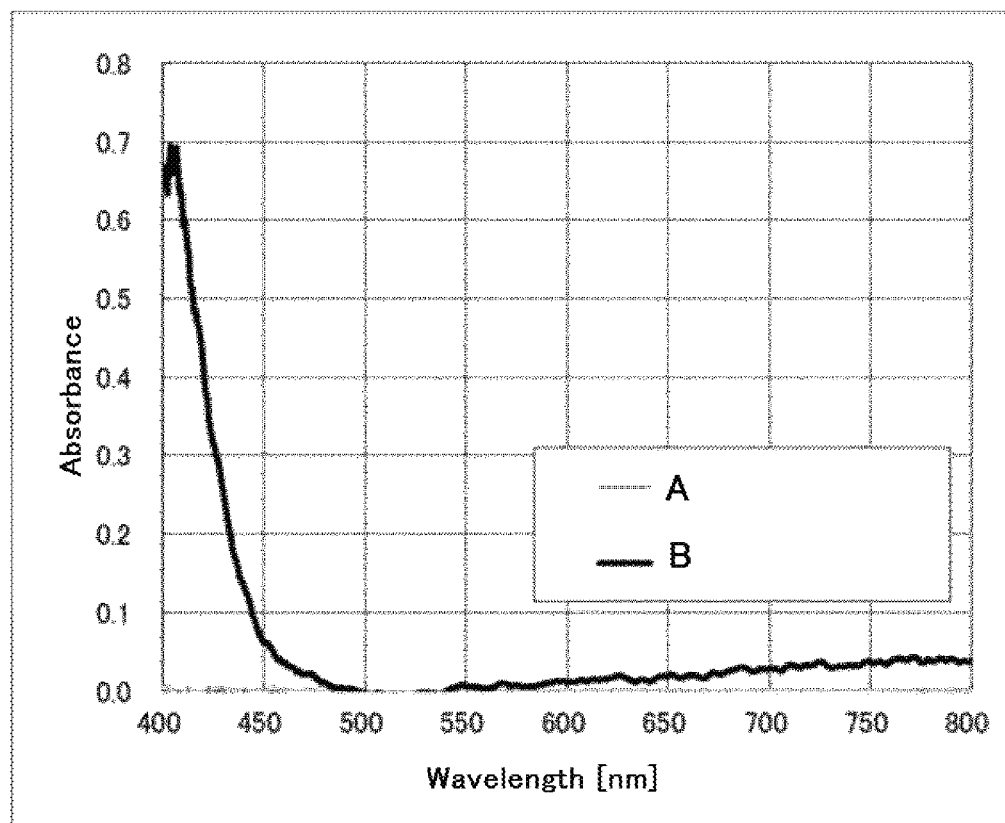
FIG. 23 is a diagram depicting absorption spectra of the discolored state of the electrochromic display element produced in Example 18 and the electrochromic display element in Comparative Example 1, where A denotes the absorption spectrum of the compound of Example 18 in the discolored state, and B denotes the absorption spectrum of the compound of Comparative Example 1 in the discolored state.

FIG. 23 depicts a comparison between the absorption spectrum of the discolored state of the electrochromic display layer (d) of Example 18 and the absorption spectrum of the discolored state of the electrochromic display layer (d) of Comparative Example 1. In Comparative Example 1, the absorption was observed at around 400 nm even in the discolored state, and the discolored body had tinted more than the electrochromic compound of Example 1.

Figure 24:
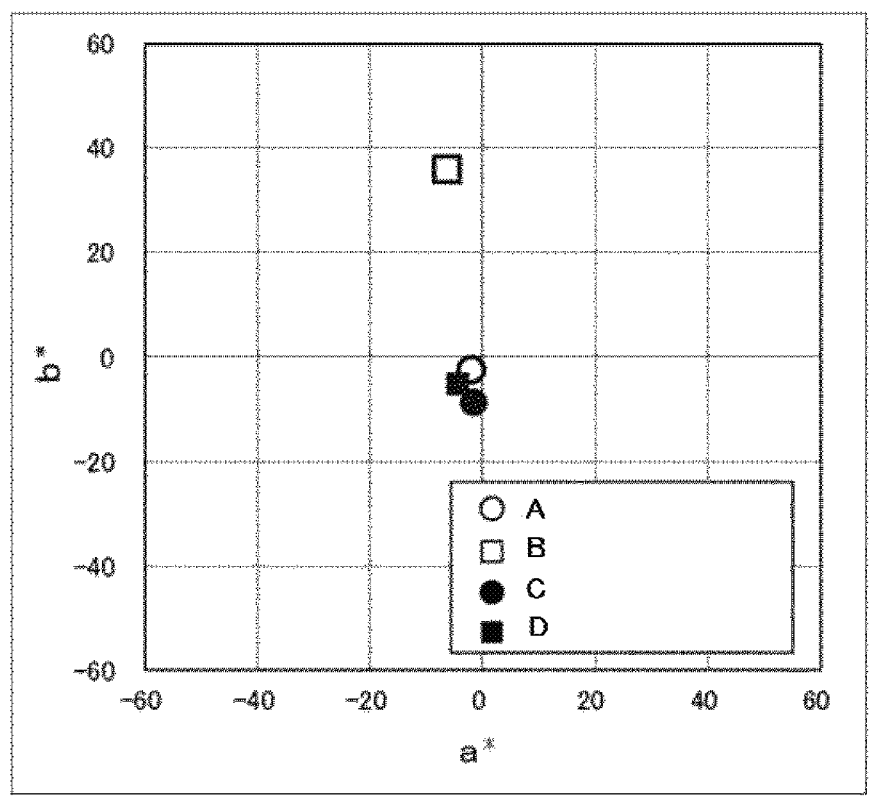
FIG. 24 is a diagram depicting a comparison in a color value between the electrochromic display element produced in Example 18 and the electrochromic display element in Comparative Example 1, where A denotes the color value of the compound of Example 18 in the discolored state, B denotes the color value of the compound of Comparative Example 1 in the discolored state, C denotes the color value of the compound of Example 18 in the colored state, and D denotes the color value of the compound of Comparative Example 1 in the colored state.

The electrochromic display elements (d) produced in Example 18 and Comparative Example 1 were each subjected to comparison evaluation of coloring and discoloring. The evaluation of coloring/discoloring was carried out by applying diffused light using a spectrophotometer MCPD7700, manufactured by Otsuka Electronics Co., Ltd. The color value was evaluated in CIE L*a*b* color space, and a* and b* were plotted in FIG. 24.

In the colored state after applying the voltage of −4.0 V to each display element, both of the electrochromic display elements of Example 18 and Comparative Example 1 had the values of a* and b* plotted to very close to the starting point (0), and it was confirmed that they were both colored substantially in black.

In the discolored state before applying the voltage, the plotted values a* and b* of Example 18 indicated that the color of Example 18 was substantially the same to Japan Color White that would be plotted on the starting point. On the other hand, Comparative Example 1 had a large value of b*, which indicated that it was tinted with yellow.

Structural Formula (44)

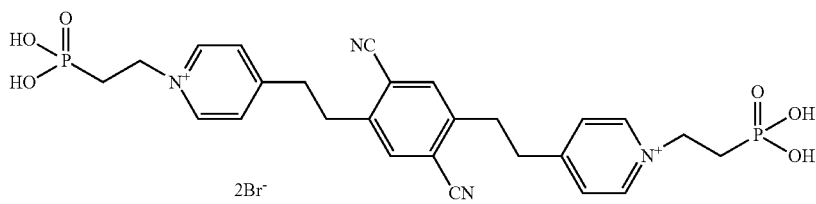

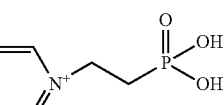

An electrochromic display element was produced by forming a display electrode and an electrochromic display layer in the same manner as in (a) to (d) of Example 18, provided that the obtained electrochromic compound was used.

[Coloring Discharging Comparison Test 1]

Figure 22:
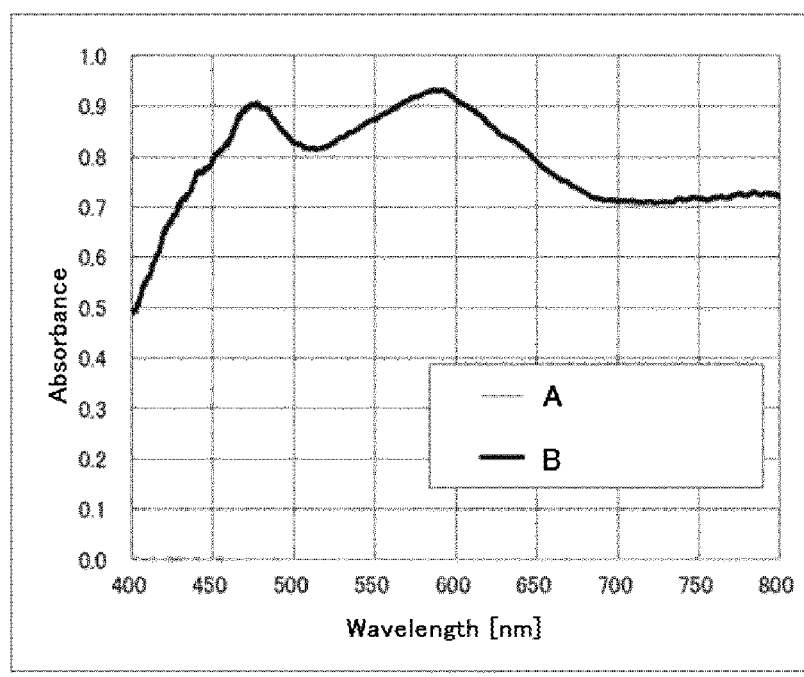
FIG. 22 is a diagram depicting absorption spectra of the discolored state and colored state of the display electrode with the electrochromic display layer produced in Example 18, where A denotes the absorption spectrum of the compound of Example 18 in the discolored state, and B denotes the absorption spectrum of the compound of Example 18 in the colored state.

Each of the display electrodes (a) to each of which the electrochromic display layer had been formed, which were produced in Example 18 and Comparative Example 1, was placed in a quartz cell. A platinum electrode was used as a counter electrode, and an Ag/Ag+ (RE-7, manufactured by BAS Inc.) was used as a reference electrode. An electrolyte solution was prepared by dissolving 0.1 M of tetrabutylammonium perchlorate in dimethyl sulfoxide, and the cell was filled with the electrolyte solution. To this quartz cell, light was applied from a deuterium tungsten halogen light source (DH-2000, manufactured by Ocean Optics, Inc.). The transmitted light was detected by a spectrometer (USB4000, manufactured by Ocean Optics, Inc.), to measure the absorption spectrum. The absorption spectra of the discolored state and colored state are presented in FIG. 22. In the discolored state before applying voltage, there was no absorption in the entire visible region of 400 nm to 700 nm, and the electro- It was found from the results above that Example 18 had fewer tints in the discolored state and had high white reflectance in comparison between the electrochromic display element of Example 18 and that of Comparative Example 1.

Example 19

Production and Evaluation of Electrochromic Dimming Element (a) Formation of Display Electrode and Electrochromic Display Layer First, a glass substrate with FTO electric conductive film in the size of 25 mm×30 mm (manufactured by AGC Fabritech Co., Ltd.) was provided. Onto the 19 mm×15 mm region of the top surface of the glass substrate, a titanium oxide nano particle dispersion liquid (SP210, manufactured by Showa Titanium K.K.) was applied by spin coating, followed by performing annealing for 15 minutes at 120° C., to thereby form a titanium oxide particle film. Onto the titanium oxide particle film, a 1% by weight 2,2,3,3-tetrafluoropropanol solution of the compound represented by the structural formula (9) was applied as a coating liquid by spin coating, and the applied solution was subjected to annealing for 10 minutes at 120° C., to thereby form a display layer 5 having the electrochromic compound adsorbed on surfaces of the titanium oxide particles.

Note that, a structure of the produced electrochromic dimming element conformed to the structure of FIG. 3 (provided that, a white reflective layer was excluded).

(b) Formation of Counter Electrode

Separately from the glass substrate, a glass substrate with a 25 mm×30 mm ITO electroconductive film (manufactured by GEOMATEC Co., Ltd.) was provided, and used as a counter substrate.

(c) Production of Electrochromic Dimming Element

A cell was produced by bonding the display substrate and the counter substrate together via a spacer having a thickness of 75 μm. Next, 20% by weight of tetrabutyl ammonium perchlorate was dissolved in dimethyl sulfoxide, to thereby an electrolyte solution. The electrolyte solution was then enclosed in the cell, to thereby produce an electrochromic dimming element.

[Coloring Discharging Comparison Test 2]

Light was applied to the dimming element (c) produced in Example 19 from tungsten halogen light source (DH-2000, manufactured by Ocean Optics, Inc.). The transmitted light was detected by a spectrometer (USB4000, manufactured by Ocean Optics, Inc.), to measure the absorption spectrum. In the discolored state before applying voltage, there was no absorption in the entire visible region of 400 nm to 700 nm, and the dimming element was transparent. Especially, the transmittance at 550 nm was 80%. When the voltage of −6.0 V was applied to this element for 2 seconds, the dimming element colored in black, and it could be confirmed that the transmittance at 550 nm was reduced to 25%.

Based on the results above, the dimming element of high contrast could be attained by using the electrochromic compound represented by the structural formula (9).

Example 201

Synthesis of Electrochromic Compound (10) [Structural Formula (10)]

<a> Synthesis of Intermediate (10-1)

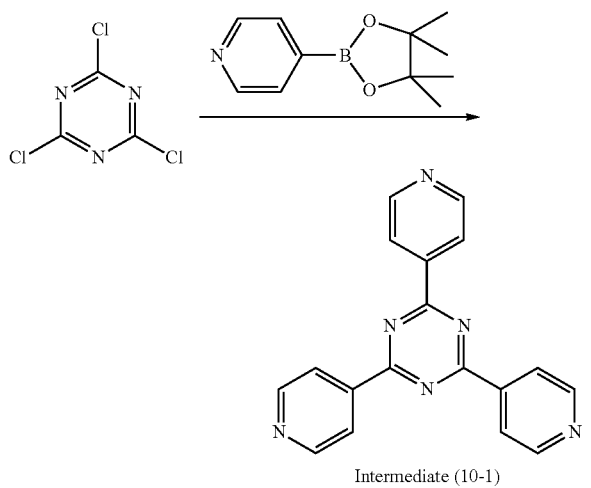

Intermediate (10-1)

A flask was charged with 3.0 g of 2,4,6-trichloro-1,3,5-triazine, and was purged with argon gas. To the flask, thereafter, dioxane (100 mL), pyridineboronic acid pinacol ester (9.0 g), and $PdCl_2$ $(PPh_3)_2$ (300 mg) were added. To the mixture, 2M $K_2CO_3$ (14 mL) was added, and the resulting mixture was stirred for 8 hours at 50° C., followed by stirring for 10 hours at room temperature. The resultant was filtered with Celite, and water and chloroform were added to the filtrate to separate an organic layer. Thereafter, a water layer was extracted 3 times with chloroform. The combined organic layer was washed with saturated salt water, followed by drying with sodium sulfate to condensate the filtrate, to thereby obtain a crude product (the yielded amount: 4.5 g).

The crude product was purified by silica-gel column chromatography (eluent: $CHCl_3$/methanol=93/7), and the obtained solids were dispersed and washed in chloroform/hexane. The solids were collected by filtration, and the obtained solids were vacuum dried to thereby obtain a target compound as white solids (the yielded amount: 4.1 g, the yield: 81%).

<b> Synthesis of Electrochromic Compound (10) [Structural Formula (10)]

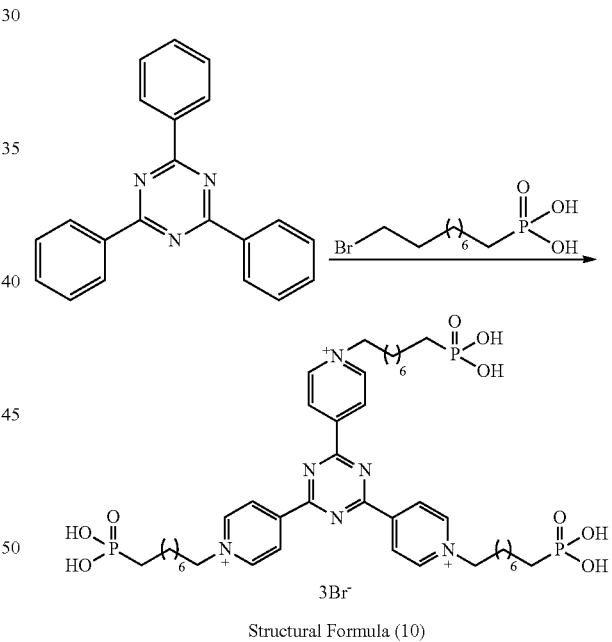

Structural Formula (10)

A target, which was a colorless powder, was obtained using the intermediate (10-1) and 8-bromooctyl phosphonate in the same manner as in Example 18<b>.

[Production and Evaluation of Electrochromic Display Element]

An electrochromic display element was produced in the same manner as in Example 18, provided that the electrochromic compound for use was changed to the electrochromic compound synthesized in Example 20.

[Coloring Discharging Test 3]

Figure 25:
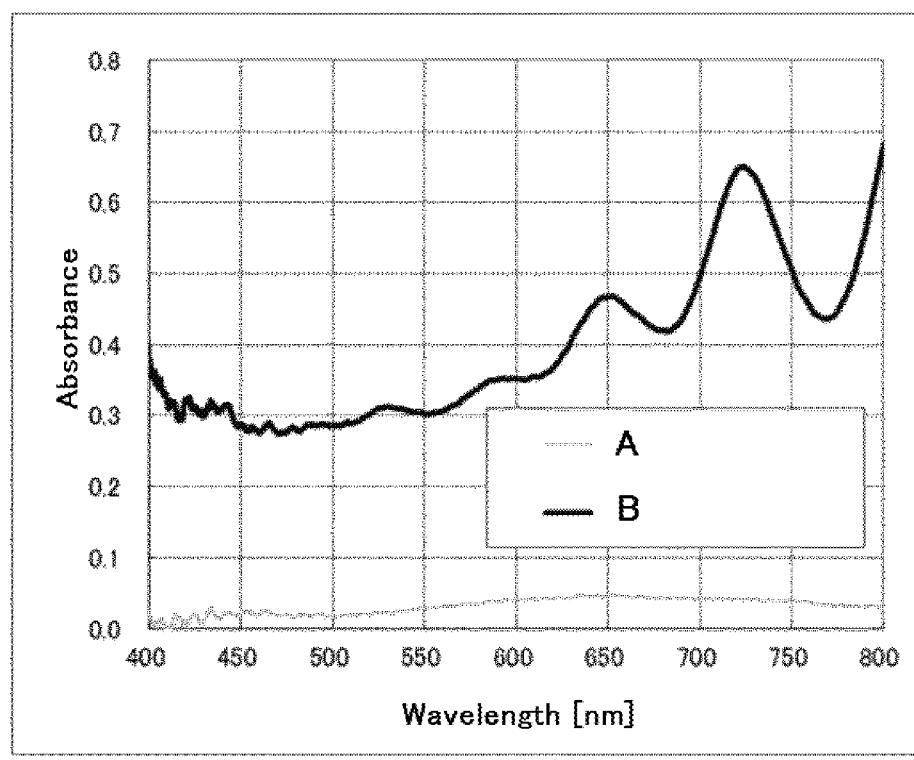
FIG. 25 is a diagram depicting absorption spectra of the discolored state and colored state of the display electrode with the electrochromic display layer produced in Example 20, where A denotes the absorption spectrum of the compound of Example 20 in the discolored state, and B denotes the absorption spectrum of the compound of Example 20 in the colored state.

The absorption spectrum was measured in the same manner as in Example 18. The resulting absorption spectra are depicted in FIG. 25. In the discolored state before applying voltage, there was no absorption in the entire visible region of 400 nm to 700 nm, and the electrochromic display layer was transparent. When the voltage of −1.5 V was applied using a potentiostat (ALS-660C, manufactured by BAS Inc.), the electrochromic display layer was colored in black.

Each electrochromic display element produced in each Example colored in black as the voltage of −3 V was applied for 3 seconds. At this time, the reflectance of 550 nm was as presented in the following table.

TABLE 1

|  | Reflectance (550 nm)/% |
|---|---|
| Example 1 | 4.0 |
| Example 3 | 4.3 |
| Example 4 | 4.5 |
| Example 5 | 4.2 |
| Example 6 | 3.5 |
| Example 7 | 3.6 |
| Example 8 | 3.9 |
| Example 9 | 4.0 |
| Example 10 | 4.0 |
| Example 11 | 4.8 |
| Example 12 | 4.2 |
| Example 13 | 5.0 |
| Example 14 | 4.2 |
| Example 15 | 4.4 |
| Example 16 | 4.0 |
| Example 17 | 4.1 |
| Example 18 | 4.8 |
| Example 19 |  |
| Example 20 | 4.5 |
| Comparative Example 1 | 6.7 |

The embodiments of the present invention are as follows:

<1> An electrochromic compound, represented by the following general formula (I):

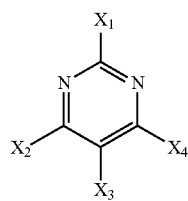

General Formula (I)

where $X_1$ to $X_4$ are each a substituent represented by the following general formula (II), an alkyl group that may contain a functional group, an aromatic hydrocarbon group that may contain a functional group, or a hydrogen atom, and at least two selected from $X_1$ to $X_4$ are the substituents represented by the general formula (II):

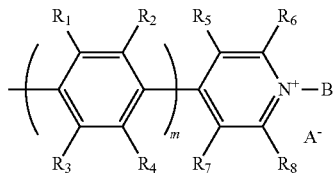

General Formula (II)

where $R_1$ to $R_8$ are each independently a hydrogen atom, or a monovalent group that may contain a substituent; B is a substituted or unsubstituted monovalent group that may contain a functional group; $A^-$ is a monovalent anion; and m is any of 0 to 3, and $R_1$ to $R_8$, B, and m may each independently be different when a plurality of the substituents represented by the general formula (II) are present.

<2> The electrochromic compound according to <1>, wherein three selected from $X_1$ to $X_4$ in the general formula (I) are the substituents each represented by the general formula (II).

<3> The electrochromic compound according to <1>, wherein any two selected from $X_1$, $X_2$, and $X_4$ are the substituents each represented by the general formula (II).

<4> The electrochromic compound, represented by the general formula (III):

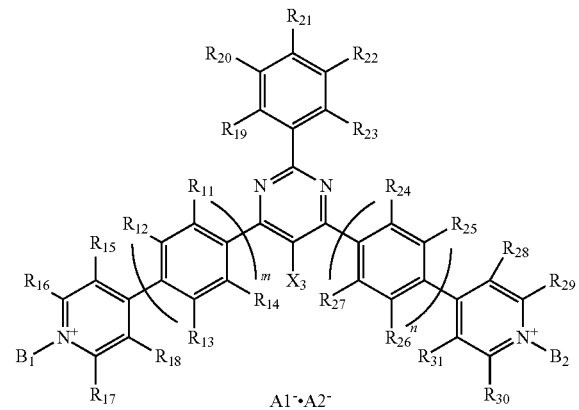

General Formula (III)

where $X_3$ is a hydrogen atom, or a monovalent group that may contain a substituent; $R_{11}$ to $R_{31}$ are each independently a hydrogen atom, or a monovalent group that may contain a substituent; $B_1$ and $B_2$ are each independently a substituted or unsubstituted monovalent group that may contain a functional group; and $A1^-$ and $A2^-$ are each a monovalent anion.

<5> An electrochromic compound, represented by the following general formula (IV) or (V):

General Formula (IV)

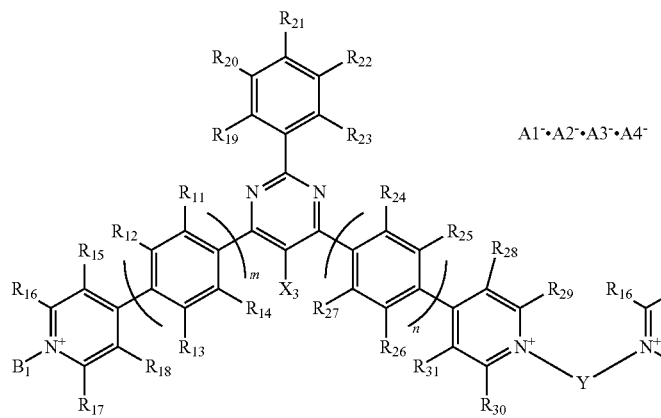

General Formula (V)

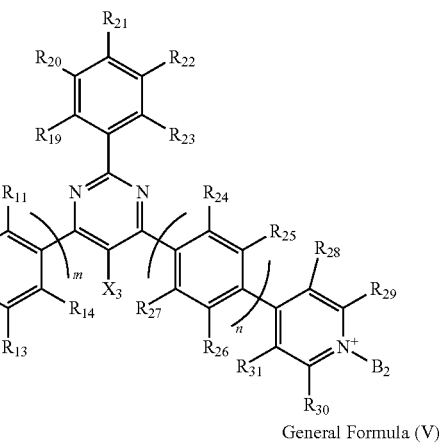

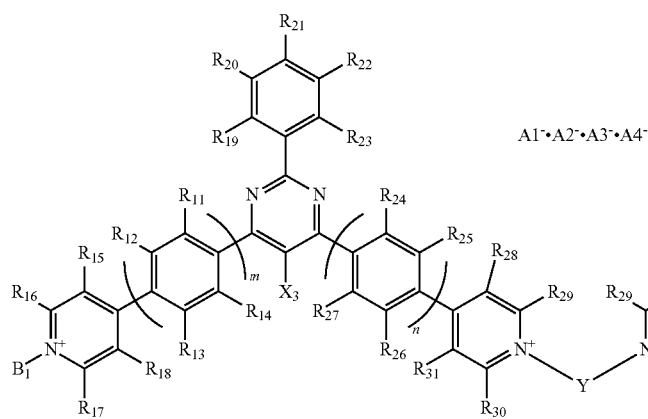

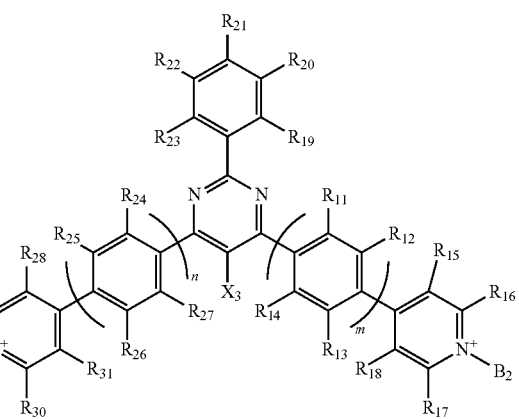

where $X_3$ is a hydrogen atom or a monovalent group that may contain a substituent; $R_{11}$ to $R_{31}$ are each independently a hydrogen atom or a monovalent group that may contain a substituent; $B_1$ and $B_2$ are each independently a substituted or unsubstituted aliphatic hydrocarbon group that may contain a functional group, or a substituted or unsubstituted aromatic hydrocarbon group that may contain a functional group; $A1^-$ and $A2^-$ are each a monovalent anion; m and n are each independently 1, 2, or 3; and Y is a bivalent organic group, which contains at least one methylene group, and may contain a substituted or unsubstituted aliphatic hydrocarbon group or a substituted or unsubstituted aromatic hydrocarbon group.

<6> The electrochromic compound according to any one of <1> to <5>, wherein at least one selected from all B present, or B1, or B2, or both contain a functional group capable of directly or indirectly bonding to a hydroxyl group.

<7> The electrochromic compound according to <6>, wherein at least one selected from $X_1$ to $X_4$ in the general formula (I) contains a functional group capable of directly or indirectly bonding to a hydroxyl group.

<8> The electrochromic compound according to <6>, wherein the functional group capable of directly or indirectly bonding to a hydroxyl group is a phosphonic acid group, a phosphoric acid group, a carboxylic acid group, a silyl group, or a silanol group.

<9> An electrochromic compound, represented by the following general formula (Ia):

General Formula (Ia)

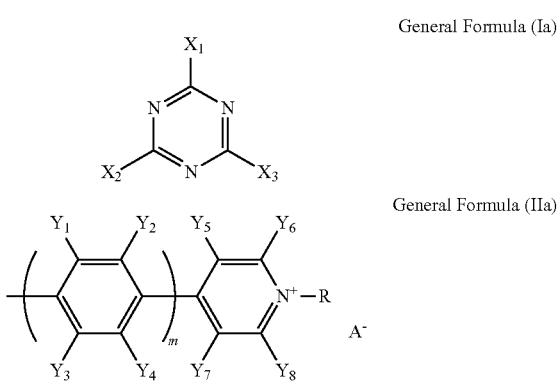

General Formula (IIa)

where at least two selected from $X_1$, $X_2$, and $X_3$ each have a structure represented by the general formula (IIa), and when two selected from $X_1$, $X_2$, and $X_3$ each have the structure represented by the general formula (IIa), the rest is an aliphatic hydrocarbon group that may contain a functional group, an aromatic hydrocarbon group that may contain a functional group, or a hydrogen atom; $Y_1$ to $Y_8$ are each independently a hydrogen atom, or a monovalent group that may contain a substituent; R is a substituted or unsubstituted monovalent group that may contain a functional group; and m is any of 0 to 3; $A^-$ is a monovalent anion, and $Y_1$ to $Y_8$, m, and $A^-$ of the general formula (IIa) in $X_1$, $X_2$, or $X_3$ of the general formula (Ia) may be independently different.

<11> The electrochromic compound according to <9>, wherein two selected from $X_1$, $X_2$, and $X_3$ of the general formula (Ia) each have a structure represented by the general formula (IIa).

<11> The electrochromic compound according to <9> or <10>, wherein at least one of all R of the general formula (IIa) present contains a functional group capable of directly or indirectly bonding to a hydroxyl group.

<12> The electrochromic compound according to any one of <9> to <11>, wherein at least one selected from $X_1$ to $X_3$ of the general formula (Ia) contains a functional group capable of directly or indirectly bonding to a hydroxyl group.

<13> The electrochromic compound according to any of <11> or <12>, wherein the functional group capable of directly or indirectly bonding to a hydroxyl group is a phosphonic acid group, a phosphoric acid group, a carboxylic acid group, a silyl group, or a silanol group.

<14> An electrochromic composition, containing:
the electrochromic compound according any one of <1> to <13>; and
an electroconductive or semiconductive nanostructure, to which the electrochromic compound is bonded or adsorbed.

<15> A display element, containing:
a display electrode;
a counter electrode facing the display electrode with a space therebetween; and
an electrolyte provided between the display electrode and the counter electrode,
wherein the electrochromic compound according to any one of <1> to <13> or the electrochromic composition according to <14> is provided on a surface of the display electrode.

<16> A dimming element, containing:
a display electrode;
a counter electrode facing the display electrode with a space therebetween; and
an electrolyte provided between the display electrode and the counter electrode,
wherein the electrochromic compound according to any one of <1> to <13> or the electrochromic composition according to <14> is provided on a surface of the display electrode, and
wherein the display electrode, the counter electrode, and the electrolyte are transparent.

Reference Signs List 1 display electrode
2 counter electrode
3 electrolyte
4 electrochromic compound
4a electrochromic composition
5 display layer
6 white reflective layer
10 display element
20 display element
30 dimming element

The invention claimed is:
1. An electrochromic compound, represented by the following general formula (I):

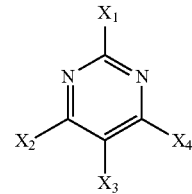

General Formula (I)

where $X_1$ to $X_4$ are each a substituent represented by the following general formula (II), an alkyl group that may contain a functional group, an aromatic hydrocarbon group that may contain a functional group, or a hydrogen atom, and at least two selected from $X_1$ to $X_4$ are the substituents represented by the general formula (II):

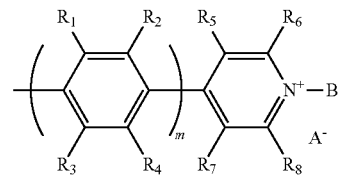

General Formula (II)

where $R_1$ to $R_8$ are each independently a hydrogen atom, or a monovalent group that may contain a substituent; B is a substituted or unsubstituted monovalent group that may contain a functional group; $A^-$ is a monovalent anion; and m is any of 0 to 3, and $R_1$ to $R_8$, B, and m may each independently be different when a plurality of the substituents represented by the general formula (II) are present.

2. The electrochromic compound according to claim 1, wherein three selected from $X_1$ to $X_4$ in the general formula (I) are the substituents each represented by the general formula (II).

3. The electrochromic compound according to claim 1, wherein any two selected from $X_1$, $X_2$, and $X_4$ are the substituents each represented by the general formula (II).

4. The electrochromic compound according to claim 1, represented by the general formula (III):

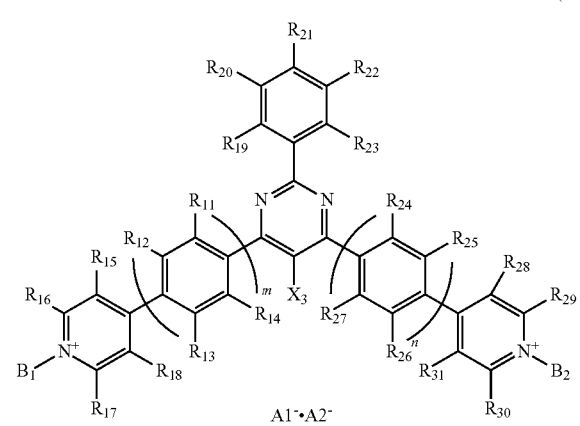

General Formula (III)

where $X_3$ is a hydrogen atom, or a monovalent group that may contain a substituent; $R_{11}$ to $R_{31}$ are each independently a hydrogen atom, or a monovalent group that may contain a substituent; $B_1$ and $B_2$ are each independently a substituted or unsubstituted monovalent group that may contain a functional group; and $A1^-$ and $A2^-$ are each a monovalent anion.

5. The electrochromic compound according to claim 1, represented by the following general formula (IV) or (V):

formula (I) contains a functional group capable of directly or indirectly bonding to a hydroxyl group.

8. The electrochromic compound according to claim 6, wherein the functional group capable of directly or indirectly bonding to a hydroxyl group is a phosphonic acid group, a phosphoric acid group, a carboxylic acid group, a silyl group, or a silanol group.

General Formula (IV)

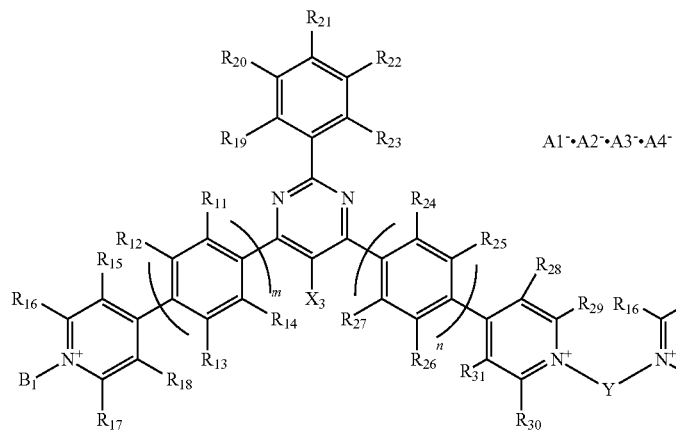 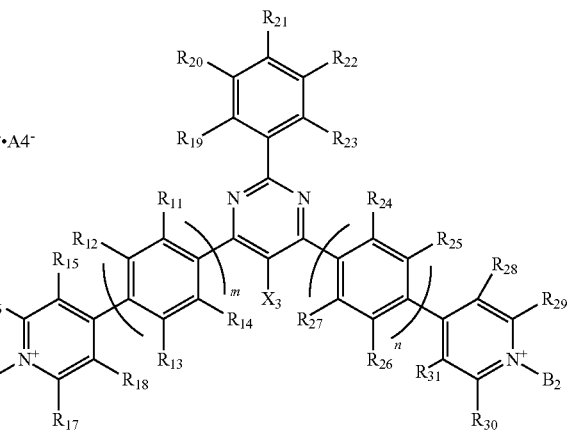

General Formula (V)

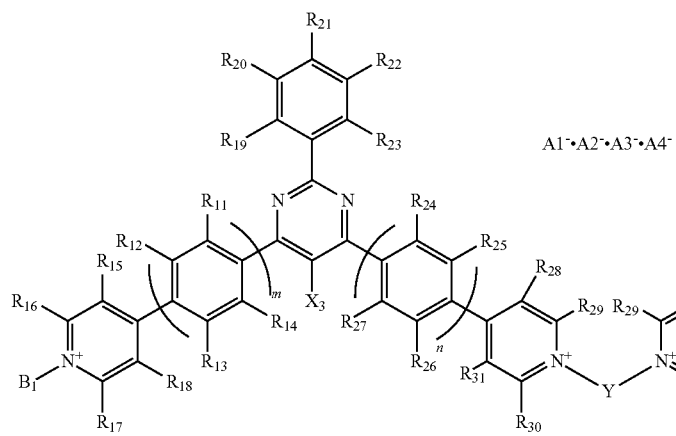 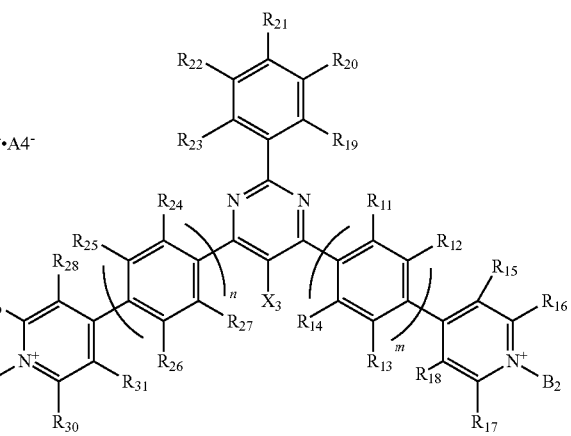

where $X_3$ is a hydrogen atom or a monovalent group that may contain a substituent; $R_{11}$ to $R_{31}$ are each independently a hydrogen atom or a monovalent group that may contain a substituent; $B_1$ and $B_2$ are each independently a substituted or unsubstituted aliphatic hydrocarbon group that may contain a functional group, or a substituted or unsubstituted aromatic hydrocarbon group that may contain a functional group; $A1^-$ and $A2^-$ are each a monovalent anion; m and n are each independently 1, 2, or 3; and Y is a bivalent organic group, which contains at least one methylene group, and may contain a substituted or unsubstituted aliphatic hydrocarbon group or a substituted or unsubstituted aromatic hydrocarbon group.

6. The electrochromic compound according to claim 1, wherein at least one selected from all B present, or B1, or B2, or both contain a functional group capable of directly or indirectly bonding to a hydroxyl group.

7. The electrochromic compound according to claim 6, wherein at least one selected from $X_1$ to $X_4$ in the general 9. An electrochromic composition, comprising:
the electrochromic compound according to claim 1; and
an electroconductive or semiconductive nanostructure, to which the electrochromic compound is bonded or adsorbed.

10. A display element, comprising:
a display electrode;
a counter electrode facing the display electrode with a space therebetween; and
an electrolyte provided between the display electrode and the counter electrode,
wherein the electrochromic compound according to claim 1 is provided on a surface of the display electrode.

11. A dimming element, comprising:
a display electrode;
a counter electrode facing the display electrode with a space therebetween; and
an electrolyte provided between the display electrode and the counter electrode,
wherein the electrochromic compound according to claim 1 is provided on a surface of the display electrode, and wherein the display electrode, the counter electrode, and the electrolyte are transparent.

12. An electrochromic compound, represented by the following general formula (Ia):

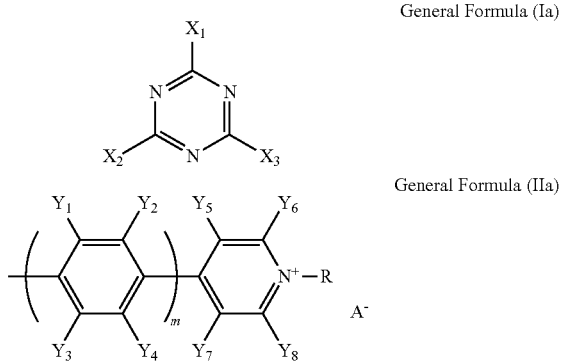

General Formula (Ia)

General Formula (IIa)

where at least two selected from $X_1$, $X_2$, and $X_3$ each have a structure represented by the general formula (IIa), and when two selected from $X_1$, $X_2$, and $X_3$ each have the structure represented by the general formula (IIa), the rest is an aliphatic hydrocarbon group that may contain a functional group, an aromatic hydrocarbon group that may contain a functional group, or a hydrogen atom; $Y_1$ to $Y_8$ are each independently a hydrogen atom, or a monovalent group that may contain a substituent; R is a substituted or unsubstituted monovalent group that may contain a functional group; and m is any of 0 to 3; $A^-$ is a monovalent anion, and $Y_1$ to $Y_8$, m, and $A^-$ of the general formula (IIa) in $X_1$, $X_2$, or $X_3$ of the general formula (Ia) may be independently different.

13. The electrochromic compound according to claim 12, wherein two selected from $X_1$, $X_2$, and $X_3$ of the general formula (Ia) each have a structure represented by the general formula (IIa).

14. The electrochromic compound according to claim 12, wherein at least one of all R of the general formula (IIa) present contains a functional group capable of directly or indirectly bonding to a hydroxyl group.

15. The electrochromic compound according to claim 14, wherein the functional group capable of directly or indirectly bonding to a hydroxyl group is a phosphonic acid group, a phosphoric acid group, a carboxylic acid group, a silyl group, or a silanol group.

16. The electrochromic compound according to claim 12, wherein at least one selected from $X_1$ to $X_3$ of the general formula (Ia) contains a functional group capable of directly or indirectly bonding to a hydroxyl group.

* * * * *